US011207177B2

United States Patent
Zhang et al.

(10) Patent No.: US 11,207,177 B2
(45) Date of Patent: Dec. 28, 2021

(54) MITRAL VALVE PROSTHESIS IMPLANTATION

(71) Applicant: Micor Limited, Grand Cayman (KY)

(72) Inventors: Ji Zhang, Burnaby (CA); Brandon G. Walsh, Kaysville, UT (US); Cheng Y. Yang, Foster City, CA (US); Jinhua Zhu, San Francisco, CA (US)

(73) Assignee: Micor Limited, Grand Cayman (KY)

( * ) Notice: Subject to any disclaimer, the term of this patent is extended or adjusted under 35 U.S.C. 154(b) by 220 days.

(21) Appl. No.: 15/978,012

(22) Filed: May 11, 2018

(65) Prior Publication Data

US 2018/0263768 A1 Sep. 20, 2018

Related U.S. Application Data

(63) Continuation of application No. 15/344,486, filed on Nov. 4, 2016, now Pat. No. 10,588,741.

(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2436* (2013.01);
(Continued)

(58) Field of Classification Search
CPC .... A61F 2/2409; A61F 2/2418; A61F 2/2436; A61F 2/2439; A61F 2/2469; A61F 2/97;
(Continued)

(56) References Cited

U.S. PATENT DOCUMENTS 6,569,196 B1   5/2003  Vesely
7,831,219 B2  11/2010  Heuermann et al.
(Continued)

FOREIGN PATENT DOCUMENTS

CN      1897893      1/2007
CN    101180010      5/2008
(Continued)

OTHER PUBLICATIONS

International Search Report and Written Opinion from PCT/US2016/060729, dated Feb. 23, 2017, 14 pages.

*Primary Examiner* — Kathleen S Holwerda
(74) *Attorney, Agent, or Firm* — Nathan S. Smith; Sujohn Das; Morgan, Lewis & Bockius LLP

(57) ABSTRACT

A heart valve prosthesis and methods of its implantation are described herein. The prosthesis can be implanted in a heart of a patient by positioning an upper support of an anchoring element into a left atrium of the patient. The upper support can expand adjacent to a native valve structure of the patient. Further, the upper support can be moved against the native valve structure in a direction toward a left ventricle of the patient. A lower support of the anchoring element can be positioned into the left ventricle, spaced apart from the upper support, the lower support being separate from the upper support and coupled to the upper support by a flexible connector. Finally, the lower support can expand within the left ventricle, and engagement members of the lower support can engage with tissue of the native valve structure.

26 Claims, 25 Drawing Sheets

Related U.S. Application Data

(60) Provisional application No. 62/252,390, filed on Nov. 6, 2015.

(52) U.S. Cl.
CPC .......... *A61F 2/2439* (2013.01); *A61F 2/2469* (2013.01); *A61F 2220/0008* (2013.01); *A61F 2250/0069* (2013.01)

(58) Field of Classification Search
CPC ...... A61F 2/2427; A61F 2/2448; A61F 2/243; A61F 2/2433; A61F 2220/0008; A61F 2250/0069
See application file for complete search history.

(56) References Cited

U.S. PATENT DOCUMENTS

| | | | |
|---|---|---|---|
| 8,540,767 B2 | 9/2013 | Zhang et al. | |
| 8,585,755 B2 | 11/2013 | Chau et al. | |
| 8,795,356 B2 | 8/2014 | Quadri | |
| 8,961,597 B2 | 2/2015 | Subramanian et al. | |
| 8,986,361 B2 | 3/2015 | Bortlein | |
| 8,992,604 B2 | 3/2015 | Gross et al. | |
| 9,017,399 B2 | 4/2015 | Gross et al. | |
| 9,050,188 B2 | 6/2015 | Schweich, Jr. et al. | |
| 9,248,014 B2 | 2/2016 | Lane et al. | |
| 9,308,087 B2 | 4/2016 | Lane et al. | |
| 9,339,378 B2 | 5/2016 | Quadri et al. | |
| 9,387,078 B2 | 7/2016 | Gross et al. | |
| 9,421,094 B2 | 8/2016 | Schweich, Jr. et al. | |
| 9,427,315 B2 | 8/2016 | Schweich, Jr. et al. | |
| 9,433,500 B2 | 9/2016 | Chau et al. | |
| 9,492,273 B2 | 11/2016 | Wallace et al. | |
| 9,561,103 B2 | 2/2017 | Granada et al. | |
| 9,579,199 B2 | 2/2017 | Hauser et al. | |
| 9,585,751 B2 | 3/2017 | Morriss et al. | |
| 9,622,858 B2 | 4/2017 | Annest | |
| 9,675,454 B2 | 6/2017 | Vidlund et al. | |
| 9,717,591 B2 | 8/2017 | Chau | |
| 9,750,605 B2 | 9/2017 | Ganesan et al. | |
| 9,750,606 B2 | 9/2017 | Ganesan et al. | |
| 9,763,657 B2 | 9/2017 | Hacohen et al. | |
| 9,770,329 B2 | 9/2017 | Lane et al. | |
| 9,974,647 B2 | 5/2018 | Ganesan et al. | |
| 10,004,599 B2 | 6/2018 | Rabido et al. | |
| 10,010,414 B2 | 7/2018 | Cooper et al. | |
| 10,010,417 B2 | 7/2018 | Keidar | |
| 10,052,199 B2 | 8/2018 | Spence et al. | |
| 10,052,204 B2 | 8/2018 | Mclean et al. | |
| 10,064,718 B2 | 9/2018 | Keidar | |
| 10,117,741 B2 | 11/2018 | Schweich, Jr. et al. | |
| 10,143,552 B2 | 12/2018 | Wallace et al. | |
| 10,500,038 B1* | 12/2019 | Orlov | A61F 2/2436 |
| 2005/0075717 A1 | 4/2005 | Nguyen et al. | |
| 2005/0137690 A1 | 6/2005 | Salahieh et al. | |
| 2007/0043435 A1* | 2/2007 | Seguin | A61F 2/2433 623/2.11 |
| 2008/0154359 A1 | 6/2008 | Salgo et al. | |
| 2008/0071361 A1 | 8/2008 | Tuval et al. | |
| 2010/0286768 A1* | 11/2010 | Alkhatib | A61F 2/2418 623/2.11 |
| 2011/0125258 A1 | 5/2011 | La | |
| 2012/0022633 A1* | 1/2012 | Olson | A61F 2/2433 623/1.11 |
| 2012/0059458 A1 | 3/2012 | Buchbinder | |
| 2012/0323317 A1 | 12/2012 | Karapetian et al. | |
| 2013/0123910 A1 | 5/2013 | Cartledge | |
| 2013/0231735 A1* | 9/2013 | Deem | A61F 2/243 623/2.11 |
| 2013/0261737 A1* | 10/2013 | Costello | A61F 2/2418 623/2.11 |
| 2013/0304197 A1 | 11/2013 | Buchbinder | |
| 2014/0005778 A1 | 1/2014 | Buchbinder | |
| 2014/0067048 A1 | 3/2014 | Chau et al. | |
| 2014/0180401 A1 | 6/2014 | Quill et al. | |
| 2014/0200662 A1 | 7/2014 | Eftel et al. | |
| 2014/0222136 A1 | 8/2014 | Geist et al. | |
| 2014/0222142 A1* | 8/2014 | Kovalsky | A61F 2/2418 623/2.17 |
| 2014/0257467 A1* | 9/2014 | Lane | A61F 2/2418 623/2.11 |
| 2014/0288639 A1 | 9/2014 | Gainor | |
| 2014/0324164 A1* | 10/2014 | Gross | A61F 2/2436 623/2.37 |
| 2015/0257878 A1 | 9/2015 | Lane et al. | |
| 2016/0038280 A1 | 2/2016 | Morriss | |
| 2016/0199177 A1 | 7/2016 | Spence | |
| 2016/0270911 A1 | 9/2016 | Ganesan et al. | |
| 2016/0310268 A1 | 10/2016 | Oba | |
| 2017/0056163 A1 | 3/2017 | Tayeb et al. | |
| 2017/0056169 A1 | 3/2017 | Johnson et al. | |
| 2017/0128199 A1 | 5/2017 | Gurovich et al. | |
| 2017/0189177 A1 | 7/2017 | Schweich, Jr. et al. | |
| 2017/0216023 A1 | 8/2017 | Lane et al. | |
| 2017/0266003 A1* | 9/2017 | Hammer | A61F 2/2418 |
| 2017/0312078 A1 | 11/2017 | Krivoruchko | |
| 2017/0325954 A1 | 11/2017 | Perszyk | |
| 2017/0348098 A1 | 12/2017 | Rowe et al. | |
| 2017/0360426 A1 | 12/2017 | Hacohen et al. | |
| 2017/0367822 A1 | 12/2017 | Naor et al. | |
| 2018/0000580 A1 | 1/2018 | Wallace et al. | |
| 2018/0028311 A1 | 1/2018 | Hacohen et al. | |
| 2018/0049873 A1 | 2/2018 | Manash et al. | |
| 2018/0110622 A1 | 4/2018 | Gregg et al. | |
| 2018/0153685 A1 | 6/2018 | Costello | |
| 2018/0206986 A1 | 7/2018 | Noe et al. | |
| 2018/0221147 A1 | 8/2018 | Ganesan et al. | |
| 2018/0256322 A1 | 9/2018 | Zhang et al. | |
| 2018/0325662 A1 | 11/2018 | Modine | |
| 2018/0338832 A1 | 11/2018 | Ganesan et al. | |
| 2019/0008640 A1 | 1/2019 | Cooper et al. | |
| 2019/0029814 A1 | 1/2019 | Schweich, Jr. et al. | |
| 2019/0029817 A1 | 1/2019 | Seguin | |

FOREIGN PATENT DOCUMENTS

| | | |
|---|---|---|
| CN | 101374478 | 2/2009 |
| CN | 101641061 | 2/2010 |
| CN | 102119013 | 7/2011 |
| CN | 102438546 | 5/2012 |
| CN | 102639179 | 8/2012 |
| CN | 102665612 | 9/2012 |
| CN | 103037814 | 4/2013 |
| CN | 103889369 | 6/2014 |
| CN | 103997990 | 8/2014 |
| CN | 104188737 | 12/2014 |
| CN | 104334119 | 2/2015 |
| CN | 105101911 | 11/2015 |
| EP | 3060173 | 8/2016 |
| EP | 3294221 | 3/2018 |
| JP | 2013-539395 | 10/2013 |
| JP | 2014-532457 | 12/2014 |
| JP | 2015-519187 | 7/2015 |
| WO | WO 00/47139 | 8/2000 |
| WO | WO 2004/91454 | 10/2004 |
| WO | WO 2009/045338 | 4/2009 |
| WO | WO 2012/031141 | 3/2012 |
| WO | WO 2013/021375 | 2/2013 |
| WO | WO 2013/059747 | 4/2013 |
| WO | WO 2013/114214 | 8/2013 |
| WO | WO 2014/011888 | 1/2014 |
| WO | WO 2015/057735 | 4/2014 |
| WO | WO 2014/14493 7 | 9/2014 |
| WO | WO 2016/016899 | 2/2016 |
| WO | WO 2018/187805 | 10/2018 |

\* cited by examiner

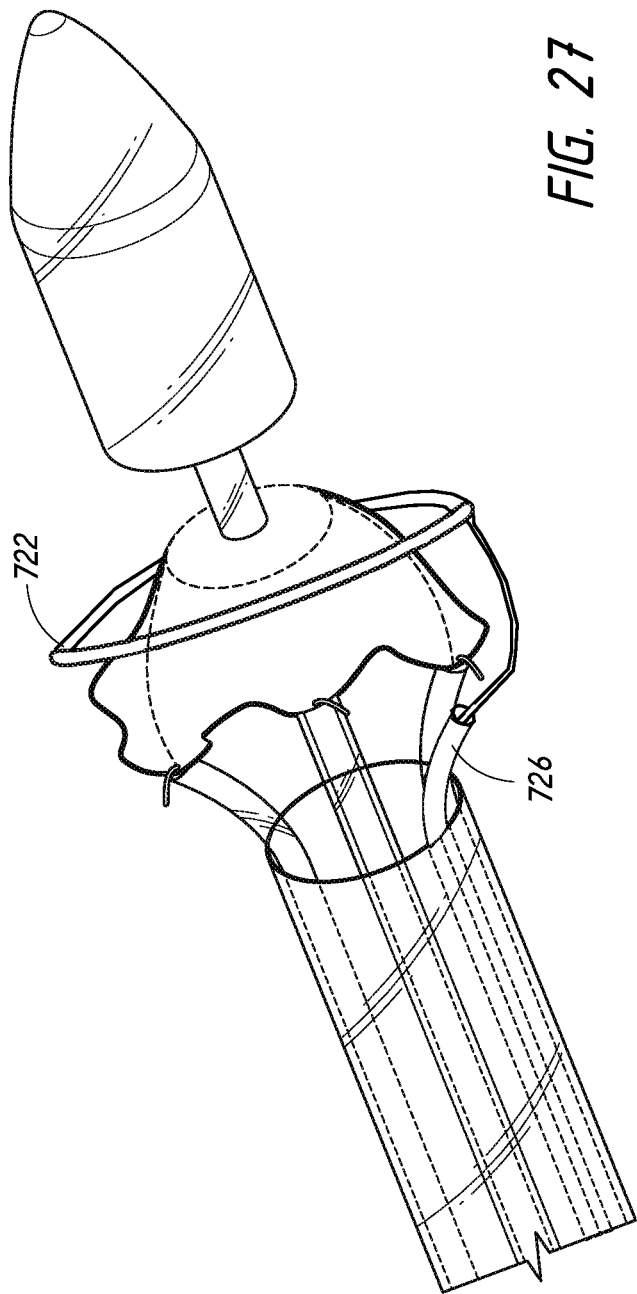

MITRAL VALVE PROSTHESIS IMPLANTATION

CROSS-REFERENCE TO RELATED APPLICATIONS

This application is a continuation of U.S. application Ser. No. 15/344,486, filed Nov. 4, 2016, which claims the benefit of U.S. Provisional Application No. 62/252,390, filed Nov. 6, 2015, the entireties of each of which is incorporated herein by reference.

BACKGROUND

Field of the Inventions

The present disclosure relates to devices and methods for the percutaneous delivery and implantation of a cardiac valve prosthesis. The valve prosthesis can be delivered in a collapsed state within a sheath to the valve and released in situ.

Description of the Related Art

The mitral valve, also referred to as the left atrioventricular or bicuspid valve, has two primary leaflets, the anterior and posterior leaflets, and a subvalvular apparatus consisting of chordae tendineae attaching to the anterior and posterior papillary muscles of the left ventricle. A healthy mitral valve allows blood to flow unimpeded from the left atrium to the left ventricle during diastole and prevents regurgitation during systole. Normal mitral valve function depends not only on the integrity of the underlying valvular structure, but on the adjacent myocardium as well.

There are three types of mitral valve disease: mitral stenosis, mitral regurgitation and mitral valve prolapse. Mitral stenosis refers to the narrowing of the mitral valve orifice, thereby impairing the filling of the left ventricle in diastole. Mitral regurgitation is leakage of blood from the left ventricle backwards into the left atrium during systole. Mitral valve prolapse is the systolic billowing of one or both mitral leaflets into the left atrium during systole.

If the mitral valve becomes diseased or damaged, it may be surgically repaired to restore function. In many cases, however, the valve is too damaged to permit repair and the valve must be replaced with a prosthetic (artificial) valve. Currently open heart surgical repair and replacement of the mitral valve are the two main options to treat mitral regurgitation. Open chest mitral valve replacement has been used to treat patients with mitral valve regurgitation since the 1960s. The patient's diseased mitral valve is replaced by either a mechanical or a bioprosthetic valve. Open heart surgical procedure needs surgical opening of the thorax, the initiation of extra-corporeal circulation with a heart-lung machine, stopping and opening the heart, excision and replacement of the diseased valve, and restarting of the heart. While valve replacement surgery typically carries a 1-4% mortality risk in otherwise healthy persons, a significantly higher morbidity is associated to the procedure largely due to the necessity for extra-corporeal circulation. Further, open-heart surgery is often poorly tolerated in elderly patients.

Percutaneous approaches to mitral valve repair have been developed to reduce the clinical disadvantages of the open-heart procedures. In some percutaneous techniques, a prosthesis is advanced in a catheter through the patient's vasculature to the vicinity of the mitral valve. These transcatheter techniques include transfemoral delivery in which a device is implanted through the femoral artery and transapcial in which implantation is through a small incision in the chest and through the apex of the heart. These percutaneous techniques are attractive alternatives to conventional surgical treatment because they do not require open-heart surgery or extracorporeal circulation, and can be used in a closed and beating heart. The treatment is potentially less morbid and can be applied to a wider range of patients including those with less severe valvular dysfunction.

Transcatheter or percutaneous mitral valve replacement is particularly demanding technically, primarily due to the complex mitral valve and subvalvular anatomy, the absence well-structured implant site, the often multifactorial coinciding etiologies in mitral valve diseases, and the frequent occurrence of mitral valve annulus prolapse. Current techniques of transcatheter mitral valve repair still have a high percentage of procedural failures or complications. Their long-term efficiency is relatively low in particular because of a high rate of recurrent mitral regurgitation. Significant challenges therefore remain for transcatheter mitral valve replacement and consequently and despite a particularly invasive side, surgical repair is the treatment usually recommended for diseases of the mitral valve.

The foregoing examples of the related art and limitations related therewith are intended to be illustrative and not exclusive. Other limitations of the related art will become apparent to those of skill in the art upon a reading of the specification and a study of the drawings.

SUMMARY

The following aspects and embodiments thereof described and illustrated below are meant to be exemplary and illustrative, not limiting in scope.

In some embodiments, a valve prosthesis can comprise an anchoring element. The anchoring element can comprise at least one engagement member. Optionally, the anchoring element can comprise at least one lobe or at least one hook.

Optionally, the valve prosthesis can also comprise a valve component. The valve component can comprise a valve frame that can be radially expandable and comprise a plurality of flexible prosthetic leaflets attached thereto.

In some embodiments, the anchoring element can be flexibly connected to the valve component such that the anchoring element can move relative to the valve component along the axis along an inflow-outflow direction (e.g., along a longitudinal axis).

The anchoring element can be flexibly connected to the valve component through a coupler component which can provide a pre-defined maximum distance by which the anchoring element and the valve component may be separated along the longitudinal axis and the length of overlap between the anchoring element and the valve component along the longitudinal axis.

In some embodiments, the valve component can comprise a plurality of prosthetic valve leaflets attached to thereto the valve frame. In some embodiments, the valve frame can be comprised of a shape memory metal. In some embodiments, the valve frame has a circular cross-section when in an expanded configuration.

In some embodiments, the anchoring element can comprise a shape memory wire and the anchoring element can expand radially from a collapsed configuration to an expanded configuration. In some embodiments, the shape memory wire has a diameter ranging from about 0.5 mm to about 3 mm, about 0.5 mm to 2 mm, 1 mm to 3 mm, or 1 mm to 2 mm.

In some embodiments, the anchoring element can comprise an anterior lobe and a posterior lobe. In some embodiments, the anchoring element has a longitudinal axis and a radial axis orthogonal to the longitudinal axis. In the expanded configuration, the anterior lobe can extend upward from the radial at an angle ranging from about 70 degrees to about 90 degrees, about 80 degrees to about 90 degrees, about 75 degrees to about 85 degrees, or about 80 degrees to about 85 degrees. The posterior lobe can extend downward from the radial axis at an angle ranging from about 30 degrees to about 45 degrees, about 35 degrees to about 45 degrees, or about 35 degrees to about 40 degrees. In some embodiments, the anterior lobe in an expanded configuration in the native valve annulus can exert pressure against the anterior wall of the left atrium and the posterior lobe in an expanded configuration in the native valve annulus can exert pressure against the posterior wall of the left atrium.

In some embodiments, the anchoring element can comprise 2, 3, 4, 5, 6, 7, 8, 9, 10, or between 2-10, 2-8, 3-20, 3-20, 3-8, 3-5, or 3-4 lobes.

In some embodiments, the anchoring element can comprise 2, 3, 4, 5, 6, 7, 8, 9, 10, or between 2-20, 2-10, 2-8, 3-20, 3-20, 3-8, 3-5, or 3-4 engagement members, such as hooks. In some embodiments, the number of engagement members or hooks can equal the number of lobes in the anchoring element.

In some embodiments, the anchoring element can comprise an upper support and a lower support. The upper and lower supports can be coupled together by a flexible connector. The flexible connector can comprise a tubular skirt that can provide a seal and prevent regurgitation or leakage around the valve prosthesis.

Optionally, the upper support of the anchoring element can form a shape that permits the upper support to approximate the shape of a native mitral valve annulus.

In some embodiments, the upper support of the anchoring element can comprise a first hook positioned between the anterior lobe and the posterior lobe. In some embodiments, the anchoring element can comprise a second hook that can be positioned between the anterior lobe and the posterior lobe and along the radial axis that can be opposite the first hook.

In some embodiments, the at least two engagement members can comprise the first hook and the second hook, and the first hook and the second hook can be separated by a distance of between about 30 mm to about 90 mm. In some embodiments, the distance can be approximately equal to the distance between anterolateral commissure and posteromedial commissure of a heart of the patient who is the recipient of the valve prosthesis.

In some embodiments, the anchoring element can comprise a third hook that that can be positioned midway along the posterior lobe. In some embodiments, an arm portion of each hook in an expanded configuration extends approximately downward from the radial axis of the anchoring element.

In some embodiments, the valve prosthesis can further comprise a coupler component that interconnects the anchoring element with the valve component. The distance which the anchoring element can move relative to the valve component can be determined by the length of a coupler component. In some embodiments, the coupler component can be fixed to the valve component. In some embodiments, the coupler component can be fixed to the anchoring element.

In some embodiments, the coupler component can comprise a fabric sheet, a suture, and/or a tubular cloth. Optionally, the fabric sheet can be in a tubular configuration. In some embodiments, a first end of the fabric sheet can be attached to the anchoring element and a second end of the fabric sheet can be attached to the valve component. In some embodiments, the fabric sheet can be continuous and extends from the first end attached the anchoring element to the second end attached to the valve component. In some embodiments, the fabric sheet can cover about one-half to one-third of the length of the valve component. In some embodiments, the fabric sheet covers about one-third to two-thirds, one-quarter to two-quarters, or the full length of the valve component. In some embodiments, the fabric sheet allows some blood flow through the sheet.

In some embodiments, the coupler component can be comprised of one or more sutures or thread-like elements, wherein a first end of the one or more sutures or thread-like elements can be attached to the anchoring element and a second end of the one or more sutures or thread-like elements can be attached to the valve component.

In some embodiments, the coupler component can have a length 1 which allows the anchoring element to be serially displaced from the valve component when both the anchoring element and the valve component are in a collapsed configuration.

For example, some embodiments of the valve prosthesis can be based on the anatomy of the mitral annulus. The annulus has a saddle-shaped ring of tissue that surrounds the two leaflets of the mitral valve. An upper support of the anchoring element can comprise a D-shaped nitinol ring. The D-shape of the upper support can allow the anchoring element to conform to the annulus with the flat face of the "D" sitting adjacent to the aortic mitral curtain. The lower support can comprise a nitinol ring having three hooks extending from strategic positions matching the native valve leaflets. Two of the hooks can be positioned to latch in the commissures (on the ventricular side of the heart) and a third hook can catch the P2 scallop of the posterior leaflet (also on the ventricular side). Further, a flexible connector or tubular skirt can extend between the upper and lower supports. Furthermore, a coupler component can interconnect the anchoring element with the valve component.

Accordingly, some embodiments can advantageously provide a seal for the prosthetic valve. For example, the skirt of some embodiments can provide a seal for the prosthetic valve without introducing a left ventricular outflow tract obstruction. The skirt can also prevent paravalvular leakage that can occur, in particular, at commissure locations. The skirt can also aid in ingrowth to enhance sealing.

In some embodiments, a valve prosthesis delivery system can be provided. The delivery system can comprise a first sheath and a second sheath. The first sheath and the second sheath can be positioned longitudinally adjacent to one another or in an end-to-end abutting relationship along the longitudinal axis. The delivery system can optionally comprise anchor controls, graspers, or anchor control sleeves that can engage with at least a portion of a valve prosthesis supported by or carried by the delivery system.

In accordance with some embodiments, the valve prosthesis can be delivered to the native mitral valve annulus in a collapsed configuration in which the valve component and anchoring element are serially (or longitudinally spaced relative to each other), rather than concentrically positioned relative to one another, thereby minimizing the diameter of the valve prosthesis and therefore, minimizing the diameter of the delivery system during delivery.

In some embodiments, the delivery system can further comprise a control unit, wherein the control unit can be used by a surgeon or medical physician to independently manipulate at least lateral or rotational movements of at least the valve prosthesis, anchor controls, the first sheath, and/or the second sheath.

In some embodiments, the first sheath can enclose the valve component, and the second sheath can enclose the anchoring element. The first sheath can be adjacent to and distal to the second sheath.

However, in some embodiments, the first sheath can enclose the anchoring element, and the second sheath can enclose the anchoring element. The first sheath can be adjacent to and distal to the second sheath. In some embodiments, the valve component can be flexibly connected to the anchoring element.

In some embodiments, the number of anchor controls can be equal to the number of engagement members or hooks of the anchoring element. Further, the proximal end of each of the anchor controls can be coupled to the control unit and a distal end of each of the anchor controls can be releasably coupled to one of the hooks.

In some embodiments, the delivery system can further comprise a first sheath shaft connected at its distal end to the first sheath and at its proximal end to the control unit.

In some embodiments, the delivery system can further comprise a counter nose cone, wherein the counter nose cone can be positioned between the first and second sheaths. For example, the counter nose cone can maintain the position of the valve component within the first sheath or the second sheath prior to full release of the valve prosthesis.

In some embodiments, a method can be provided for transapical delivery of a mitral valve prosthesis comprising use of the delivery system as described above.

In some embodiments, the method can comprise inserting the distal end of the delivery system into the left ventricle and advancing the first sheath through the mitral valve into the left atrium. The second sheath can be moved in a proximal direction such that an upper support of the anchoring element expands radially to contact the anterior and posterior surfaces of the left atrium and a lower support of the anchoring element expands radially to contact papillae and/or the left ventricle wall. The anchoring element can then be moved in a proximal direction until the lower support and the upper support are on opposite sides of the native mitral valve annulus. Thereafter, the first sheath can be moved in a distal direction while holding the valve component stationary to release the valve component. The valve component can expand in a radial direction within the anchoring element. Thereafter, the delivery device can be removed by pulling the first and second sheaths in a proximal direction.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 20A-21B illustrate optional anchoring elements, according to some embodiments.

FIG. 27 illustrates aspects of optional methods for delivering a check valve, according to some embodiments.

DETAILED DESCRIPTION

Figure 1:
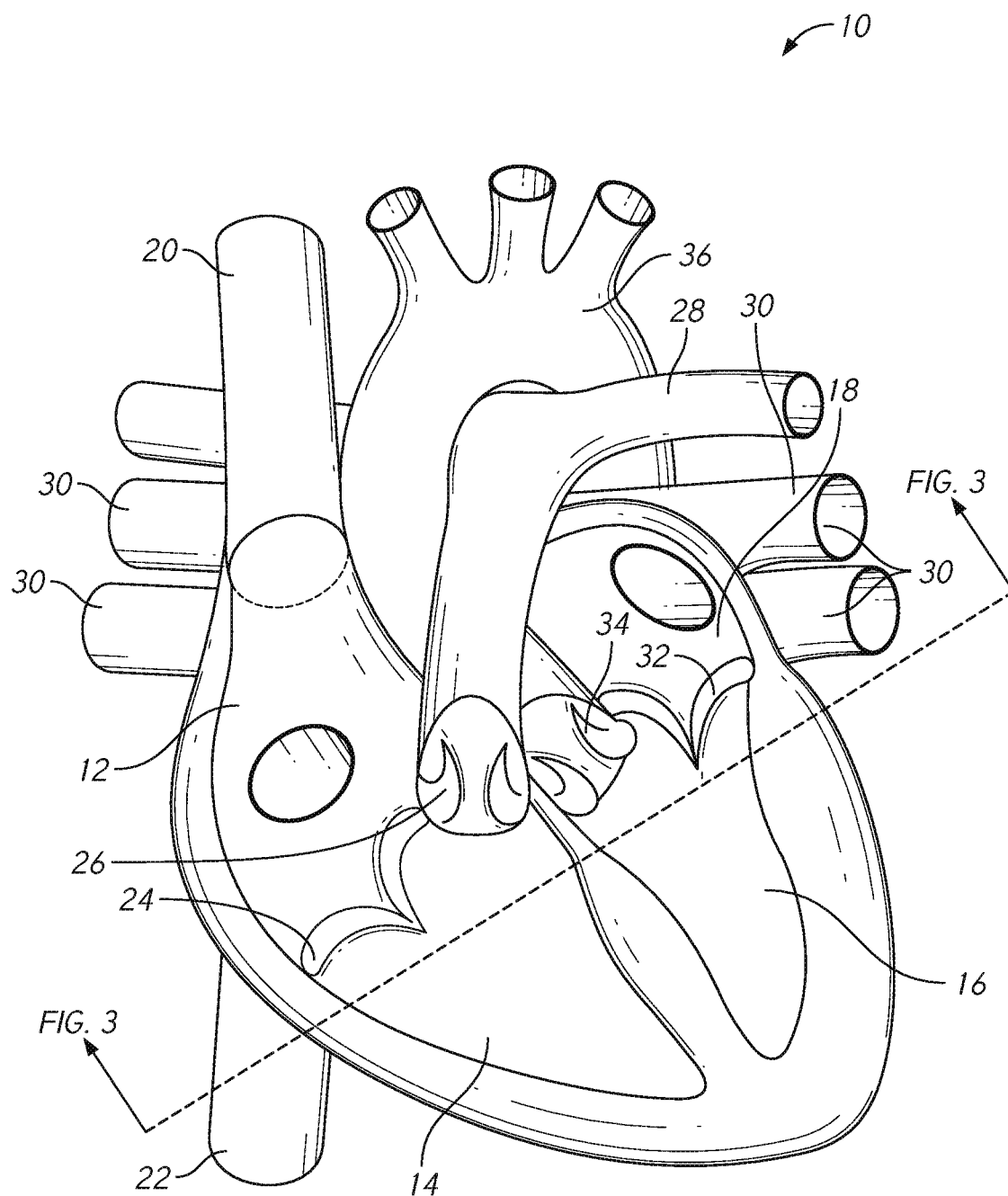
FIG. 1 is a cross-sectional view of a heart, illustrating aspects of the heart.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present disclosure sets forth specific details of various embodiments, it will be appreciated that the description is illustrative only and should not be construed in any way as limiting. Additionally, it is contemplated that although particular embodiments of the present disclosure may be disclosed or shown in the context of mitral valve prostheses, such embodiments may be used in other cardiac valve prosthesis applications. Furthermore, various applications of such embodiments and modifications thereto, which may occur to those who are skilled in the art, are also encompassed by the general concepts described herein.

As with all cardiac valves, a healthy mitral valve will open to allow blood flow and close to prevent backflow of blood. However, disease and dysfunction of the valve can result in regurgitation or decreased blood flow. In such cases, a replacement mitral valve prosthesis must be used to perform the functions of a healthy mitral valve.

However, there are numerous challenges in providing a replacement mitral valve prosthesis. For example, in order to overcome the problem of regurgitation or decreased blood flow, a suitable replacement mitral valve prosthesis must provide an acceptable seal against the native mitral valve tissue when positioned and released against the native mitral valve and the mitral annulus. Further, the architecture of the mitral annulus, including the aortic-mitral curtain, also creates a challenge in the design of a mitral valve prosthesis. Indeed, the mitral valve prosthesis must conform to the unique anatomical structure of the mitral valve and remain anchored in the presence of the continuous contractions of a functioning heart.

The present disclosure describes devices and methods for implanting a mitral valve prosthesis using a minimally invasive surgical technique. The devices accommodate the complex structure of the mitral valve to ensure that the implanted prosthesis is properly positioned and securely maintained in place after implantation. Further, some embodiments also provide a mitral valve prosthesis delivery system that can comprise a delivery device and a mitral valve prosthesis.

The mitral valve prosthesis can comprise an anchoring element and a valve component coupled to the anchoring element. The valve component can have a plurality of prosthetic valve leaflets attached to an internal surface thereof that can mimic the function of a native mitral valve. The valve component and anchoring element can have a compact configuration for delivery to a diseased valve, and an unfolded or expanded configuration upon release and implantation in the diseased valve annulus.

Moreover, in some embodiments, the valve component and the anchoring element can be positioned within the delivery system in a serial configuration rather than overlapping, thereby reducing the diameter of the valve component during delivery.

Further, in some embodiments, the valve component can be flexibly coupled to the anchoring element to provide efficient positioning of both the anchoring element and the valve component. For example, the valve component and the anchoring element can be connected by a flexible element such that prior to releasing and expanding the valve component in the heart or native valve annulus, the valve component and the anchoring element can be longitudinally or rotationally displaced relative to one another. Further, the valve component and the anchoring element can unfolded or expand from a compact state to an expanded state, and in some embodiments, independently of each other.

Cardiac Valve Anatomy and Valve Replacement

FIG. 1 illustrates a diagrammatic cross-sectional view of a human heart 10. The heart 10 can comprise a right atrium 12, a right ventricle 14, a left ventricle 16, and a left atrium 18. Oxygen-depleted blood enters the right atrium 12 through the superior and inferior vena cava 20, 22. The oxygen-depleted blood is pumped from the right atrium, through a tricuspid valve 24, which separates the right atrium 12 from the right ventricle 14, and into the right ventricle 14. The right ventricle 14 then pumps the oxygen-depleted blood through a pulmonary valve 26 and into pulmonary arteries 28 that direct the oxygen-depleted blood to the lungs for oxygen transfer to the oxygen-depleted blood. Thereafter, oxygen-rich blood is transported from the lungs through pulmonary veins 30 to the left atrium 18. The oxygen-rich blood is pumped from the left atrium 18 through a mitral valve 32 and into the left ventricle 16. The left ventricle 16 then pumps the oxygen-rich blood through an aortic valve 34 and into the aorta 36. The oxygen-rich blood is carried by the aorta to a series of arteries that transport the blood to various organs in the body.

The mitral valve 32, also known as the bicuspid valve or left atrioventricular valve, opens and closes to control the flow of the oxygen-rich blood from the heart. When the left ventricle 16 relaxes, blood from the left atrium 18 fills the left ventricle 16. When the left ventricle 16 contracts, the increase in pressure within the ventricle 16 causes the mitral valve 32 to close, preventing blood from leaking to the left atrium 18 and assuring that all of the blood leaving the left ventricle 16 is ejected through the aortic valve 34 into the aorta 36 and to the body.

Figure 2:
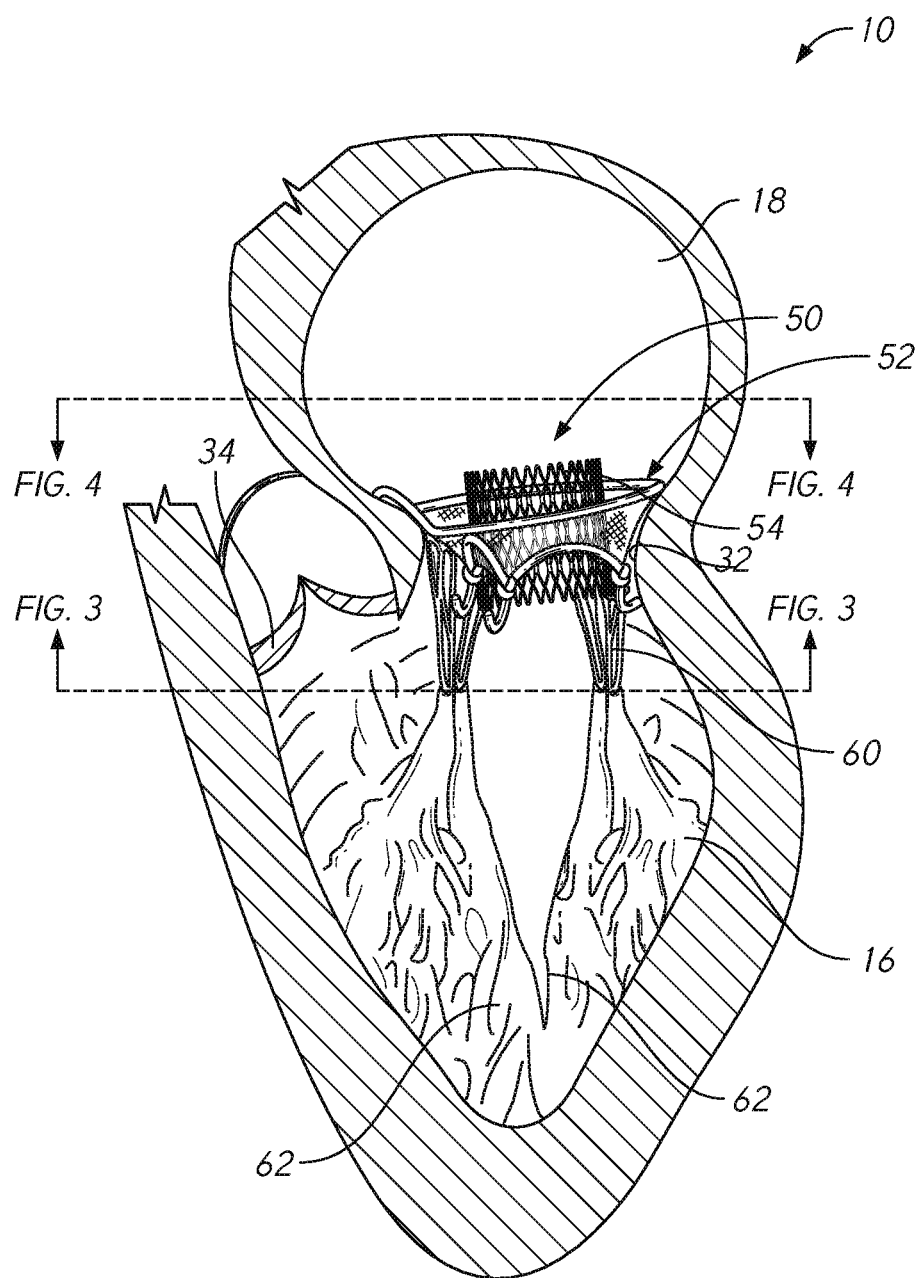
FIG. 2 is a side cross-sectional view of a mitral valve prosthesis implanted in the heart, according to some embodiments.
Figure 3:
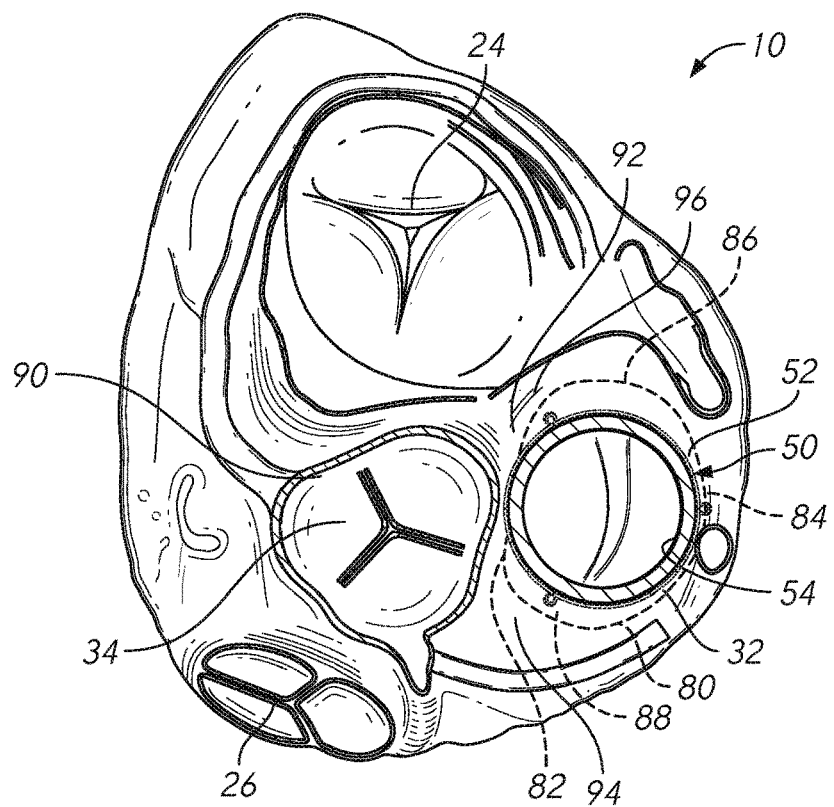
FIG. 3 is a bottom cross-sectional view of the mitral valve prosthesis of FIG. 2, implanted in the heart, according to some embodiments.
Figure 4:
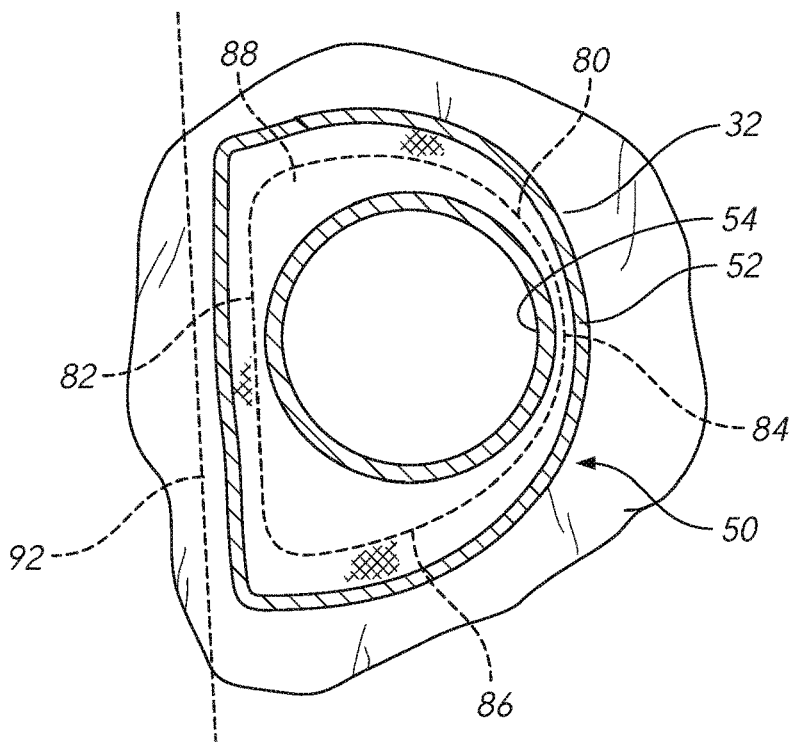
FIG. 4 is a top cross-sectional view of the mitral valve prosthesis of FIG. 2, implanted in the heart, according to some embodiments.

FIGS. 2-4 illustrate partial cross-sectional views of the heart 10 having a mitral valve prosthesis 50 implanted therein to replace the native mitral valve 32. FIG. 2 is an enlarged view to illustrate the mitral valve 32 of the heart 10, while FIG. 3 illustrates a bottom or ventricular view across a valvular plane of the heart 10 and FIG. 4 illustrates a top or atrial view of the mitral valve 32. In accordance with some embodiments, the mitral valve prosthesis 50 can comprise an anchoring element 52 and a valve component 54. The anchoring element 52 can anchor to (or engage with) the natural architecture of the native mitral valve 32 and surrounding tissue, and the valve component 54 can comprise a plurality of leaflets that function to provide one-way flow of blood through the mitral valve 32.

For example, on the ventricular side (illustrated in FIGS. 2 and 3), the anchoring element 52 can engage with chordae tendineae 60 that extend downwardly from the mitral valve 32 to anchor on lateral and medial papillary muscles 62. Further, in some embodiments, the anchoring element 52 can engage with a mitral annulus 80 of the mitral valve 32. The mitral annulus 80 is a fibrotic ring that has an anterior part and a posterior part. The mitral annulus 80 extends around a perimeter of the mitral valve 32. The mitral annulus 80 is a three-dimensional saddle-shaped structure (hyperbolic paraboloid) with highest points formed by an anterior annulus 82 and a posterior annulus 84, and nadirs at posterolateral and anteromedial commissures 86, 88. The mitral annulus 80 is approximately adjacent to an aortic valve annulus 90. Between the mitral annulus 80 and the aortic valve annulus 90 is an aortic-mitral curtain 92, which is a fibrous structure that connects the anterior annulus 82 of the mitral annulus 80 intimately with the aortic valve annulus 90 and ends at both lateral sites (adjacent the posterolateral and anteromedial commissures 86, 88) of the mitral valve 32 to form the left and right fibrous trigones 94, 96.

Mitral Valve Prostheses

Figure 5:
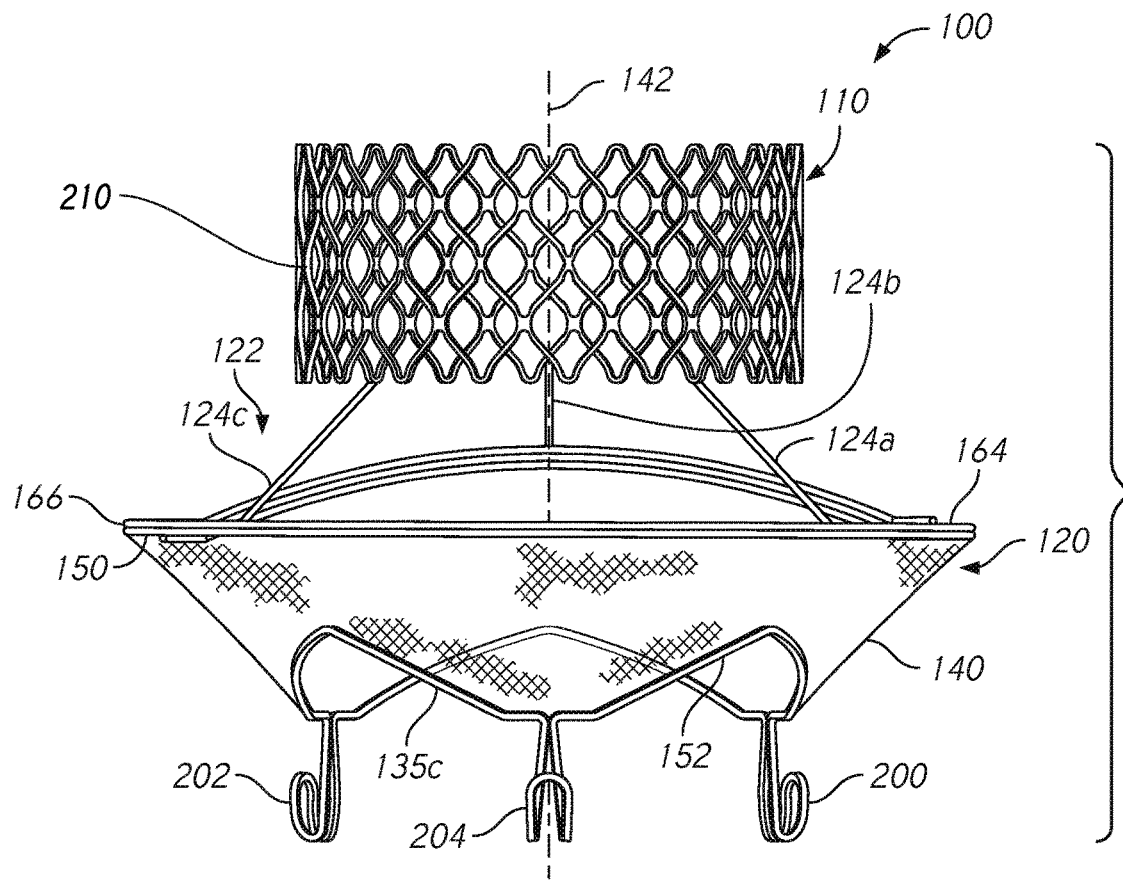
FIG. 5 shows an embodiment of the valve component and the anchoring element of a mitral valve prosthesis in a non-engaged configuration, according to some embodiments.

Referring now to FIGS. 5-8B, a mitral valve prosthesis 100 and components thereof are shown in various configurations. The mitral valve prosthesis 100 can comprise a valve component 110 and an anchoring element 120 to which the valve component 110 is coupled. In some embodiments, the valve component 110 can be flexibly coupled to the anchoring element 120 via a coupler component 122 that is attached at one end to the anchoring element 120 and at the other end to the valve component 110. The coupler component 122 is shown in FIG. 5 as a plurality of threads 124a, 124b, 124c. As discussed herein, the flexible interconnection of the valve component 110 to the anchoring element 120 can provide advantages in delivering, placing, and ensuring proper function of the mitral valve prosthesis 100.

FIG. 5 also illustrates that in some embodiments, the anchoring element 120 can comprise one or more supports, loop structures, wire components that are interconnected with each other by at least one flexible connector 140. The flexible connector 140 can comprise at least one sheet, tubular member, or strands of material that are couple two or more components of the anchoring element 120. For example, the flexible connector 140 illustrated in FIG. 5 can comprise a tubular skirt structure that is coupled at an upper portion to an upper support 150 of the anchoring element 120 and at a lower end to a lower support 152 of the anchoring element 120. Additional details on the upper and lower supports 150, 152 are discussed further below.

FIG. 5 illustrates the valve prosthesis 100 in a decoupled configuration, in which the valve component 110 is not longitudinally overlapping the anchoring element 120, but instead is longitudinally spaced apart from and adjacent to the anchoring element 120, along a central or longitudinal axis 142 of the valve prosthesis 100. The decoupled configuration is shown to illustrate that the anchoring element 120 can be placed within the mitral valve, i.e., within the heart between the left ventricle and the left atrium, and secured in place before the valve component 110 is released and positioned within the mitral valve. Additionally, as discussed herein, coupler component 122 can facilitate engagement and alignment between the valve component 110 and the anchoring element 120, which can allow the valve component 110 and the anchoring element 120 to be independently unfolded or expanded, positioned relative to the structure of the heart, and released. Accordingly, as discussed herein, various advantages can be achieved during the surgical procedure.

Figure 6:
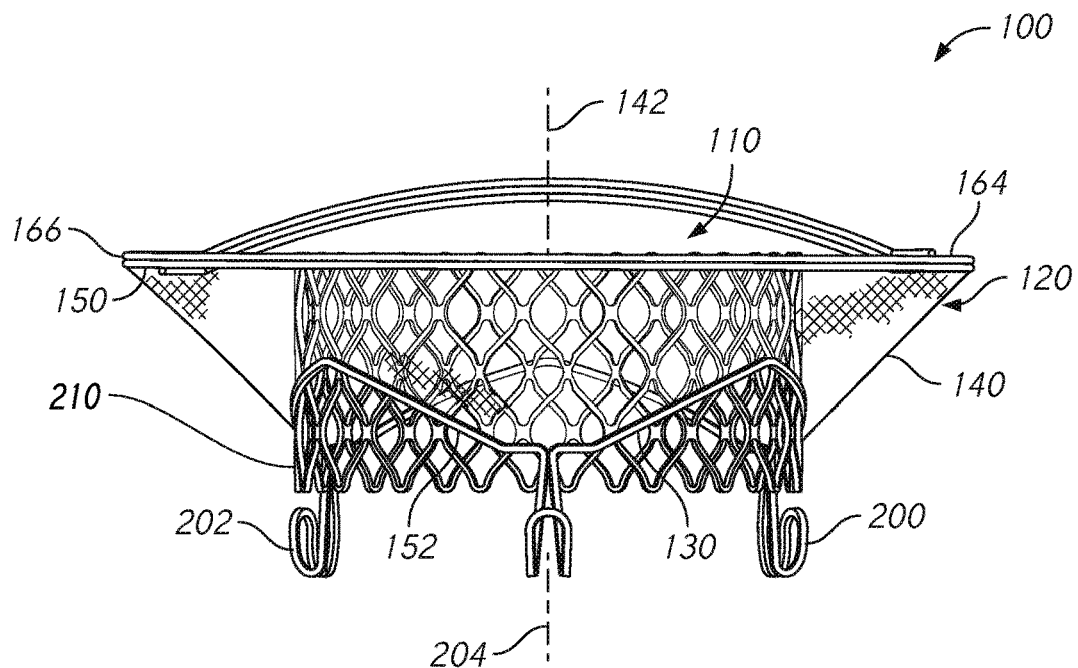
FIG. 6 shows an embodiment of a mitral valve prosthesis in a configuration when released in a mitral valve annulus, according to some embodiments.

FIG. 6 illustrates the mitral valve prosthesis 100 in an assembled configuration in which the valve component 110 is positioned and expanded within the anchoring element 120, as would be the configuration after mitral valve prosthesis 100 is implanted in the native valve annulus of a patient. After the anchoring element 120 has been expanded and positioned within the mitral valve, the valve component 110 can be positioned and expanded within the anchoring element 120. In some embodiments, during implantation of the valve prosthesis 100, the valve component 110 is expanded only after it has been placed in a position that is at least partially longitudinally overlapping and/or concentric with the anchoring element 120. Thus, the anchoring element 120 can be coupled to the valve component 110 such that the valve component 110 can move from a position that is longitudinally spaced apart from or serially displaced from the anchoring element 120 to a position at least partially longitudinally overlapping or fully concentric to the anchoring element 120.

Anchoring Elements

As noted above, the anchoring element 120 can comprise various components. For example, the anchoring element 120 can comprise upper and lower supports 150, 152 that are coupled together via the flexible connector 140. The upper support 150, the flexible connector 140, and the lower support 152 can each provide advantages and benefits to the function and adaptability of the mitral valve prosthesis 100.

Figure 7A:
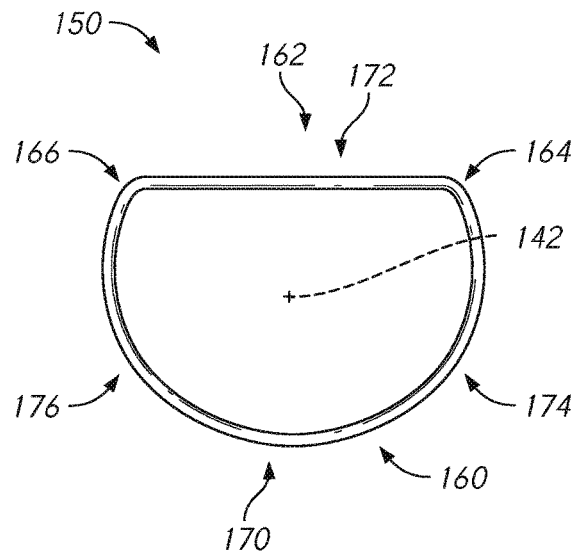
FIGS. 7A and 7B illustrate top and perspective views of a valve component of a mitral valve prosthesis, according to some embodiments.
Figure 7B:
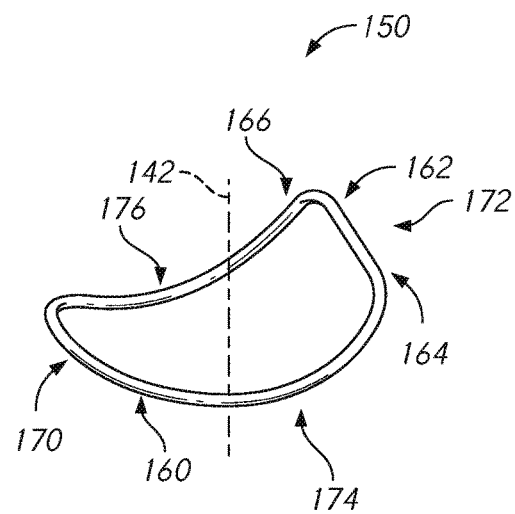
Figure 8A:
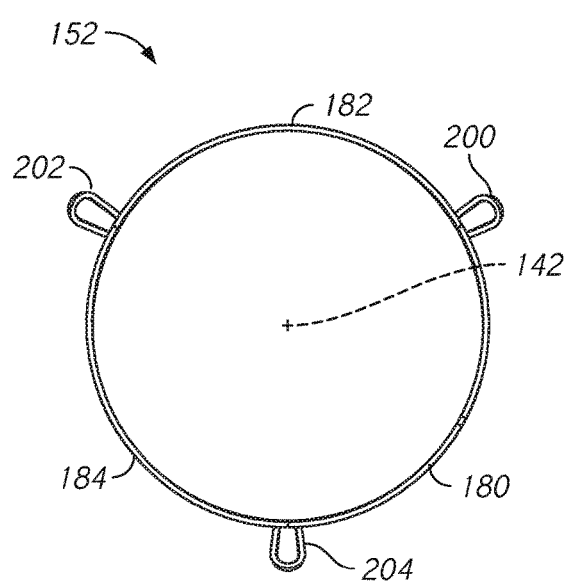
FIGS. 8A and 8B illustrate top and perspective views of an anchoring element of a mitral valve prosthesis, according to some embodiments.
Figure 8B:
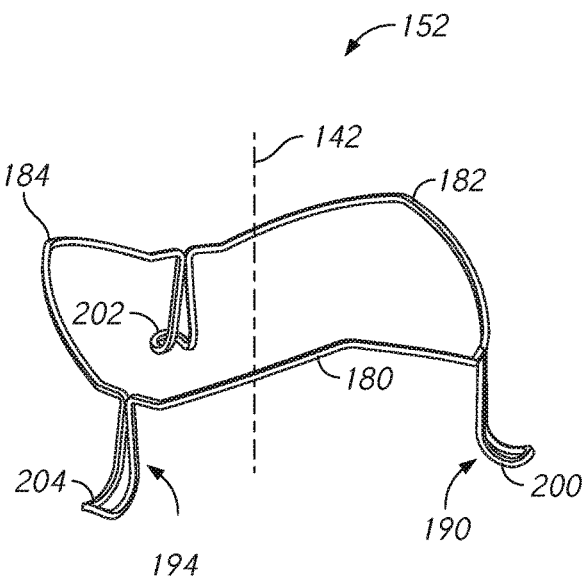

Referring now to FIGS. 7A and 7B, the upper support 150 can comprise a structure that, when seen in a two-dimensional top view, optionally has a "D" shape (or of a ring having one or more straight sides). Thus, when seen in a top view, the upper support 150 can comprise a posterior portion 160 that comprises a semicircular shape and a straight anterior portion 162, coupled to the posterior portion 160. In geometric terms, the posterior portion 160 can comprise a rounded portion of a ring while the anterior portion 162 comprises a chord extending between ends of the rounded portion of the ring (opposing ends 164, 166 of the posterior portion 160) to create a flat or straight side of the ring.

For example, the upper support 150 can comprise a closed D-ring that has a released, deployed, or unfolded condition that can have an approximately oval or spherical shape. The radius of the D-ring, when unfolded, can be sufficient to exert pressure against tissue in the left atrium and adjacent to the native mitral valve annulus. The D-ring can take on a saddle shape to conform to a healthy native mitral valve annulus and the presence of the flattened portion of the D-ring accommodates the stiff structure of the aortic-mitral curtain.

Optionally, when unfolded, the posterior portion 160 of the upper support 150 can be substantially planar, i.e., extend within a first plane. Thus, the length of the upper support 150 extending between the opposing ends 164, 166 can lie in the first plane. There, the posterior portion 160 can comprise a have first radius of curvature.

Further, the anterior portion 162 of the upper support 150 can optionally bend out of the first plane, along an axis extending transverse relative to the central axis 142 of the valve prosthesis 100. For example, the anterior portion 162 can bow upwardly in an arcuate path between the opposing ends 164, 166. The arcuate path of the anterior portion 162 can comprise a segment of a circle or have a second radius of curvature. In some embodiments, the anterior portion 162 can extend and then arcuate path within a second plane, transverse to the first plane. For example, the second plane can extend at an angle of about 90 degrees relative to the second plane, an angle of between about 20 degrees and about 90 degrees relative to the second plane, at an angle of between about 30 degrees and about 80 degrees relative to the second plane, an angle of between about 40 degrees and about 70 degrees relative to the second plane, or an angle of between about 50 degrees and about 60 degrees relative to the second plane.

In some embodiments, the upper support 150 can comprise two, three or more engagement lobes that enable the upper support 150 to be seated against the mitral valve annulus when implanted in a heart. For example, in some embodiments, the upper support 150 can optionally comprise a three-dimensional, "saddle shape" when unfolded. For example, the upper support 150 can comprise a posterior lobe 170 and an anterior lobe 172. Further, the saddle shape of the upper support 150 can also comprise lateral lobes 174, 176, extending from the opposing ends 164, 166, between the posterior and anterior lobes 170, 172. When unfolded, as shown in FIG. 7B, the posterior and anterior lobes 170, 172 can bend upwardly relative to the lateral lobes 174, 176. Further, the lateral lobes 174, 176 can extend downward from the anterior lobe 172 at an angle of between about 25 degrees to about 55 degrees, an angle of between about 30 degrees to about 50 degrees, or an angle of between about 35 degrees to about 45 degrees relative to the native valve annulus 80 (e.g., relative to a mitral plane or a plane defined by points at the opposing ends 164, 166 and an apex of the posterior lobe 170). As a result, the anterior lobe 172 can be configured to push against the atrial wall next to the aorta, e.g., press against the aortic-mitral curtain, when implanted within a heart. Further, the lateral lobes 174, 176 can press against the ventricular wall adjacent to and posterior to the mitral valve annulus. Thus, when seen from a side view as in FIG. 7B, the upper support 150 can have a saddle shape that can be configured to conform to the native mitral valve structure.

The upper support 150 can thus be designed in shape to conform to the anatomy of the native mitral valve annulus 80 while the lower support 152 can, in some embodiments, anchor the anchoring element 120 within the mitral valve, i.e., within the heart between the left ventricle and the left atrium. The lower support 152 can comprise a wire frame body having a substantially round shape when seen in top view, as in FIG. 8A. The lower support 152 can comprise a plurality of lobes, e.g., two, three, four or more (shown as lobes 180, 182, 184 in FIG. 8B) that extend upwardly along the central axis 142 and a plurality of engagement sections, which can correspond to the number of lobes, e.g., two, three, four or more (shown as engagement sections 190, 192, 194 in FIGS. 8A and 8B) interposed between the lobes 180, 182, 184. Thus, according to some embodiments, the lower support 152 can comprise two, three or more lobes which, when the lower support 152 is in an expanded condition, extend such that each of the lobes exerts pressure against tissue in the left ventricle and adjacent to the native mitral valve annulus.

In accordance with some embodiments, the lower support 152 can comprise a plurality of engagement members 200, 202, 204, shown as hook structures, each extending from the lower support 152 at a respective one of the plurality of engagement sections 190, 192, 194. For example, the lower support 152 can comprise one or more engagement members positioned between two lobes. The term "hook" or "hook structure" is not intended to limit the shape or conformation of the hook element as used herein. The term "hook" or "hook structure" can refer to a structure that may be attached to the lower support 152 and which can radially expand to form a contact with or partially or fully insert into tissue present in the left ventricle and/or near the mitral valve. The hook can be fabricated from a shape memory metal or from any biocompatible material which remains intact in the heart for several years after implantation. Optionally, the engagement members 200, 202, 204 can be spaced apart from each other in a manner that allows the engagement members 200, 202, 204 to engage with specific aspects of the native mitral valve anatomy. Further, optionally, some or all of the engagement members or hooks can be covered with a fabric or suture material in order to reduce or eliminate risk of irritation and scar tissue buildup (see e.g., FIGS. 10A and 10B).

For example, in some embodiments, the lower support 152 can comprise three lobes and three hooks. A first hook 200 can be positioned between the first and second lobes 180, 182. The second hook 202 can be positioned opposite, spaced apart by the second lobe 182, from the first hook 200. Optionally included, the third hook 204 can be positioned midway between the first and second hooks 200, 202, between the first and third lobes 180, 184.

In accordance with some embodiments, each of the hooks 200, 202, 204 can extend below a plane of the lower support 152 and hook upwardly toward the valve annulus when expanded radially within the left ventricle of the heart, below the mitral valve annulus. For example, in some embodiments, the hooks can each engage with the mitral valve annulus, the papillae, and/or the ventricular wall to further anchor the lower support 152 within the heart between the left ventricle and the left atrium. Each hook can extend approximately distally such that when implanted in a native valve annulus, the free ends of the hooks point against the direction of blood flow. However, in some embodiments, the free ends of the hooks can point in the direction of blood flow. The hooks 200, 202, 204 can each comprise a self-expandable shape memory material and positioned to facilitate engagement of the hooks 200, 202, 204 with structures in the native mitral valve or left ventricle, including the left ventricular wall. In some embodiments, the lower support 152 can comprise more than three hooks, positioned to facilitate engagement of the hooks with structures in the native mitral valve or left ventricle, including the left ventricular wall. In some embodiments, as the hooks 200, 202, 204 of the lower support 152 can expand toward the chordae tendineae during valve prosthesis delivery, their design with shape memory metal allows them to expand and hook between and/or around the chordae tendineae. Optionally, the hooks of the lower support 152 can be pulled toward the chordae tendineae during valve prosthesis delivery, their design with shape memory metal allows them to expand and hook between and/or around the chordae tendineae.

The upper and lower supports 150, 152 can be fabricated from shape memory material (e.g., a nitinol wire) which is pliable enough to conform to native heart structures during implantation or during both rotational and lateral positioning of the upper and lower supports 150, 152. For example, the upper and lower supports 150, 152 can each comprise a self-expanding shape memory wire material. The wire material can have a diameter ranging from about X mm to Y mm. In some embodiments, the upper support 150 and/or the lower support 152 can comprise two or more windings, wrappings, or loops of wire material.

The upper and lower supports 150, 152 can be constructed to provide sufficient radial force and strength to prevent or minimize movement of the anchoring element 120, and in embodiments that use a valve component, which can be independently expanded and released into the native valve after implantation of the anchoring element 120. After delivery of the anchoring element 120 to the native valve annulus, both the upper support 150 can be unfolded to expand within the left atrium, after which the lower support 152 can be pulled into the left ventricle while the upper support 150 is maintained within the left atrium. After adjusting and releasing the lower support 152, the upper support 150 thus remains in the left atrium and the lower support 152 remains anchored in the left ventricle. The structure of the upper support 150 can impart a low profile to the anchoring element 120 so that when it is released and implanted within the left atrium, there is minimal or no obstruction to the openings of the pulmonary veins (ostia venarum pulmonalium), yet the anatomical configuration or shape of the upper support 150 in its unfolded or expanded condition can provide pressure against the atrial walls sufficient to facilitate anchoring of the anchoring element 120 within the native mitral valve annulus.

Referring again to FIGS. 5 and 6, the upper and lower supports 150, 152 can be coupled together by the flexible connector 140. In accordance with some embodiments, the flexible connector 140 can comprise one or more strands of material or tubular skirt structure. For example, FIGS. 5 and 6 illustrate that the flexible connector 140 can comprise a fabric or mesh material (shown as a "skirt" or tapered tubular member) that is coupled at an upper end portion to an upper support 150 of the anchoring element 120 and at a lower end to a lower support 152 of the anchoring element 120. The flexible connector 140 can provide a resilient, stretchable, flexible connection between the upper and lower supports 150, 152 that can facilitate alignment between aspects of the upper and lower supports 150, 152 and serve to mitigate or prevent paravalvular leakage after completion of the implant procedure. In some embodiments, the flexible connector 140 can comprise a material including, but not limited to, elastomeric fabrics, stainless steel alloys, shape memory alloys, superelastic alloys, knit fabrics, and/or sutures.

In some embodiments, the use of the flexible connector 140 provides additional benefits in that it permits the use of separate upper and lower supports 150, 152 that can be independently released and expanded within the respective ones of the left atrium and left ventricle. As discussed further herein, the upper support 150 can be released within the left atrium and pulled downwardly against the mitral annulus as the lower support 152 is drawn downwardly into and expanded within the left ventricle. Because the upper support 150 is coupled to the lower support 152 via the flexible connector 140 and can be released independently of the lower support 152 in some embodiments, the rotational alignment of the upper support 150 relative to the mitral annulus can be more easily adjusted before expanding the lower support 152, whose engagement structures may otherwise tend to restrict rotational adjustment of the anchoring element 120. Thereafter, the flexible connector 140 can tend to exert a chronic collapsing force between the upper and lower supports 150, 152 that can cause the upper and lower supports 150, 152 to be chronically biased toward each other, thus enhancing engagement of both the upper and lower supports 150, 152 with the mitral valve anatomy.

Optionally, aspects of the upper and lower supports 150, 152 can be rotationally aligned relative to each other in an expanded, default state when coupled to the flexible connector 140. In accordance with such embodiments, if the upper and lower supports 150, 152 are rotated relative to each other from the default state, such movement will cause tension and tensile stress to be exerted on the flexible connector 140. Thus, if the upper and lower supports 150, 152 are rotated relative to each other in either direction about the central axis 142, the flexible connector 140 will want to release torsional stress by re-aligning the upper and lower supports 150, 152 to the alignment in the default state. Thus, during delivery of the anchoring element 120, the upper and lower supports 150, 152 can tend to re-align relative to each other if they are rotated relative to each other. Further, in accordance with some embodiments, the relative positioning of the aspects of the upper and lower supports 150, 152 in the default state can be configured to ensure that aspects of the upper and lower supports 150, 152 tend to be properly positioned relative to mitral valve anatomy when the position of one or the other of the upper or lower supports 150, 152 is adjusted during delivery.

For example, as illustrated in FIGS. 5 and 6, in the default state, opposing ends 164, 166 of the upper support 150 can be rotationally aligned with the hooks 200, 202 of the lower support 152. As such, as discussed above, when the anterior lobe 172 is aligned with the aortic-mitral curtain, the hooks 200, 202 can tend to engage with tissue immediately below the anteromedial and posterolateral commissures 88, 86. For example, in some embodiments, the anterior lobe 172 (illustrated as extending through a plane in the top view of FIG. 7A) can be aligned within less than 20 degrees, within less than 15 degrees, within less than 12 degrees, within less than 10 degrees, within less than 8 degrees, or within less than 5 degrees of a line or plane of the aortic-mitral curtain 92 (e.g., as illustrated by the dashed line 92 in FIG. 4). Thus, in some embodiments, the plane of the flat face of the anterior lobe 172 can land within about 10 degrees of the plane of the aortic-mitral curtain 92 to provide a satisfactory seal between the prosthesis 100 and the surrounding valve structure.

Additionally, in accordance with some embodiments, the flexible connector 140 can provide a fluid impervious seal to mitigate or prevent paravalvular leakage after completion of the implant procedure. The flexible connector 140, as discussed above, can comprise a fabric skirt that extends continuously between and about the perimeters of the upper and lower supports 150, 152. Accordingly, when the upper and lower supports 150, 152 are securely fastened against and oppose the structure of the native mitral valve, the flexible connector 140 can tend to ensure that blood flow does not occur other than through the lumen formed within the flexible connector 140 itself. Accordingly, blood will flow through the mitral valve prosthesis 100, thus avoiding paravalvular leakage, when in some embodiments, the valve component 110 is expanded within the lumen of the flexible connector 140.

Further, in accordance with some embodiments, the anchoring element 120 can be implanted in a patient without subsequent implantation of a valve component such that the complex performs a function similar to that of an annuloplasty ring.

The two-ring design of the anchoring element 120 of some embodiments disclosed herein advantageously permits the anchoring element 120 to be deliverable to a target location within the body, reliably disengage from a delivery system, and securely engage with the mitral annulus. Applicant has performed several studies and tested many iterations of the anchoring element. Various initial designs were shape set using different thicknesses of superelastic nitinol wire. However, regardless of the early changes, many problems in still persisted in delivery and disengagement of the anchoring element from the delivery system. Eventually, a two ring design was developed. The two-ring design achieves the same functions as the other initial designs, but eliminated many of the problems that were encountered.

For example, the upper support (or "top ring") can conform to the native saddle-shaped annulus to form a seal against the endocardium, as well as creates an anchor from the atrial side. The upper support can be made from shape set 0.020" nitinol wire. The upper support can comprise a "D" shape nitinol structure. The lower support (or "bottom ring") can comprise another nitinol ring having hooks formed thereon. The lower support can be connected to the upper support via a flexible connector or tubular skirt. The three hooks of the lower support can be positioned about 120 degrees from one another to latch onto both commissures and the P2 scallop of the native valve to create anchoring points from the ventricular side. The upper and lower supports can be connected via the tubular skirt.

In some embodiments, during delivery, the upper support will not be restrained by graspers or anchor controls of the delivery system, thus allowing the upper support to open more fully, and in some embodiments, can have a larger diameter or size than the lower support. Because the upper support can be more fully open, the anchoring element can provide a surer fit against the mitral annulus, improving seal. This can also improve the upper support's ability to anchor while the physician pulls the anchoring element proximally against the mitral annulus. Further, because the two rings of the anchoring element are separated by a flexible skirt coupling, they can act independently (e.g., the upper support can fully open, and the lower support can be manipulated and allowed to expand and anchor on the native mitral apparatus). Further, the circular shape of the valve prosthesis, when seen from the axial view, creates a seal around the implanted valve component. In various tests, harvested tissue models were used for benchtop testing to verify and optimize the form and function of these features.

Further, in some embodiments, the crown shape of the lower support is designed to crimp into the delivery sheath in a uniformed manner. During implantation, the upper support can first deploy in the atrium before positioning and releasing the lower support. This two-step deployment is more robust and easier to control. The arch on the flat face of the upper support can advantageously allow the upper support to conform to variations in size and shape of a patient's annulus, while still maintaining a seal against the endocardium.

Finally, in accordance with some embodiments, the tubular skirt connecting the two subassemblies serves several key purposes. Tension from the fabric on the upper and lower supports ensures that the anchor locks into position and will not migrate after implantation. Slight elasticity from both the fabric and the native tissue lets the hooks slip into their intended anchor points and then rebound to lock in place. Further, the tubular skirt can also act as a hemostatic seal around the prosthetic valve to reduce paravalvular leakage and promote ingrowth after the device has been implanted.

Valve Components

As noted above, in some embodiments, the mitral valve prosthesis 100 can comprise the anchoring element 120 and the valve component 110. The valve component 110 can comprise any of the valve components disclosed in U.S. Pat. Nos. 8,444,689, 8,540,767, 8,366,768, 8,366,767, or U.S. Patent Application No. US 2014/0052240, the entireties of each of which are incorporated herein by reference; further, the surgical approaches disclosed therein can be used to deliver any of the valve prostheses disclosed herein, according to some embodiments.

As shown in FIG. 5, the valve component 110 can include an expandable valve frame 210 to which prosthetic valve leaflets can be attached, e.g., to an inner surface of the valve frame 210. The valve frame 210 can expand radially to a tubular shape wherein the cross-section is circular and has an outer or external surface and defines a central orifice about an axis (the longitudinal axis). The longitudinal axis corresponds to the inflow-outflow axis. The valve frame 210 can be manufactured from a self-expanding shape memory metal. The valve frame can comprise a mesh or braided tubular material or be laser-cut from a tubular material. In some embodiments, the metal is nitinol. In an alternative embodiment, the valve frame 210 may comprise a material that is not self-expanding, but instead can be expanded by a separate component, e.g., through the use of a balloon catheter.

There may be a plurality of prosthetic valve leaflets attached to the inner surface, each made of a flexible material which mimics the anatomical structure and physiological function of native cardiac valve leaflets. In some embodiments, two or three prosthetic valve leaflets are attached to the inner surface. The prosthetic valve leaflets can comprise a material selected from the group human, bovine, porcine, or equine pericardium tissue, or aortic root from human, bovine, or porcine. Alternatively, the prosthetic valve leaflets can comprise a biocompatible polymer material. Thus, the valve may be either a xenograft or a homograft. It may be beneficial if the material is treated, e.g., with glutaraldehyde, to improve biocompatibility. The biocompatible material to be used as valve replacement is usually fabricated by fixing the material in glutaraldehyde solution, which functions as a tissue preservative. Although fixation in glutaraldehyde may imply drawbacks in view of biomaterial calcification, glutaraldehyde fixation still remains the method of choice for preserving tissue and preparing it for implantation as a biomaterial. In this connection, may be beneficial if the valve component is treated with a substance that prevents calcification, e.g., with dimethyl sulfoxide, or similar.

The valve component 110 can comprise a circular cross section, which can permit the attached prosthetic valve leaflets to be coupled thereto. The valve frame 210 may further comprise a plurality of spikes or barbs on its outer surface. Such barbs help to anchor the implanted valve component within the heart and prevent movement of the implanted prosthesis as the heart contracts during its normal physiological functioning. The barbs, when present, can be made from a self-expanding shape memory material and can thus adopt a compact or expanded condition. For example, when the valve component 110 is uncovered and allowed to expand during deployment, the barbs can also expand to protrude upward, outward, and/or downward.

The valve component 110 may comprise a liner or covering such as a fabric or mesh covering, which may be attached to the outer and/or inner surface of the valve frame 210. In some embodiments, the covering can be impervious to blood or other fluids.

Figure 10A:
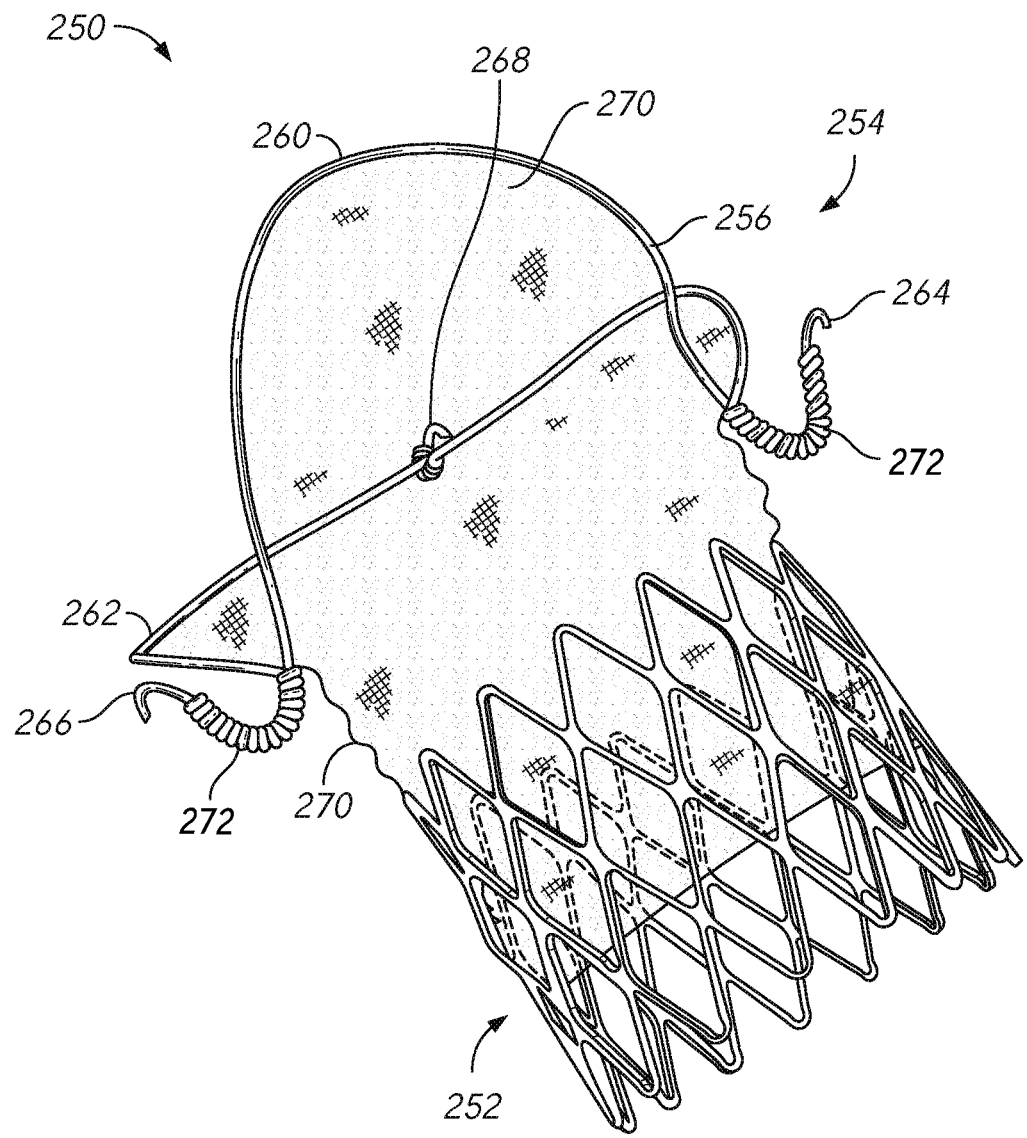
FIGS. 10A-10C illustrate a mitral valve prosthesis, according to some embodiments.
Figure 10B:
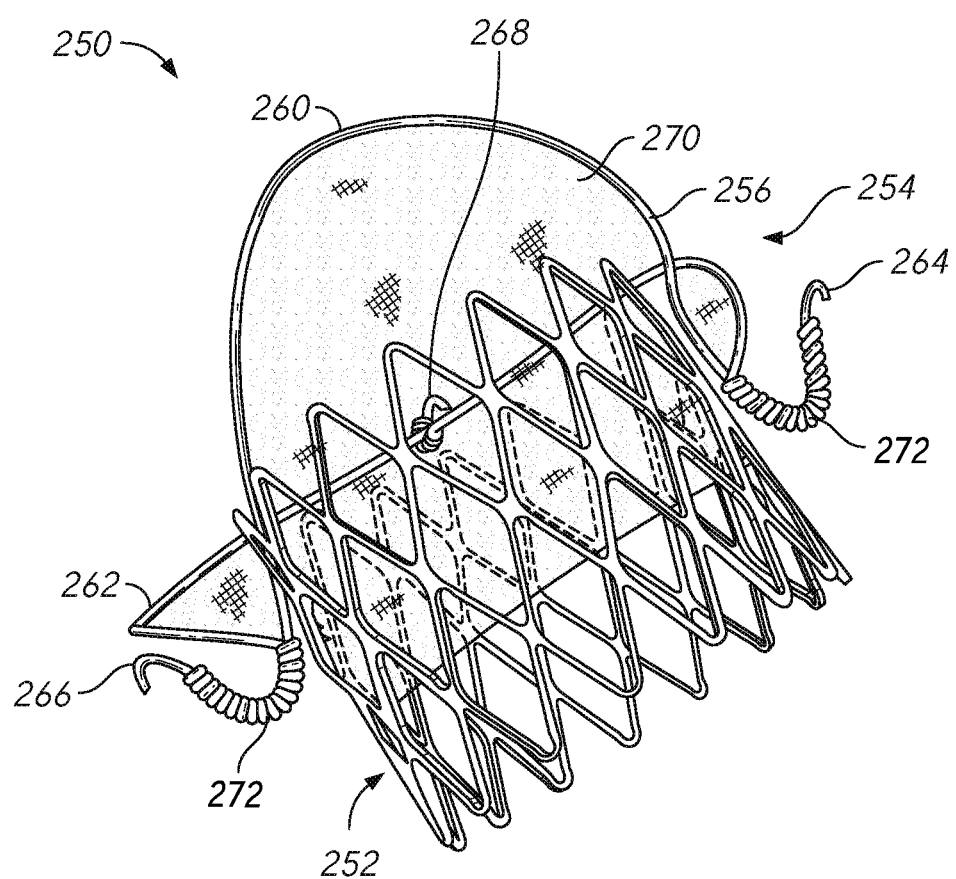
Figure 10C:
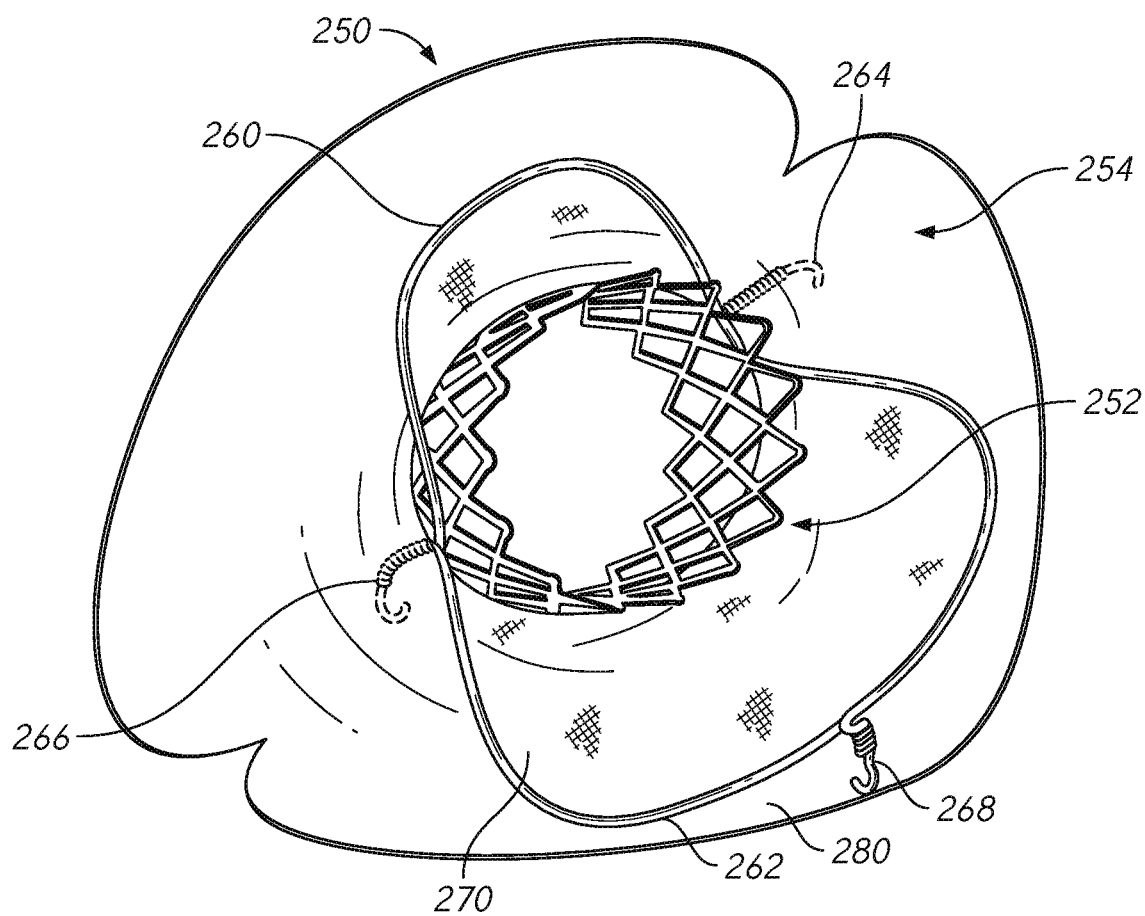
Figure 11A:
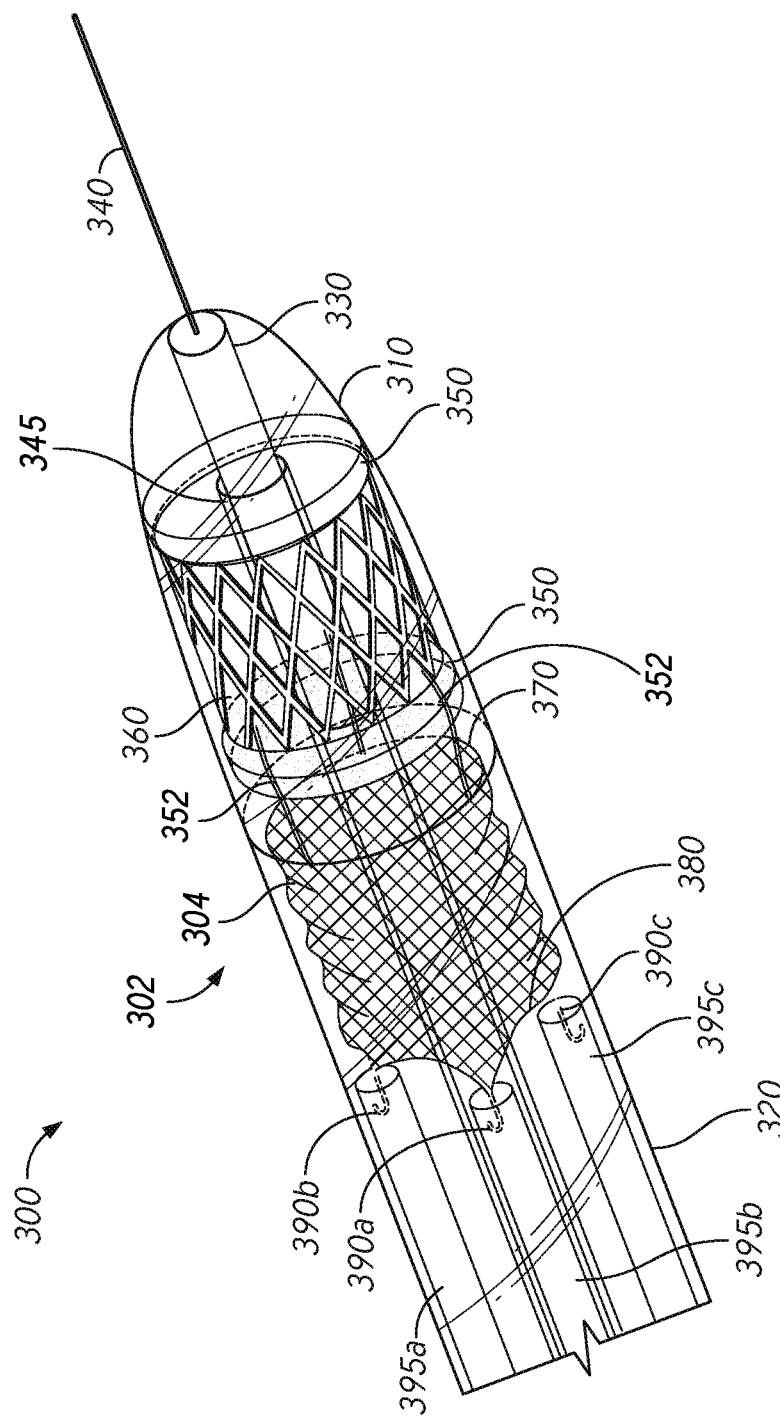
FIGS. 11A-11C illustrate a valve prosthesis delivery device, according to some embodiments.
Figure 11B:
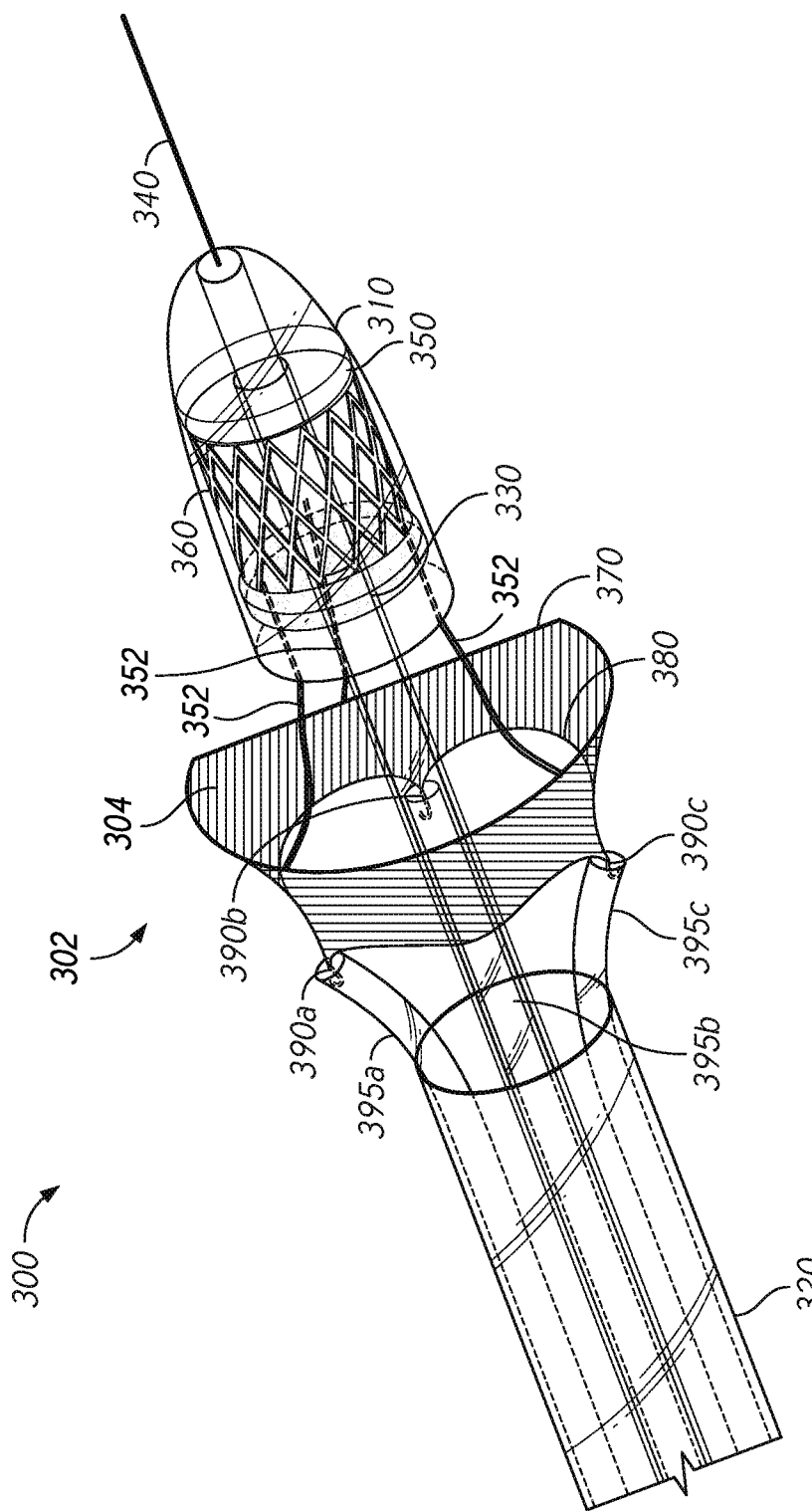

Embodiments of a valve component for use in the mitral valve prosthesis described herein are shown in FIGS. 5-6 (valve component 110), FIGS. 10A-10C (valve component 252), and FIGS. 11A and 11B (valve component 360).

Coupling Between the Anchoring Element and the Valve Component

In some embodiments that use both anchoring element and a valve component, the anchoring element 120 can comprise a structure separate from and/or independently expandable of the valve component 110. In such embodiments, the anchoring element 120 and the valve component 110 can be interconnected using the coupler component 122, which can provide a range of free relative movement between the anchoring element 120 and the valve component 110. In some embodiments, the coupler component 122 can be coupled to the upper support 150 and/or the lower support 152.

Referring again to FIG. 5, the coupler component 122 can comprise one or more thread-like structures. In some embodiments, the coupler component 122 can comprise one or more sutures. For example, in some embodiments, the coupler component 122 can comprise one, two, three or more thread-like structures, filaments or fibers, for example, sutures. The coupler component 122 can comprise three sutures wherein a first end of each of the sutures is attached to the anchoring element 120 and a second end of each of the sutures is attached to the valve frame 210 of the valve component 110. In some embodiments, the sutures, when two or more are present, are spaced equidistant apart. Because of the interconnection between the valve component 110 and the anchoring element 120 created by the coupler component 122, the maximum separation or distance between the valve component 110 and the anchoring element 120, when either is pulled in a proximal or distal direction, can be determined at least in part by the length of the coupler component 122.

In FIG. 5, the coupler component 122 is illustrated as threads 124a, 124b, 124c. For example, the coupler component 122 can comprise one or more sutures, each connected at its first end to the anchoring element 120 and at its second end to the valve component 110. In an alternative embodiment, the coupler component comprises a flexible member such as a piece of fabric or mesh which is attached to both the anchoring element 120 and to the valve component 110. For example, in some embodiments, the coupler component 122 is a continuous material impervious to fluid, which can prevent a paravalvular leak after implantation of the anchoring element 120 and valve prosthesis 100.

In accordance with some embodiments, the coupler component 122 can have a fixed length which determines the range of longitudinal or rotational movement that the anchoring element 120 can have relative to the valve component 110. For example, the anchoring element 120 can move along the central axis 142 (correlating to the inflow-outflow axis when present in the native valve annulus) such that it can be apart from the valve component 110 along the longitudinal axis at a distance which is about 10% to 100%, 25% to 75%, 33% to 100%, 33% to 66%, 25% to 75% or 50% to 75%, or 60% to 70% the length of the valve component 110. The anchoring element 120 can move along its longitudinal axis to overlap the valve component 110 by 10% to 100%, 25% to 75%, 33% to 100%, 33% to 66%, 25% to 75% or 50% to 75% the length of the valve component 110.

The coupler component 122 can allow rotational movement of the anchoring element relative to the valve component 110. Thus, despite the presence of the coupler component 122, the anchoring element can move rotationally with respect to the valve component 110. In some embodiments, the coupler component 122 can rotate freely when the valve component 110 is held steady, wherein the free rotation ranges from between about 180 degrees to about 460 degrees, between about 180 degrees to about 360 degrees, between about 180 degrees to about 340 degrees, between about 180 degrees to about 300 degrees, between about 180 degrees to about 280 degrees, or between about 180 degrees to about 260 degrees, about the central axis 142.

Optionally, the flexible material connecting the anchoring element 120 to the coupler component 122 allows the valve component 110 to be more easily alignable within or with respect to a lumen of the anchoring element 120. Further, some embodiments, the coupler component 122 can enable the valve component 110 to be more easily positioned within a perimeter of the upper support 150 and lower support 152 of the anchoring element 120. The coupler component 122 can also allow the valve component 110 to stay within a longitudinal distance adjacent or serial to the anchoring element 120 along the longitudinal axis 142. For example, prior to and during delivery of the anchoring element 120 to the native mitral valve annulus, the upper support 150 can be released and positioned proximal to the valve component 110. The coupler component 122 can impart a limit on both the distance the valve component 110 can be separated from the anchoring element 120 as well as the position of the valve component 110 relative to the anchoring element 120 when the valve component 110 is positioned within a perimeter of the anchoring element 120, such as when the anchoring element 120 is released in a native valve annulus.

The coupler component 122 between the valve component 110 and the anchoring element 120 is important for allowing compact and efficient delivery and deployment of the valve prosthesis 100 in the native mitral valve annulus of a patient in need thereof. Specifically, during delivery to and prior to deployment in the native valve annulus, the anchoring element 120 and the valve component 110 can be positioned serially to or longitudinally spaced apart from one another. In some embodiments, a lack of overlap between the two during advancement to the target location allows the system to have a smaller diameter, for example, when the valve prosthesis 100 is in its compact condition during delivery to the heart through vessels or other openings. Moreover, some embodiments of the valve prosthesis 100 allow the deployment (release or expansion) and positioning of the anchoring element 120 within the native valve annulus independently of and prior to positioning and deployment of the valve component 110.

In some embodiments, the coupler component 122 can comprise a tubular structure, such as a tube of fabric. The tubular structure of the coupler component 122 can define a first end, which can be fixed or connected along its entire edge to the entire circumference of the anchoring element 120. The coupler component 122 can define a second end which is fixed or connected to the valve component 110. The second end can be connected to the valve frame 210 at a position such that the attached fabric covers about one-fourth, one-third, one-half, two-third, or three-fourths of the valve component 110 or any range in between. In an alternative embodiment, the second end of the fabric can be connected to the valve frame 210 at a position such that the attached fabric covers the entire surface of the valve component 110. Alternatively, the second end of the fabric can be attached to the end of the valve component 110 closest to the anchoring element 120 such that the valve component 110 is not covered by the connector fabric along its side. When the fabric of the coupler component 122 does not cover the valve component 110, there may be a separate fabric-like material covering all or a portion of the valve frame. This separate fabric-like material can minimize or block leakage of blood through the valve component 110 (paravalvular leakage).

In some embodiments, the fabric of the coupler component 122 can be fabricated from a flexible fabric-like material. This material may be made from, e.g., a polyester polymer. Fabrics as used herein for flexibly connecting an anchoring element 120 to the valve component 110, are generally known in the art, and may comprise any natural or synthetic polymer that is biocompatible and suitable as a "jacket" for the stent framework. Further, the polymers may be coated with a medically active substance or any other substance to influence and/or treat a condition of a patient at the site of implantation of the prosthesis 100. The medically active substances can, for example, prevent stenosis, accelerate healing of wounds of the inside wall of the vessel, or prevent the development of inflammations. In addition, the anchoring element 120 and/or the valve component 110 may be coated or treated with medically active substance. In some embodiments, the fabric can be porous to allow blood flow through the fabric during the valve prosthesis implantation procedure.

Figure 9A:
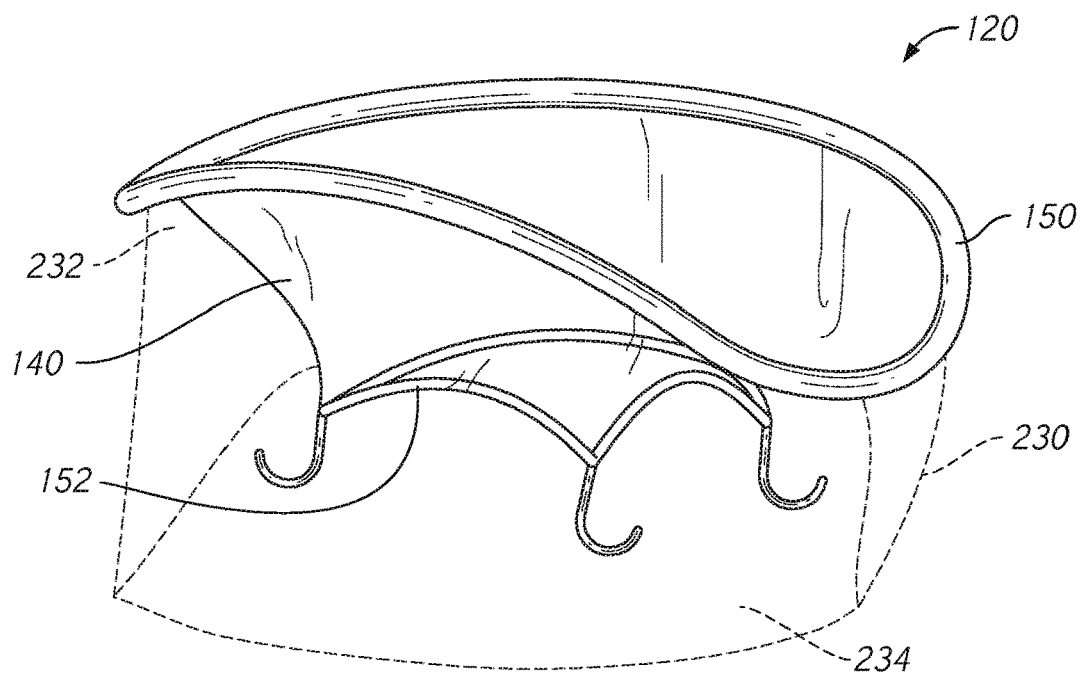
FIGS. 9A and 9B illustrate bottom and perspective views of a mitral valve prosthesis having first and second skirts, according to some embodiments.
Figure 9B:
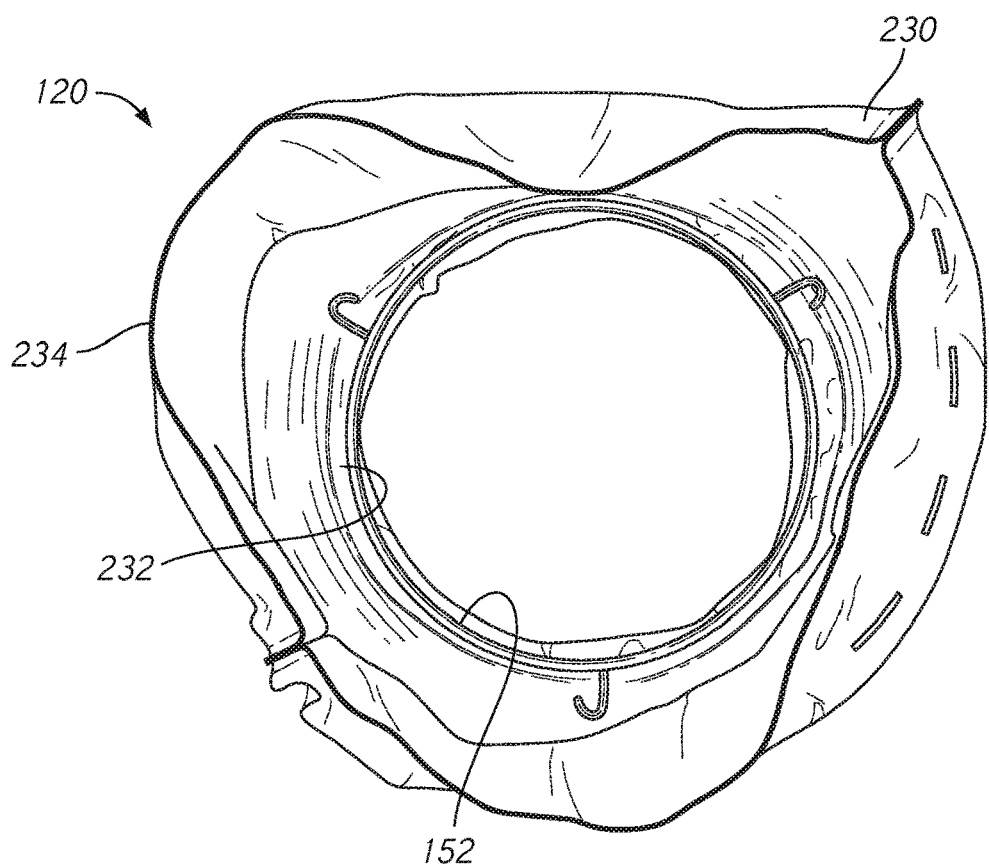

Referring now to FIGS. 9A and 9B, an alternative embodiment of the anchoring element 120 can comprise a filler component or skirt 230. FIG. 9A illustrates a perspective view of the anchoring element 120 and filler component 230, while FIG. 9B illustrates a bottom view of the anchoring element 120 and the filler component 230.

In accordance with some embodiments, the filler component 230 can advantageously act as a filler material that occupies any gap between the mitral annulus and the anchoring element 120 when the prosthesis 100 is positioned the patient, thereby enabling the filler component 230 to act as a means to reduce paravalvular leakage. Further, the filler component 230 can also improve the anchorage of valve prosthesis (e.g., by acting as a valve flap during ventricular contraction.

The filler component 230 can be coupled to the anchoring element 120 along an upper region thereof. For example, an upper end region 232 of the filler component 230 can be attached to the upper support 150 or to a portion of the flexible connector 140. A lower end region 234 of the filler component 230 can extend away from the upper end region 232 in a direction toward the lower support 152. The lower end region 234 can extend about a perimeter of the lower support 152. In some embodiments, the lower end region 234 can extend downwardly passed the lower extent of the lower support 152. However, the lower end region 234 can also extend to a location interposed between the upper and lower supports 150, 152.

The filler component 230 can be formed as a tubular member using any of the materials disclosed herein with respect to the flexible connector 140 and/or the coupler component 122. In some embodiments, the filler component 230 can be fabricated from a flexible fabric or mesh-like material, e.g., a polyester polymer. In some embodiments, the fabric can be porous to allow blood flow through the fabric during the valve prosthesis implantation procedure. Alternatively, the filler component 230 can comprise a fabric-like material that can partially or fully prevent permeation of blood through the filler component 230. In some embodiments, the filler component 230 can comprise a shape memory flexible material, such as fabric with in-woven nitinol wires, to help shape the coupler component 122. Further, the filler component 230 may be coated with a medically active substance or any other substance to influence and/or treat a condition of a patient at the site of implantation of the prosthesis 100. The medically active substances can, for example, prevent stenosis, accelerate healing of wounds, or prevent the development of inflammations.

Advantageously then, in accordance with some embodiments disclosed herein, the valve component can be a separate component from the anchoring element and can be flexibly attached thereto via a coupling. Such embodiments therefore make it possible that the anchoring element and the valve component can be implanted in two separate operations.

Mitral Valve Prostheses Comprising a Single Anchoring Ring

FIGS. 10A and 10B illustrate a valve prosthesis 250 that comprises a valve component 252 and an anchoring element 254, wherein the anchoring element 254 comprises a single anchoring ring 256. The anchoring ring 256 can comprise an anterior lobe 260, a posterior lobe 262, and hooks 264, 266, 268 as described above. The valve component 252 and anchoring ring 256 are each a self-expanding structure. Mounted on the internal face of the valve component 252 is a plurality of prosthetic valve leaflets (not shown). FIG. 10A show the valve component 252 and anchoring ring 256 as serially displaced from each other along the longitudinal axis. While FIG. 10A shows the valve component 252 and anchoring ring 256 both in an unfolded or expanded condition, during actual delivery of the valve prosthesis, the valve component 252 and anchoring ring 256 can be in a compact condition until after the anchoring ring 256 is released, as described in more detail below.

FIG. 10A shows embodiments of an anchoring ring 256 in an expanded condition and circumferential with the valve component 252, including posterior lobe 262 and anterior lobe 260 with a first hook 264 and a second hook 266 positioned at indentations between posterior lobe 262 and anterior lobe 260. A third hook 268, which can be present in some embodiments, can be positioned midway on posterior lobe 262. An embodiment of a coupler component 270 is shown in FIGS. 10A-10C wherein coupler component 270 comprises a tubular fabric attached to both anchoring ring 256 and the valve component 252. When the valve prosthesis 250 is situated in the native valve annulus, the anchoring ring 256 can be positioned external to the valve component 252 such that the anchoring ring 256 encircles the valve component 252 and is partially or fully concentric with the valve component 252 (as shown in FIGS. 10B and 10C). FIGS. 10A and 10B also illustrate that some or all of the hooks 264, 266, 268 can be covered with a fabric or suture material 272 in order to reduce or eliminate risk of irritation and scar tissue buildup.

FIG. 10C depicts a top view looking downwardly from the left atrium into the left ventricle of the mitral valve prosthesis 250 situated in a native valve structure 280. The anchoring ring 256 can be flexibly connected to the valve component 252 before and during release within the native valve annulus 280. However, once released, the hooks 264, 266, 268 can be below the native valve annulus 280 and the anterior lobe 260 and the posterior lobe 262 can be above the native valve annulus 280 (in the left atrium), and the valve component 252 is fully expanded in a radially direction. The valve component 252 can be expanded within and coupled to the anchoring ring 256 to remain stationary relative to one another, thus permitting the valve prosthesis 250 to remain substantially stationary relative to the native valve annulus. Thus, as the heart pumps blood and blood flows through the mitral valve prosthesis 250, prosthetic leaflets of the valve component 252 can move as does a healthy native valve yet remains situated within the native valve annulus 280.

Delivery Systems for the Mitral Valve Prosthesis

Also described herein is a delivery system for, e.g., apical or transcatheter delivery of a mitral valve prosthesis. The delivery system can support a valve prosthesis, wherein the delivery device comprises a first sheath, a second sheath and a control unit, wherein the first sheath is distal to the second sheath and the second sheath is distal to the control unit. In some embodiments, the first sheath can comprise a tapered end portion. The first and second sheaths can at least partially enclose the valve component and the anchoring element prior to and during valve prosthesis delivery. It is understood that the configuration of the delivery system with respect to the first and second sheaths, the valve component, and the anchoring element can be any configuration which allows serial positioning along the longitudinal axis of the anchoring element and the valve component in a compact condition during delivery followed by independent release and positioning of the anchoring element prior to positioning and releasing the valve component, as described in greater detail below.

Figure 11C:
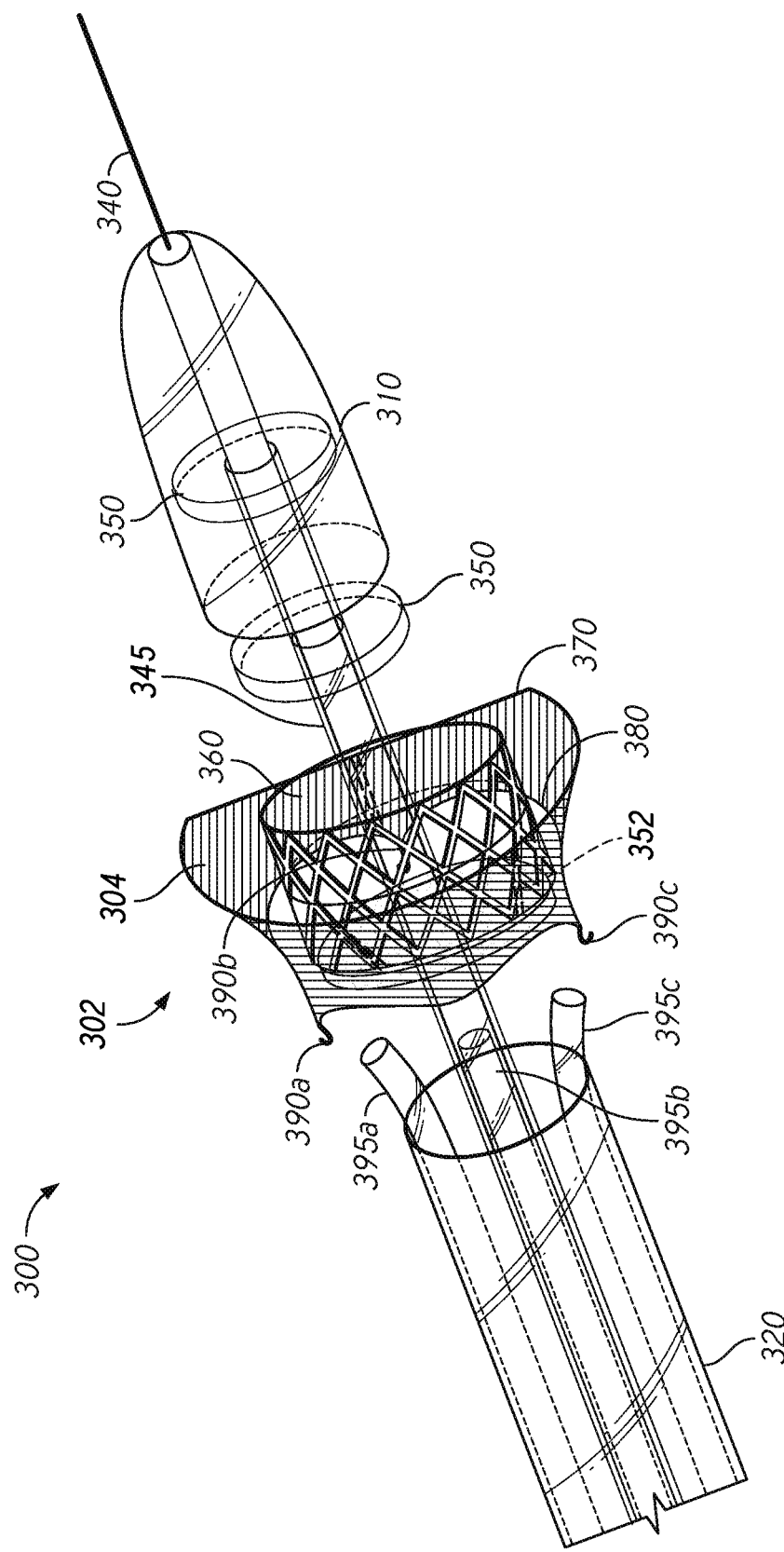

Reference is now made to FIGS. 11A-11C, illustrating an embodiment of a delivery system 300 used to deliver and release a valve prosthesis 302, as described herein. The delivery device comprises a first sheath 310 and a second sheath 320, which is proximal to the first sheath 310. The second sheath 320 is distal to a control unit (not shown) through which the physician controls various components of the delivery system 300. Together, the first and second sheaths 310, 320 can house the valve prosthesis 302 during delivery of the valve prosthesis to a target location within the body (e.g., discussed and shown herein as the mitral valve annulus).

FIG. 11A shows a configuration of a delivery system 300 prior to delivery and during delivery prior to releasing the valve prosthesis 302. The valve prosthesis 302 can be configured to comprise the features of the valve prosthesis 100 or the valve prosthesis 250, discussed above. FIG. 11B shows a configuration of the same delivery system 300 during delivery, but after releasing an anchoring element 304 (such as anchoring element 120) and prior to releasing a valve component (such as valve component 110).

In accordance with some embodiments, as shown in FIGS. 11A and 11B, the delivery system 300 can comprise a central shaft 330 that extends through the length of the center of the first sheath 310 and the second sheath 320. The distal end of central shaft 330 can be attached to an internal surface of the first sheath 310 such that by controlling longitudinal movement of central shaft 330 (e.g., through pushing or pulling central shaft 330), a physician can control longitudinal movement of the first sheath 310 independently of the second sheath 320 in order to enable movement of the first sheath 310 relative to the second sheath 320. In some embodiments, to facilitate delivery of the system 300 to the target location, the central shaft 330 can be configured to permit the system 300 to move along a guidewire 340, which can extend through the length of the center of central shaft 330.

The delivery system 300 can optionally comprise a counter nose cone or valve seat 350 at the distal end of a valve control line 345. The valve seat 350 can comprise a pair of discs that are spaced apart along the longitudinal axis and interconnected by a valve control lumen or line 345. The valve seat 350 can provide a location or space within which the collapsed valve component can be supported during delivery and during relative movements between the sheaths and the components of the prosthesis. An end surface of the counter nose cone 350 can abut the anchoring element and/or the valve component and maintain the anchoring element and/or the valve component within either or both of the first or second sheaths during delivery. The valve seat 350 can resolve the friction force of the valve component in the first sheath or nose cone during loading and delivery. The valve control line 345 can be attached to the control unit at the proximal end of the delivery system 300, extend through the center of the second sheath 320, and terminate at the valve seat 350.

The delivery system 300 can comprise at least one grasper or anchor control sleeve 395a, 395b, or 395c, as shown in FIGS. 11A and 11B. The number of anchor control sleeves preferably equals the number of engagement members or hooks of the anchoring element 304 (e.g., the number of engagement members of the lower support as in the valve prosthesis 100). Each of the anchor control sleeves 395a, 395b, and 395c can be connected at its proximal end to the control unit. The distal end of each of the anchor control sleeves 395a, 395b, and 395c can enclose or be coupled to a hook of the anchoring element 304. The interconnection between the distal ends of the anchor control sleeves 395a, 395b, and 395c and the engagement members of the anchoring element 304 can permit the anchoring element 304 of the valve prosthesis 302 to be held in a stationary and/or collapsed position relative to or within the second sheath 320. When the second sheath 320 is proximally retracted relative to the distal ends of the anchor control sleeves 395a, 395b, and 395c, the engagement members of the anchoring element 304 can be released from the distal ends of the anchor control sleeves 395a, 395b, and 395c as the anchoring element 304 expands. Accordingly, a physician can control longitudinal movement of the anchor control sleeves to effect longitudinal movement of the anchoring element 304.

In some embodiments of the delivery system 300, as illustrated in FIG. 11A, a valve component 360 of the valve prosthesis 302 can be enclosed within the first sheath 310 prior to releasing the valve component 360 in the native valve annulus. The anchoring element 304 can be enclosed within the second sheath 320 (e.g., by the distal end of the second sheath 320) prior to releasing the anchoring element 304. While FIG. 11B specifically shows an anchoring element 304 which comprising a D-ring 370 and an anchoring skirt 380 (such as that illustrated in FIGS. 5 and 6), the valve prosthesis delivery system 300 having the configuration shown in FIGS. 11A-11C can be functional using an anchoring element such as that discussed above in FIGS. 10A-10C.

In alternative embodiments of the delivery system 300, the anchoring element 304 and the valve component 360 can both be enclosed within the second sheath 320 prior to and during delivery prior to releasing the anchoring element 304. For example, in some embodiments, the anchoring element 304 can be distal to the valve component 360 wherein the anchoring element 304 is near the distal end of the second sheath 320 and the valve component 360 can be approximately adjacent to the anchoring element 304 (in a serial configuration) and is proximal to the anchoring element 304. In some embodiments of the delivery system 300, the anchoring element 304 and the valve component 360 can both be enclosed within the second sheath 320, with the valve component 360 near the distal end of the second sheath 320 and the anchoring element 304 being approximately adjacent to the valve component 360 and proximal to the valve component 360.

In some embodiments of the delivery system, the anchoring element 304 can be enclosed within the first sheath 310 and the valve component 360 can be enclosed within the second sheath 320 prior to and during delivery of the valve prosthesis 302. For example, in some embodiments of the delivery system 300, both the anchoring element 304 and the valve component 360 can be enclosed within the first sheath 310 and the valve component 360 can be enclosed within the second sheath 320 prior to and during delivery of the valve prosthesis 302. In this configuration, the anchoring element 304 and the valve component 360 can be approximately adjacent to one another (in a serial configuration) and the anchoring element 304 can be positioned proximal to the valve component 360.

In any of the above configurations of the delivery system 300, the physician can independently release the anchoring element 304 and the valve component 360. The anchoring element 304 can be released prior to releasing the valve component 360.

Also, in any of the above configurations of the delivery system 300, the anchoring element 304 can optionally be manipulated after deployment near the native valve annulus. For example, after releasing the anchoring element 304 from the delivery system 300, each of the hooks of the anchoring element 304 can be releasably or reversibly connected to an anchor control sleeve 395*a*, 395*b*, and 395*c* (e.g., a hook is enclosed by an anchor control sleeve 395*a*, 395*b*, and 395*c*) and the physician can move the anchoring element 304 along either the rotational or longitudinal axis in order to properly position the anchoring element 304 within the native valve annulus prior to positioning and releasing the valve component 360.

Prior to releasing the valve prosthesis 302, i.e., before and during delivery to the native valve site, the anchoring element 304 and the valve component 360 can be positioned adjacent to one another along the longitudinal axis of the delivery system 300. This configuration, as opposed to a concentric arrangement, allows a more radially compact configuration of the two pieces of the valve prosthesis 302, facilitating catheter-based delivery.

As discussed herein with respect to other embodiments, the anchoring element 304 and the valve component 360 can be flexibly connected by at least one coupler component 352, as shown in FIGS. 11A and 11B. The coupler component 352 can be configured as the coupler component 122, discussed above. For example, the coupler component 352 may comprise a suture or other flexible chord that can be connected to both the anchoring element 304 and the valve component 360. In some embodiments, one end of the coupler component 352 can be attached to a fixed position on the anchoring element 304 and the other end can be attached to a fixed position on the valve component 360. In some embodiments, only one end of the coupler component 352 is attached to a fixed position on the anchoring element 304 or on the valve component 360. Further, in some embodiments, the coupler component 352 can comprise a loop or band of material that flexibly connects the valve component 360 and anchoring element 304 without being tied or fixed to single position on either the valve component 360 or anchoring element 304. In some embodiments, the coupler component 352 between the anchoring element 304 and the valve component 360 can comprise a fabric material, such as a fabric tube (see e.g., FIGS. 10A and 10B).

The coupler component 352 can comprise any means by which the valve component 360 can move along the longitudinal axis relative to the anchoring element 304 while limiting the maximum distance of longitudinal movement between the valve component 360 and the anchoring element 304. In some embodiments, the physician can reach a maximum distance between the anchoring element 304 and the valve component 360 with the valve component 360 being positioned proximal or distal to the anchoring element 304. When the coupler component 352 is in this taut position, the physician can exert additional longitudinal force to gently pull the anchoring element 304 in a proximal or distal direction to adjust the position of the anchoring element 304 within the native valve. The anchoring element 304 can be positioned with lobes and hooks of its lower support engaged within the left ventricle and the upper support or D-ring positioned within the left atrium. When the anchoring element 304 comprises an anchoring ring as described above in FIGS. 10A-10C, the anchoring element 304 can be positioned within the native valve when the hooks are on opposite sides of the annulus such that the hooks are in the left ventricle and the lobes are in the left atrium. When the anchoring element 304 has been properly positioned within the native valve annulus, the valve component 360, enclosed in either the first or second sheath 310, 320, can be moved along the longitudinal axis toward and to a position within a lumen of or longitudinally overlapping the anchoring element 304. In some embodiments, the anchoring element 304 can be positioned at least partially or fully concentric to the valve component 360. Accordingly, when positioning the valve component 360 of the valve prosthesis 302 within the native valve annulus, the valve component 360 can have a fixed range of motion along the longitudinal axis. Further, by providing a flexible connection with a calculated and fixed range of movement along the longitudinal axis, the physician can know when the anchoring element 304 and the valve component 360 are spaced apart from each other or properly positioned in relation to one another. In some embodiments, once the anchoring element 304 can move no further due to the coupler component 352, the anchoring element 304 and the valve component 360 are properly positioned with respect to each other and the valve component 360 can be released.

Further, in accordance with some embodiments, the anchoring element 304 can move freely about its rotational axis while the valve component 360 is held steady. This free rotation can occur both before and after release from a sheath and expansion due to the pliable nature of the anchoring element 304. The lobes and hooks can work together to stabilize the anchoring element 304 within the native valve annulus. For example, after releasing the anchoring element 304 from a sheath so that it expands in the left atrium, the physician can move the anchoring element 304 both longitudinally and rotationally until the appropriate lobe of the anchoring element 304 (e.g., the straight side of the D-ring as viewed from the top, as discussed above) is properly located at the atrial portion of the mitral valve annulus, e.g., with the straight side being aligned with the aortic-mitral curtain.

After releasing the anchoring element 304, the hooks and/or lobes thereof can be expanded and pulled to a position through the annulus (or pulled through the annulus and expanded) to allow contact with structures such as papillae in the left ventricle. At this time in the implantation procedure, prior to releasing the valve component 360, the configuration and positioning of the anchoring element 304 can prevent movement of the anchoring element 304 towards the left ventricle or left atrium. For example, when the anchoring element 304 comprises a D-ring-shaped upper support, the upper support can reduce and/or prevent migration of the anchoring element 304 further towards the left ventricle while the lower support can reduce and/or prevent migration of the anchoring element 304 towards the left atrium. When the anchoring element 304 comprises an anchoring ring, the lobes in the left atrium can prevent movement of the anchoring element 304 further towards the left ventricle while the hooks in the left ventricle can prevent movement of the anchoring element 304 towards the left atrium.

In some embodiments, the delivery system 300 can deliver a prosthesis that does not include a valve component. A delivery system having an anchoring element without a valve prosthesis can be used to deliver and implant only the anchoring element, which may function similarly to an annuloplasty ring.

In some embodiments, the delivery system 300 can deliver a prosthesis that does not include an anchoring element. Accordingly, treatment of a patient having a mitral valve disorder may comprise first delivering and implanting an anchoring element as described herein, removing the delivery system, then separately and subsequently delivering and implanting a valve component.

Prosthesis Implantation Using a Check Valve

In some embodiments, the delivery system can further comprise a check valve that is released temporarily during delivery of the valve prosthesis. Specifically, the check valve can be released and maintained in an expanded condition after releasing the anchoring element and prior to releasing the valve component. During the time it is expanded, the check valve can prevent backflow of blood during the delivery procedure resulting in less stress on the patient's heart. After the valve component is released in the native valve annulus, the check valve can be compressed and removed from the patient with the delivery device.

Figure 12:
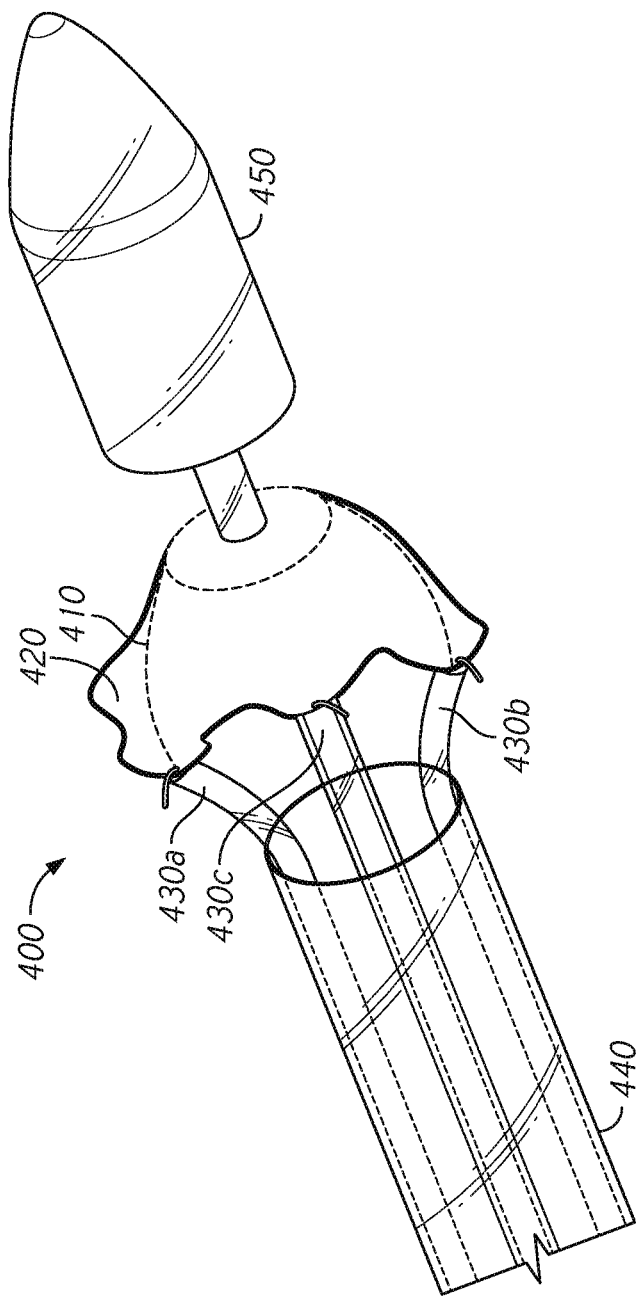
FIG. 12 illustrates a check valve that can be delivered using a delivery system, according to some embodiments.

For example, FIG. 12 illustrates a delivery system that is being used to deploy a check valve 400. The check valve 400 can be used to minimize back flow of blood during the valve prosthesis delivery procedure when the native mitral valve leaflets are rendered non-functional by the presence of the delivery system. As shown in FIG. 12, the check valve 400 can comprise a check valve frame 410 and a cover component 420. The check valve frame 410 can comprise a self-expanding and/or shape memory material. Further, the check valve frame 410 can be coupled to a plurality of check valve control lines 430*a*, 430*b*, 430*c* that can be manipulated by the physician to control releasing check valve 400. Further, in some embodiments, the cover component 420 can comprise a fabric material that is impervious to fluid.

The check valve 400 can be positioned within the delivery system in a compact condition prior to and during delivery of the valve prosthesis. The check valve 400 can be enclosed within a first sheath 440 or a second sheath 450 of the delivery system. In some embodiments, prior to releasing the anchoring element, the check valve 400 can be enclosed in the second sheath 440. The check valve 400 may be positioned proximally to, distally to, or concentrically with an anchoring element enclosed in the second sheath 440 prior to releasing the anchoring element. After releasing the anchoring element, but prior to releasing of the valve frame, the check valve frame 410 can be pushed in a distal direction to exit the distal end of the second sheath 440 and expand accordingly, resulting in the cover component 420 blocking backflow of blood through the mitral valve annulus.

In some embodiments, each of the proximal ends of the check valve frame 410 can be coupled to the distal end of an anchoring control sleeve (e.g., the anchor control sleeve 395*a*, 395*b*, and 395*c*) so that the check valve 400 is released approximately simultaneously with the deployment of the anchoring element of the prosthesis.

Methods for Implanting a Mitral Valve Prosthesis

Methods for implanting a mitral valve prosthesis using any of the implantation, delivery, and valve prosthesis devices described herein may vary with respect to route of delivery and the anchoring element used, but all methods may involve minimally invasive transcatheter delivery and implantation of a mitral valve prosthesis wherein a self-expandable valve component with prosthetic leaflets is flexibly coupled by a coupler component to a self-expandable anchoring element and wherein the valve component and anchoring element are delivered in a compact condition, wherein the valve component and anchoring element are serially positioned relative to one-another along a longitudinal axis.

Regardless of the route of administration, the anchoring element can be manipulated and re-positioned after deployment independently of the valve component to ensure proper placement. The mitral valve prosthesis can be implanted over the existing native mitral valve leaflets. After proper placement of the anchoring element, the valve component is moved along the longitudinal axis toward the anchoring element for a distance which is determined by the length of the coupler component such that the valve component is concentric with the anchoring element, at which time the valve component can be released and the delivery device is removed from the patient. The anchoring element is positioned using, in part, imaging such as ultrasound imaging. In some embodiments, the physician can feel engagement of the anchoring element in the native valve annulus to facilitate proper positioning of the anchoring element along the longitudinal axis of the native valve.

Some embodiments of the methods for delivering a mitral valve prosthesis to a defective mitral valve in a patient are shown and discussed with respect to FIGS. 13-17, which illustrate a method of using a delivery system 500 to deliver a mitral valve prosthesis 510. Various embodiments and features of the delivery system 500 are described above with reference to FIGS. 11A-11C and will not be repeated herein for brevity.

Figure 13:
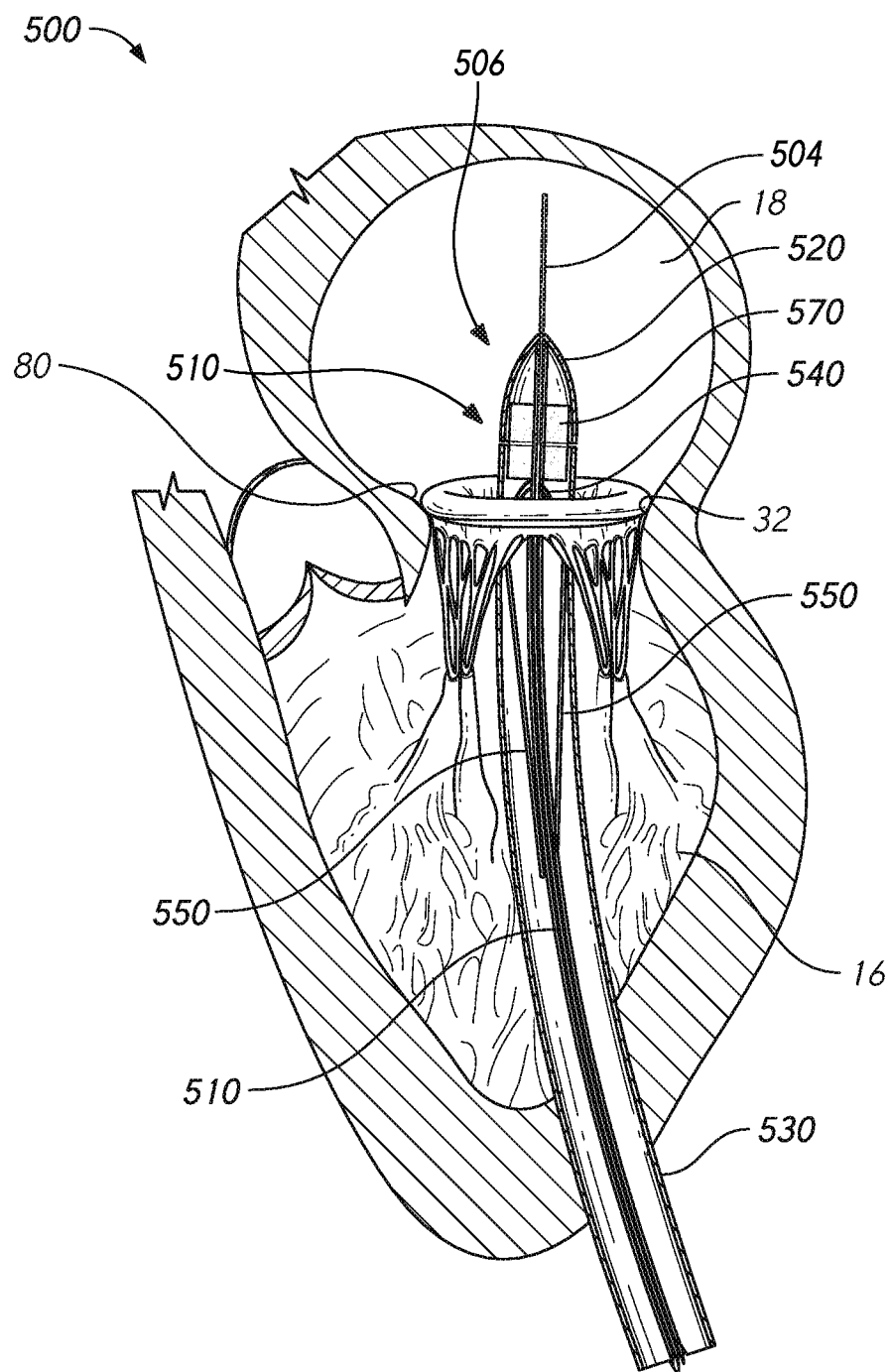
FIGS. 13-19 illustrate aspects of methods for delivering a valve prosthesis using a delivery system, according to some embodiments.

FIGS. 13-19 illustrate a transapical procedure, which can apply to any delivery method in which the distal end of the delivery system enters the left ventricle 16 before being advanced through the mitral valve into the left atrium 18. As shown in FIG. 13, a transapical procedure typically begins with an apical puncture in the left ventricle 16 followed by introduction of a guidewire 504 through the native mitral valve 32 at least into the left atrium 18. The distal end of the delivery system 500 in which the valve prosthesis 510 is enclosed is introduced into the left ventricle 16 through an introducer or trochar placed in the ventricular wall to create an open path to the mitral valve 32. However, in some embodiments, other delivery pathways can be used. For example, the distal end of the device can be introduced into the femoral artery of the patient and advanced through the femoral artery to the aorta, through the aortic valve into the left ventricle 16 then through the mitral valve 32 into the left atrium 18.

Figure 14:
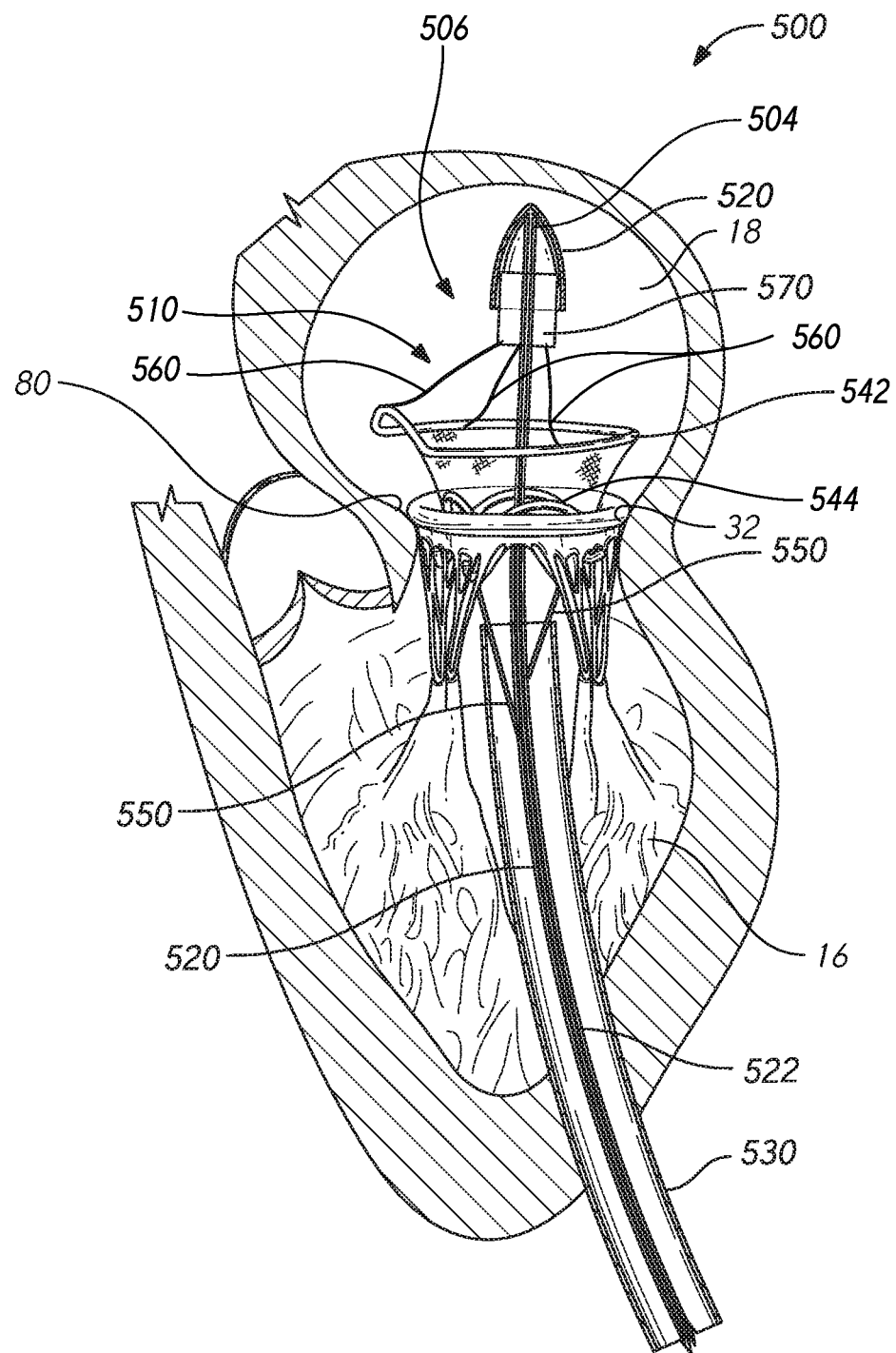

The delivery device 506 can comprise a first sheath 520, a second sheath 530, and graspers or anchor controls 550. The first sheath 520 can be coupled to a tubular member 522 that can extend through the second sheath 530. Further, the tubular member 522 can comprise a guidewire lumen configured to permit the system 500 to slide along the guidewire 504 to the target area. The prosthesis 510 can comprise an anchoring element 540 and a valve component 570. Whether transapical delivery or otherwise, once the delivery device 506 is positioned within the left ventricle 16, the distal end of the delivery device 506 (including the first sheath 520) can be advanced through the defective mitral valve 32 and into the left atrium 18 until the portion of the second sheath 530 encasing the anchoring element 540 is positioned above the mitral valve annulus 80, as shown in FIG. 13. The second sheath 530 can then be pulled in a proximal direction (away from the left atrium 18) while holding stationary the first sheath 520, the anchoring element 540, and the valve component 570 until anchoring element 540 is released from the second sheath 530 (as shown in FIG. 14). The physician can adjust the position of the anchoring element 540 by using the anchor controls 550, which remain releasably or reversibly coupled to anchoring element 540 (e.g., via hooks on the anchoring element 540, such as described above).

When the anchoring element 540 comprises the upper and lower supports 542, 544, as described above in FIGS. 5-7B, both the upper and lower supports 542, 544 can unfold and/or radially expand within the left atrium 18. The anchor controls 550 can be pulled proximally to pull the lobes and hooks of the lower support 544 through the mitral valve 32 into the left ventricle 16 while the upper support 542 remains in the left atrium 18 and the first sheath 520 with valve component 570 remains stationary. The physician can operate the delivery system 500 by moving the upper and lower supports 542, 544 rotationally or longitudinally as needed for proper placement of the upper and lower supports 542, 544 of the anchoring element 540.

After the anchoring element 540 has been initially permitted to unfold or expand within the target area, the physician can then manipulate anchor controls 550 in a proximal direction while the remaining components of the delivery device 506, including the valve component 570, can be held stationary until the lower support 544 of the anchoring element 540 is pulled proximally through the mitral valve annulus 80 such that upper support 542 and the lower support 544 of the anchoring element 540 are on opposite sides of the mitral valve annulus 80. In some embodiments, the upper support 542 of the anchoring element 540 can be released only after the lower support 544 is positioned within the left ventricle 16 and in contact with the tendineae chordae and/or left ventricular wall adjacent to the mitral valve annulus 80.

Figure 15:
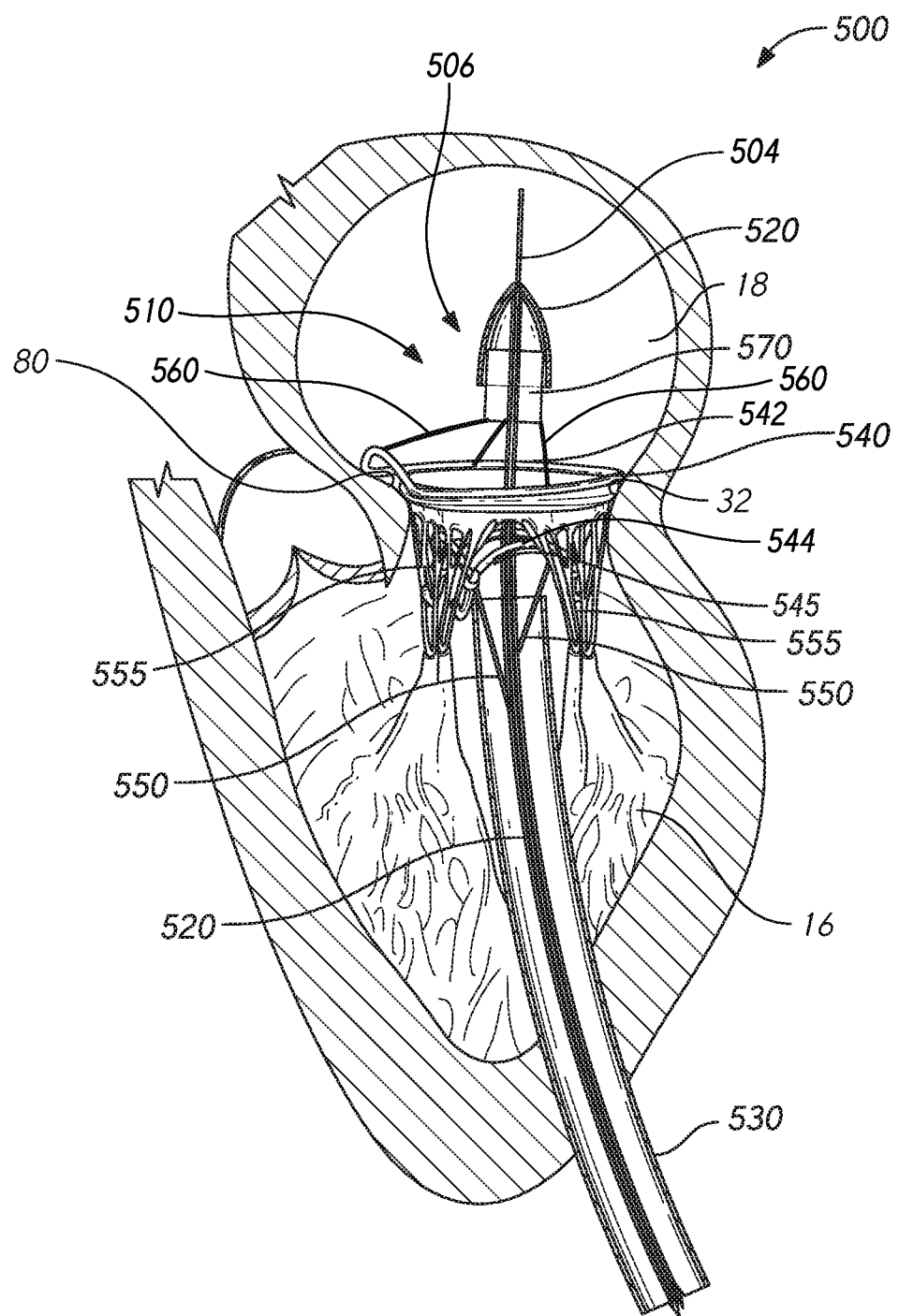
Figure 16:
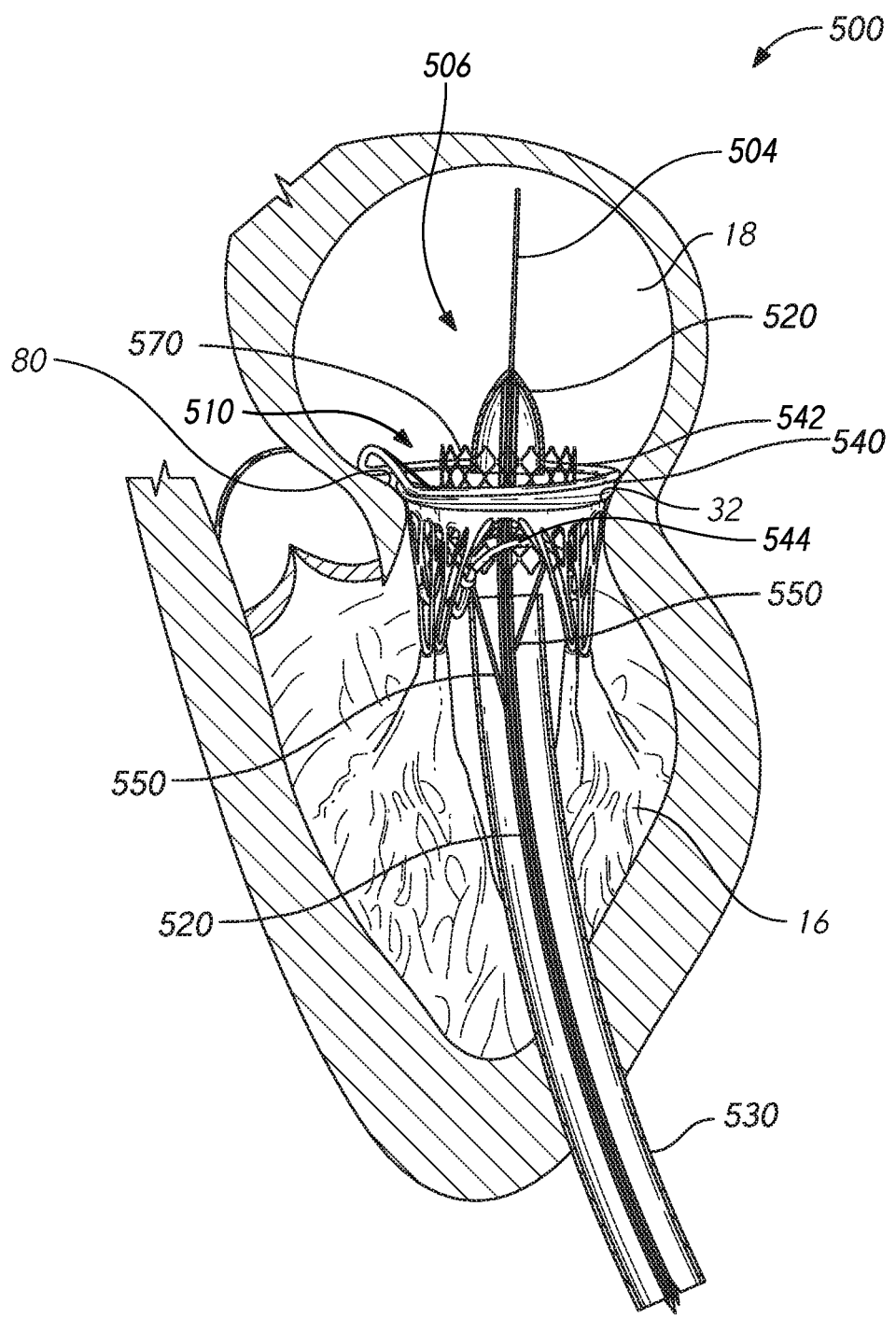

Once the anchoring element 540 is properly positioned within the valve annulus 80, the first sheath 520 encasing the valve component 570 can be moved distally (away from the left ventricle 16) a set distance which is defined by the length and positioning of coupler component 560 (shown in an approximately taut condition and FIGS. 14 and 15). The first sheath 520 can then be moved proximally while holding the anchoring element 540 stationary until resistance is felt by the operator, indicating that the valve component 570 is properly positioned within the native valve annulus 80 and relative to anchoring element 540, as shown in FIGS. 15 and 16. In some embodiments, the control unit can be programmed or configured to include a dial or knob that can move a fixed distanced dependent upon the distance the valve component 570 must be moved relative to the anchoring element 540 to reach the final position. The control unit with dial or knob can be configured such that there is a hard stop when the valve is in the correct position relative to the anchoring element 540.

After the valve component 570 has been positioned within a lumen of the anchoring element 540, the first sheath 520 can then be moved in a distal direction while the remainder of the delivery system 500, including anchoring element 540 and the valve component 570, are held stationary. As a result, the valve component 570 is uncovered and fully expands radially within the native valve annulus 80, as shown in FIG. 16. In some embodiments, the valve component 570 is released in stages—the valve component 570 can be uncovered gradually to allow progressive and steady radial expansion of the valve component 570. This staged deployment of a valve component 570 can prevent unwanted longitudinal movement of the valve component 570 relative to the anchoring element 540 and native valve annulus 80. Additionally, the staged employment can allow some further lateral, proximal movement to properly position the valve component 570 relative to the anchoring element 540.

The released valve component 570 can engage with at least the native annulus 80, also resulting in further engagement of the engagement members or hooks with papillae or the left ventricular wall. If barbs are present on the outer surface of the valve component 570, they can also engage with structures within and surrounding the native mitral valve 32 including the native leaflets.

Figure 17:
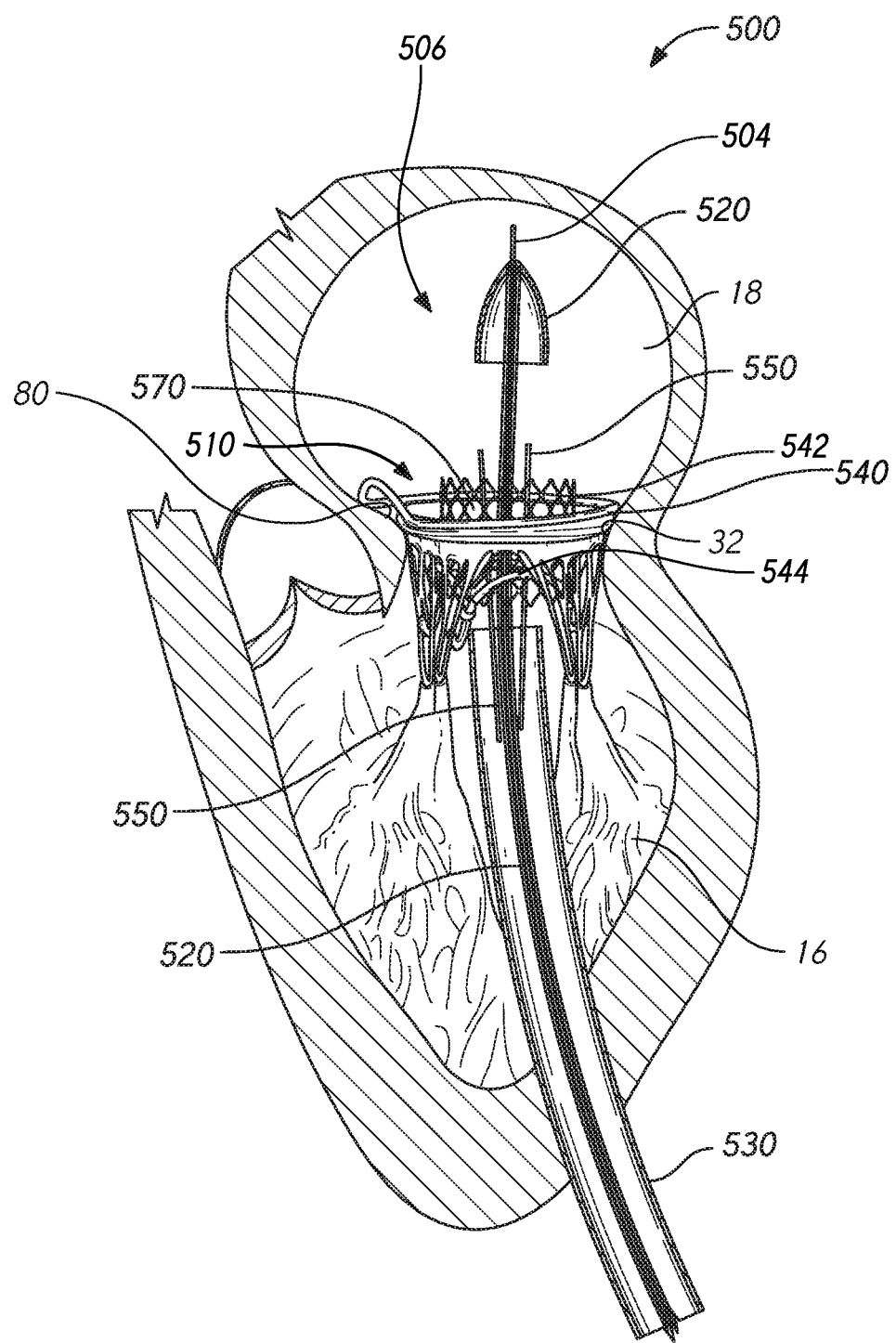
Figure 18:
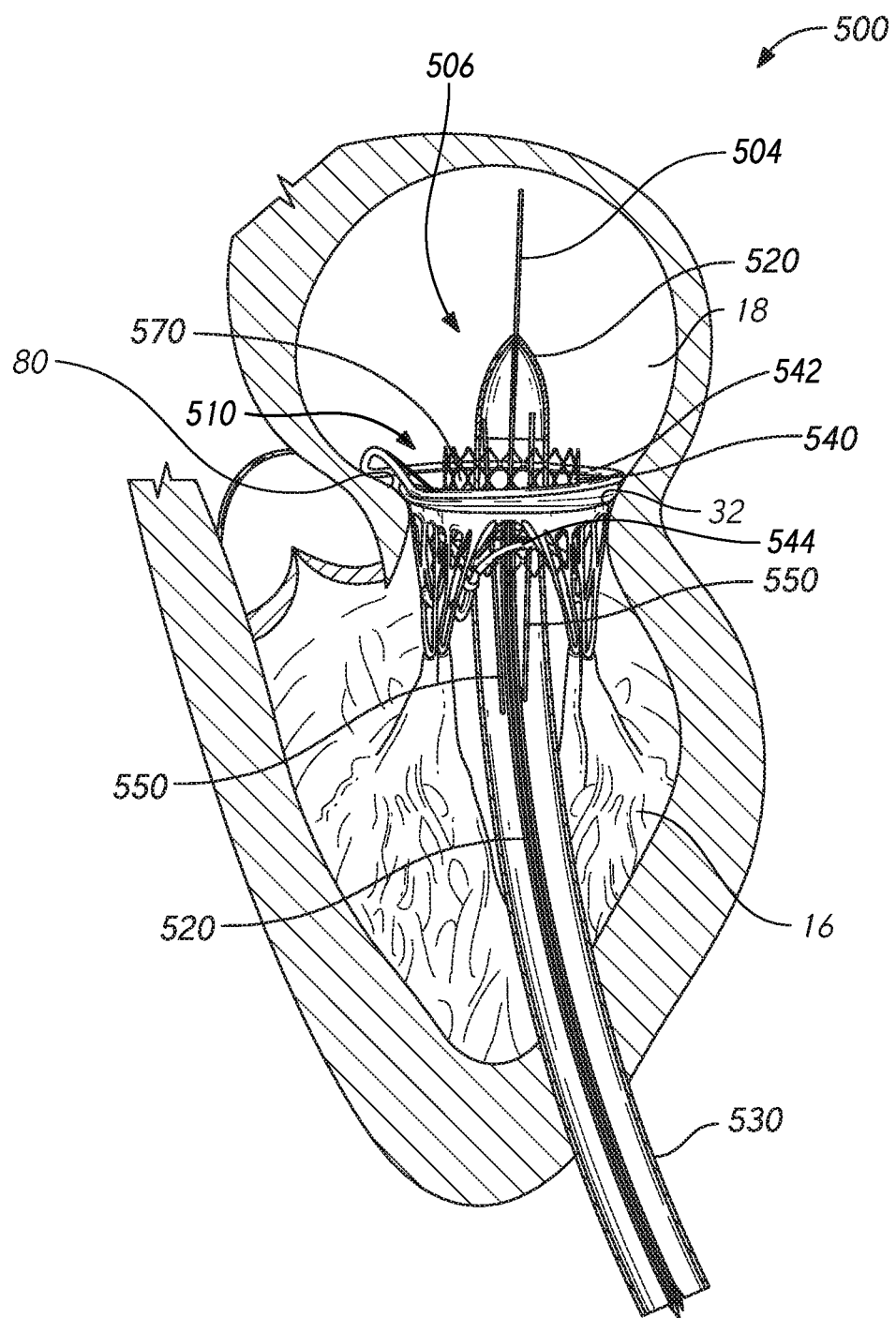
Figure 19:
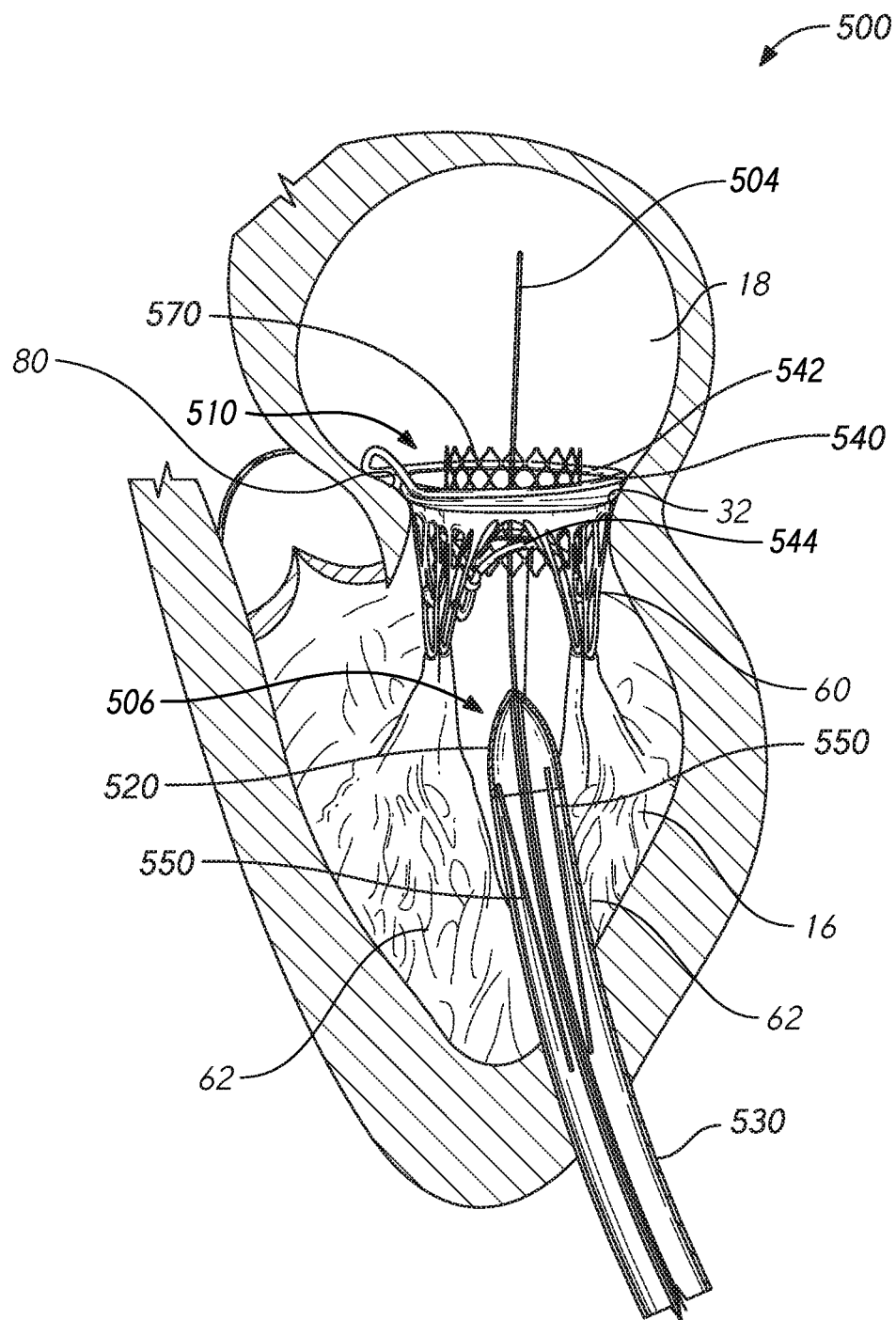

As shown in FIG. 17, the anchor control lines 550 can be disconnected from anchoring element 540 using the control unit to which the proximal end of anchor control 550 is connected. The second sheath 530 can then be pushed distally while holding other elements of the delivery device 506 stationary until anchor control 550 is fully enclosed by the second sheath 530, as shown in FIG. 18. The first sheath 520 can then be moved in a proximal direction by pulling the first sheath 520 in a proximal direction via the first sheath shaft 520 and control unit while keeping the other elements of the delivery device 506 stationary until the proximal end of the first sheath 520 is adjacent to the distal end of the second sheath 530. The delivery device 506 is then removed from the patient by pulling the delivery device 506 back along the path, leaving the valve prosthesis 510 properly in place, as shown in FIG. 19.

In some embodiments, the serial positioning of the anchoring element relative to the valve component can be manipulated, as can the type or features of the mitral valve prostheses implanted thereby. As to positioning, the valve component may be distal to the anchoring element such that the valve component enters the left ventricle then left atrium ahead of the anchoring element during, e.g., a transapical antegrade procedure or enters the left atrium then left ventricle during, e.g., a transfemoral retrograde procedure. In an alternative embodiment, the anchoring element can be distal to the valve component such that the anchoring element enters the left ventricle then left atrium ahead of the valve component during a, e.g., transapical antegrade procedure or enters the left atrium then left ventricle ahead of the valve component during a, e.g., transfemoral retrograde procedure. Regardless of the relative positioning of the anchoring element and the valve component, during delivery and prior to implantation, the two structures are positioned serially rather than concentric or partially concentric to one another thereby reducing the diameter of the valve prosthesis during delivery to the native valve annulus. This is particularly important and advantageous when delivery occurs through the venous system (through an artery and/or vein). Moreover, regardless of the relative positioning of the anchoring element and the valve component, the anchoring element and the valve component can be attached to each other by a coupler component which has a fixed length and which guides placement of the valve component relative to the anchoring element along the inflow-outflow axis of the native mitral valve annulus.

Further, in some embodiments, the method for delivering the mitral valve prosthesis can further comprises releasing a check valve, as illustrated in FIG. 12. The check valve can reduce or prevent backflow of blood through the mitral valve annulus during the implantation procedure. Accordingly, the method can further comprise, after deployment of the anchoring element, advancing the check valve out of the second sheath to a position in the left atrium wherein the frame of the check valve radially expands resulting in the fabric of the check valve spreading across an area which is greater than the area of the mitral valve annulus. The expanded frame can then be moved longitudinally until is it in a position which allows blood to flow from the left atrium to the left ventricle but does not allow the blood to flow from the left ventricle to the left atrium. Proximal ends of the check valve frame in some embodiments are attached to frame control lines but in some embodiments, the proximal ends of the check valve may be attached to and controlled by the anchoring element control sleeves. After implantation of the valve prosthesis, the check valve is removed from the patient as part of the delivery device.

FIGS. 13-19 merely illustrate some embodiments of a method for delivering a mitral valve prosthesis as described herein but a delivery device can be configured in alternative ways for both antegrade and retrograde delivery and deployment of the valve prosthesis. For example, the anchoring element may be enclosed within the first sheath, which is distal to the second sheath in which the valve component is enclosed. Accordingly, the first sheath can be advanced through the mitral valve from the left ventricle to the left atrium, wherein the first sheath is above the mitral valve annulus. The anchoring element can then be uncovered and allowed to expand its upper more supports, then pulled in a proximal directed until properly positioned within the valve annulus, as described above. At that time, the second sheath with enclosed valve component can be moved in a distal direction, with the distance moved dependent upon the length of the coupler component as described above. Once properly positioned, the first sheath is moved in a proximal direction to uncover and release the valve component and the delivery device removed from the patient.

The implantation and delivery methods, as well as the valve prosthesis devices, disclosed herein can also be used in a retrograde approach in which the distal end of the delivery system first enters the right atrium. In a retrograde approach, for example, the valve component can be enclosed within a distal first sheath while the anchoring element is enclosed within the adjacent proximal second sheath. Accordingly, the first sheath is advanced through the mitral valve, partially or fully into the left ventricle, so that the second sheath is still within the left atrium, above the mitral valve annulus. The second sheath is pulled in a proximal direction to uncover the anchoring element, thereby allowing the anchoring element to expand radially. The anchoring element can then be advanced through the mitral valve annulus and properly positioned, optionally using an imaging device, by longitudinal (inflow-outflow axis) and rotational movement. Once the anchoring element is properly positioned, the first sheath is moved in a proximal direction until it meets resistance due to the fixed length of the coupler component. Once properly positioned along the longitudinal, the first sheath can be moved distally while holding the valve component steady to gradually uncover and release the valve component. The delivery device is then removed from the patient.

Retrograde delivery of a mitral valve prosthesis as described herein can also be performed wherein the anchoring element is enclosed within a distal first sheath while the valve component is enclosed within the adjacent proximal support sheath. Accordingly, the first sheath is advanced through the aorta into the left atrium to a position approximately above the native mitral valve annulus, at which point the first sheath is advanced further to uncover and release the anchoring element. The anchoring element can be partially advanced through the mitral valve annulus as described above and the anchoring element can be properly positioned, optionally using an imaging device, by lateral and rotational movement. Once the anchoring element is properly positioned, the second sheath is moved in a proximal direction until it meets resistance due to the fixed length of the coupler component and the valve component is gradually uncovered and released within the native valve annulus, as described above. The delivery device is then removed from the patient. It is understood that use of this method requires that the valve component and anchoring element are positioned in each sheath in an orientation opposite that described, e.g., in FIGS. 11A-11C, so that the anchoring element upper and lower supports and the valve component leaflets are properly oriented in the proper direction to provide control of blood flow through the mitral valve after implantation.

Native Tissue Gathering Components

Some embodiments of the devices and methods disclosed herein can optionally comprise a native valve seal means that can be incorporated into the structure of the device or implemented using a separate component. The native valve seal means can be used to create a tighter and leak-free junction between the mitral valve prosthesis and the native valve leaflets and/or other native tissue on the ventricular side. The native valve seal means can be implemented or released into the target area during the initial mitral valve prosthesis implantation procedure or in a subsequent revision procedure. FIGS. 20A-27 illustrate various aspects and features of some of the optional embodiments that can be implemented to provide a native valve seal means.

Figures 20A, 20B:
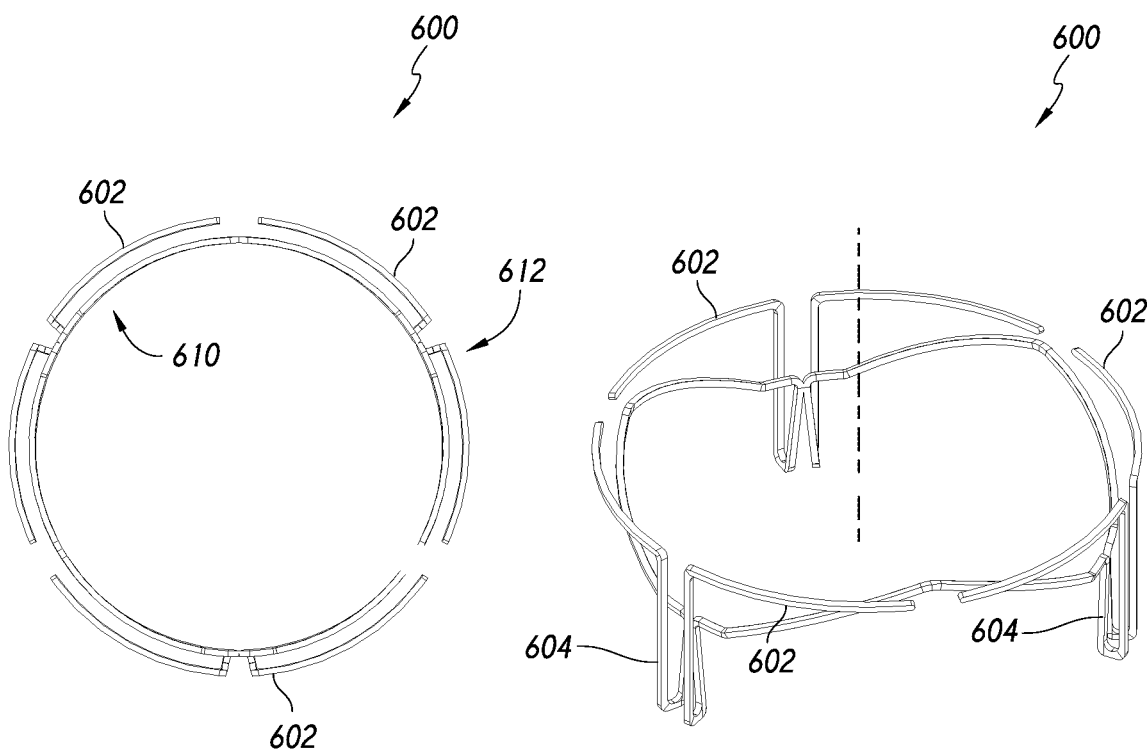

For example, FIGS. 20A-21B illustrate embodiments of anchoring elements that can comprise optional native tissue gathering structures, according to some embodiments. FIGS. 20A and 20B illustrate embodiments of an anchoring element 600, similar to that illustrated above in FIGS. 8A and 8B, that can comprise gathering arms 602. The gathering arms can extend upwardly from the hook elements. The hook elements shown in FIGS. 8A and 8B, which protrude in a radial and upward direction relative to the anchoring element, can be incorporated into the design illustrated in FIGS. 20A and 20B. However, as shown, the gathering arms 602 can extend downwardly, continuously, and upwardly from the ends of the anchoring element 600 in a bend section 604, which can enable the gathering arms 602 to be able to deflect in a radial direction away from the central axis of the anchoring element 600. Thus, whether an anchoring hook is incorporated into the illustrated design or not, the bend section can allow the anchoring hook 602 to be able to deflect away from the central axis in order to permit native tissue, such as valve leaflets, to be interposed between an inner ring 610 of the anchoring element 600 and the outer ring 612 formed by the gathering arms 602. In this manner, the native valve tissue can be sealed around the anchoring element, thereby reducing leakage and regurgitation around the valve prosthesis.

Figures 21A, 21B:
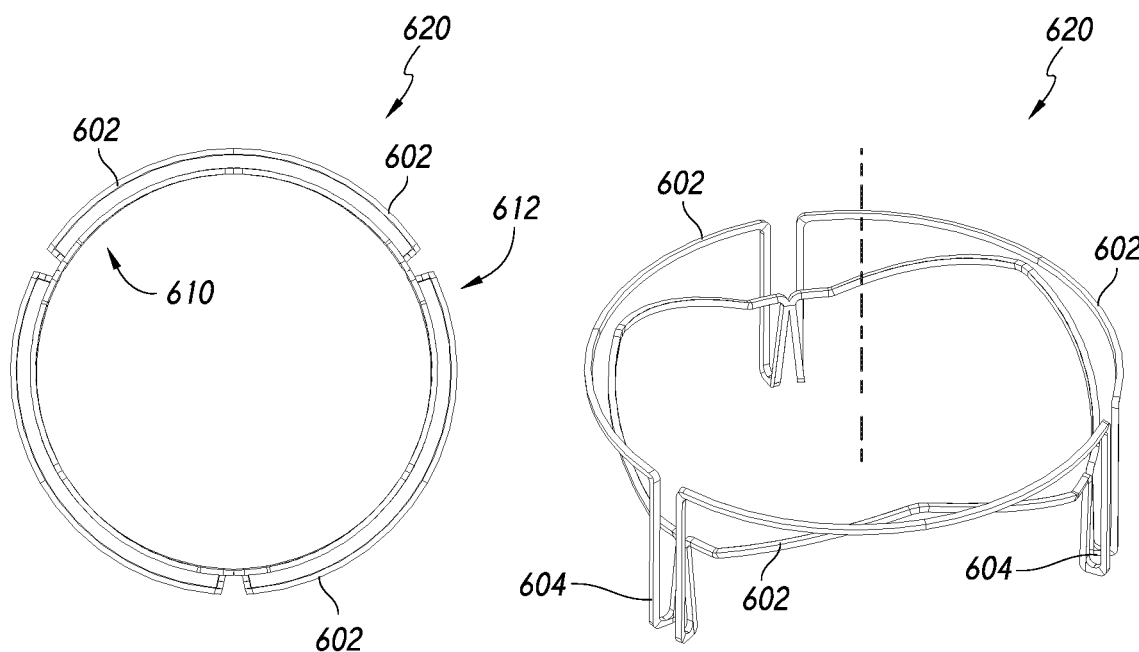

The embodiments illustrated in FIGS. 20A and 20B differ from the embodiments illustrated in FIGS. 21A and 21B in that the embodiments shown in FIGS. 21A and 21B demonstrate that the gathering arms 602 can be interconnected (thus, the element numbers for the features of the anchoring element 600 shown in FIGS. 20A and 20B are shared with the element numbers of the anchoring element 620 shown in FIGS. 21A and 21B). For example, in any of the illustrated embodiments, the wireframe of the anchoring elements can comprise a single wire that is wound in a continuous, unbroken course to create the structure and features of the anchoring element. The ends of the wire can be welded together to form the continuous, unbroken loop. However, the anchoring elements can also be formed using a plurality of independent, separate components that are joined together by a joining operation, such as welding, adhesives, or mechanical means.

Figure 22:
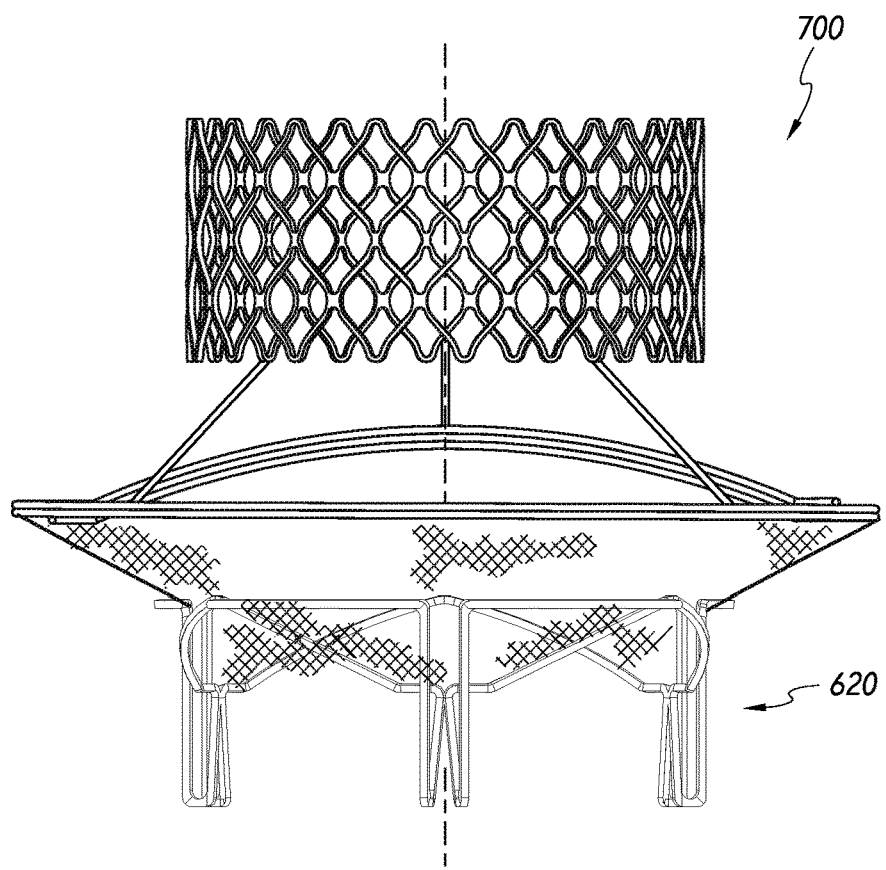
FIG. 22 shows another embodiment of a valve component and an anchoring element of a mitral valve prosthesis in a non-engaged configuration, according to some embodiments.
Figure 23:
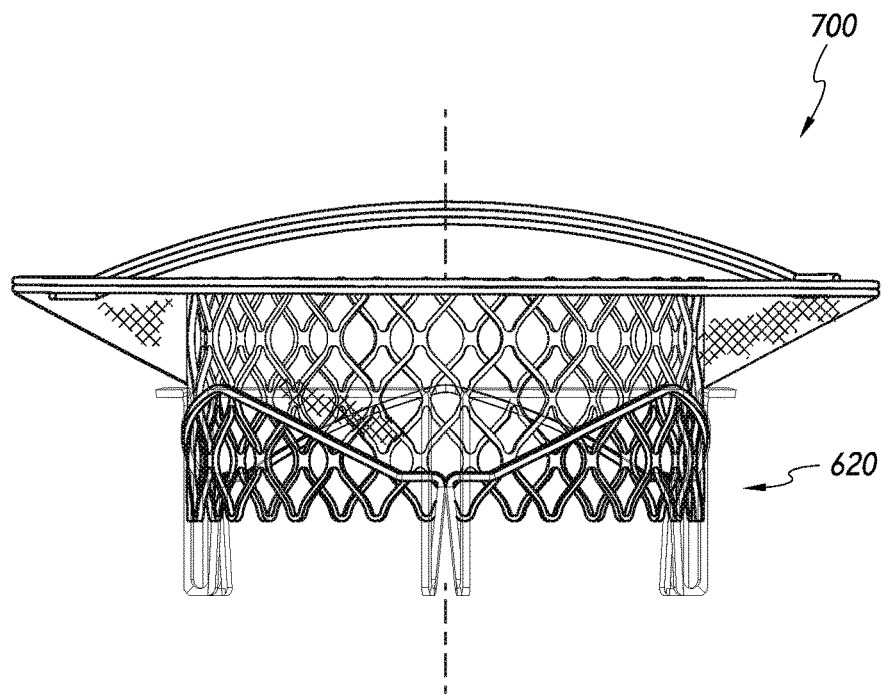
FIG. 23 shows the mitral valve prosthesis of FIG. 22 in a configuration when released in a mitral valve annulus, according to some embodiments.

FIGS. 22 and 23 illustrate embodiments of a valve component and an anchoring element of a mitral valve prosthesis 700 in a non-engaged configuration, according to some embodiments. These figures illustrate structures otherwise similar to that discussed and illustrated above and FIG. 5 and six. However, in the illustrated embodiment of the mitral valve prosthesis 700, the anchoring element 620 is shown as being a way to gather the flexible connector or tubular skirt of the prosthesis 700 toward a central axis of the prosthesis 700. Further, as discussed above with regard to FIGS. 20A-21B, the gathering arms of the anchoring element 620 can not only gather the flexible connector together, but can also collect and provide a seal between native tissue and the anchoring element and valve component of the prosthesis 700.

Figure 24:
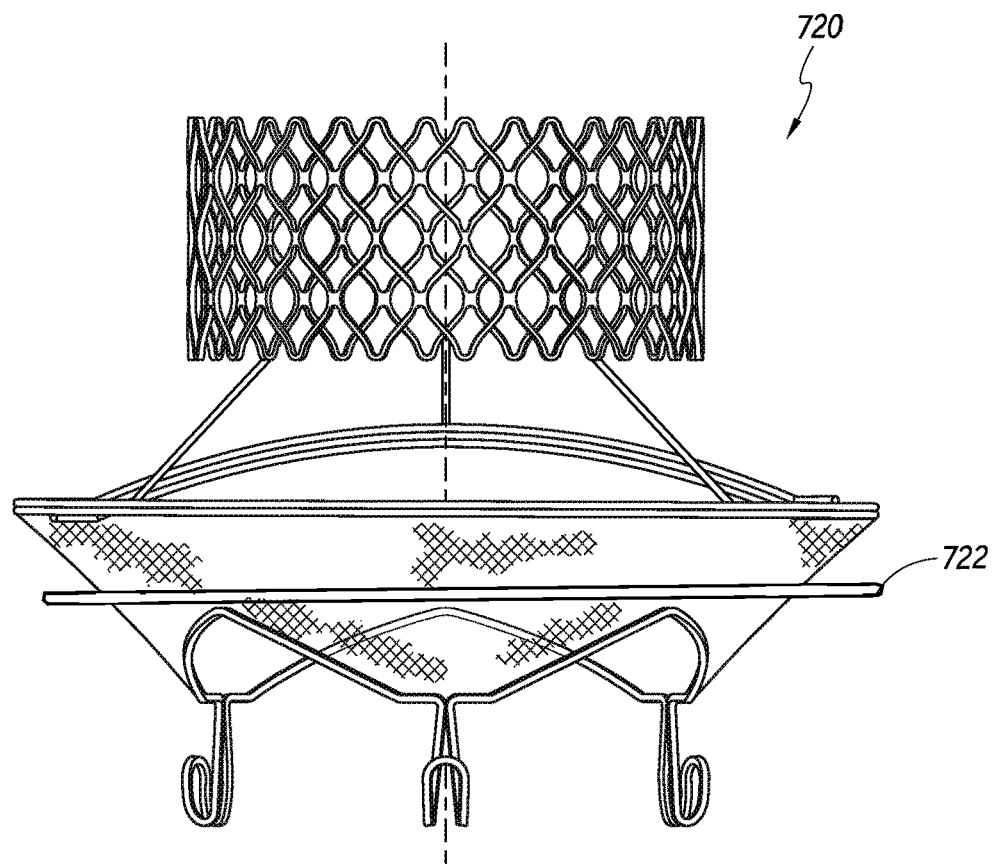
FIG. 24 shows yet another embodiment of a valve component and an anchoring element of a mitral valve prosthesis in a non-engaged configuration, according to some embodiments.
Figure 25:
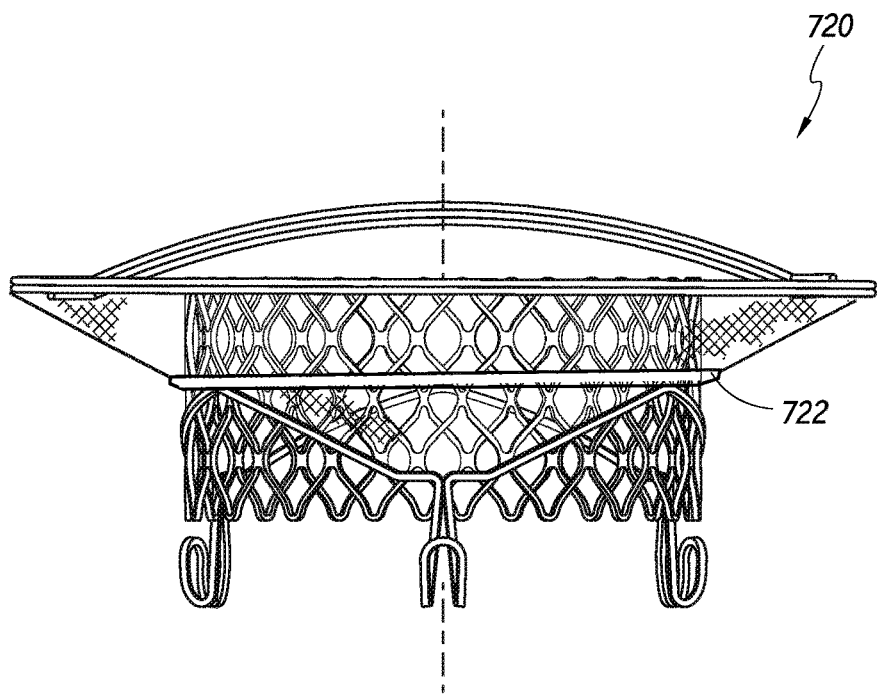
FIG. 25 shows the mitral valve prosthesis of FIG. 24 in a in a configuration when released in a mitral valve annulus, according to some embodiments.
Figure 26:
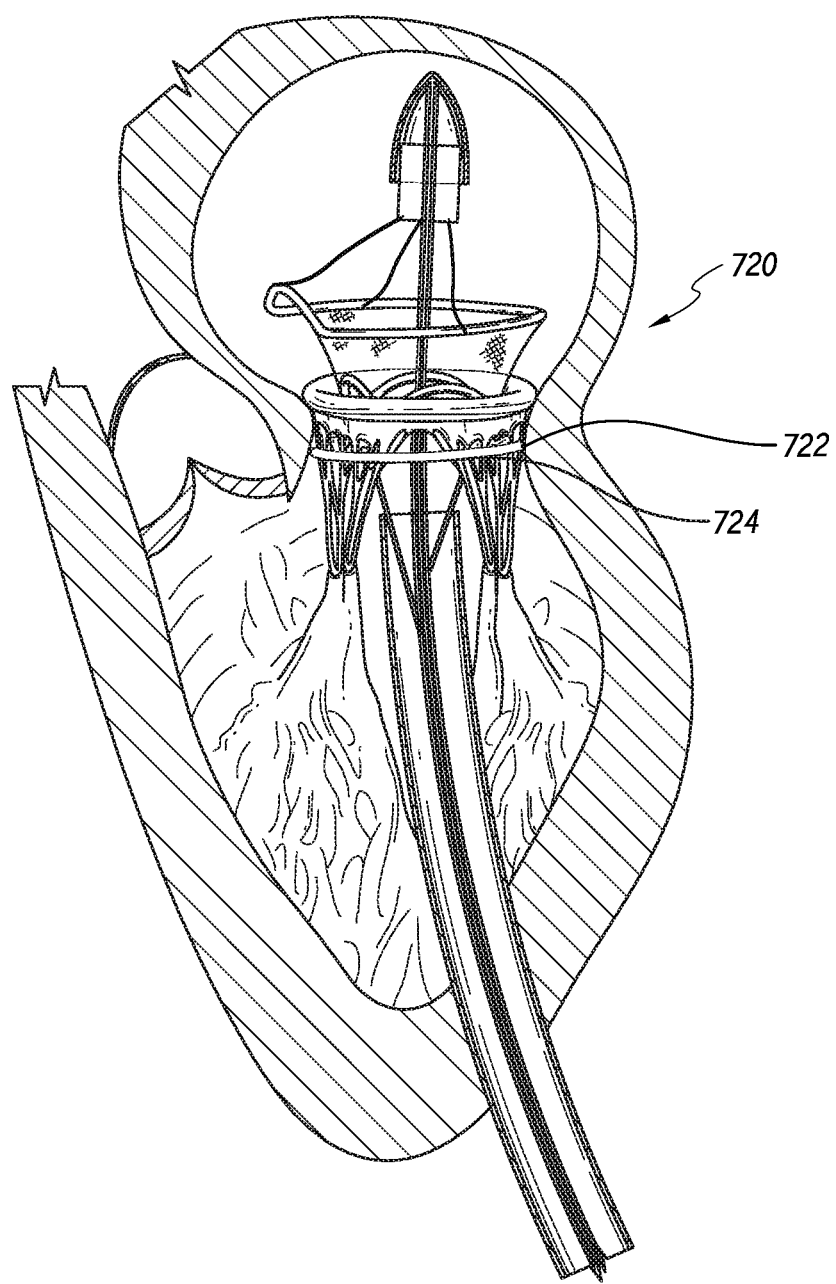
FIG. 26 illustrates aspects of optional methods for delivering a valve prosthesis using a delivery system, according to some embodiments.

FIGS. 24-27 illustrate features and aspects of another optional native valve seal means that can be implemented with a valve prosthesis 720, in accordance with some embodiments. In these figures, which illustrate aspects of systems discussed already above, which discussion will not be repeated for brevity, a gathering wire 722 can be introduced around native tissue that surrounds the anchoring element of the valve prosthesis 720 after the valve prosthesis 720 has been implanted at the target location. The gathering wire can be introduced after the valve prosthesis 720 has been expanded and accommodated in its proper, final location. Some implementations of the method can enable a position to position the gathering wire around the prosthesis 720 with native tissue gathered therebetween, in order to create a tight seal between the native tissue and an exterior of the valve prosthesis 720. FIG. 24 illustrates the gathering wire 722 in a loose state, while FIG. 25 illustrates the gathering wire 722 ratcheted or cinched around the valve prosthesis 720. Further, FIG. 26 (similar to FIG. 14 discussed above, the details of which will not be repeated here for brevity) illustrates the valve prosthesis 720 implanted within the native valve structure with the native tissue 724 ratcheted or captured between the gathering wire 722 and the valve prosthesis 720.

FIG. 27 (similar to FIG. 14 discussed above, the details of which will not be repeated here for brevity) illustrate aspects of the optional use of the gathering wire 722 when deploying a check valve, according to some embodiments. Further to the discussion of FIG. 14 above, the gathering wire 722 can be used to capture and create a seal between native tissue and the check valve when the check valve is deployed during a procedure. As illustrated, and as possible in any of the embodiments illustrated in FIGS. 24-27, the gathering wire 722 can be deployed through a separate luminal structure 726 that can extend through the sheath of the delivery system.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A mitral valve prosthesis comprising: an upper support, configured to be positioned adjacent a native mitral annulus of a patient, comprising an anterior portion and a posterior portion; a lower support, configured to engage a native mitral valve from a ventricular side, comprising at least two engagement members; a flexible connector comprising an upper end portion coupled to the upper support and a lower end portion coupled to the lower support; and a valve component comprising an outer surface and a central orifice, the valve component being disposable intermediate the upper and lower supports, the valve component being radially expandable within the lower support to abut the native mitral valve and to permit one-way flow therethrough along a central axis of the prosthesis upon expansion of the valve component; and wherein the lower support and the upper support are radially expandable from a collapsed configuration to an expanded configuration for delivery within the patient.

Clause 2. The valve prosthesis of Clause 1, wherein the upper support comprises a first ring-shaped component.

Clause 3. The valve prosthesis of Clause 2, wherein a top view of the first ring-shaped component comprises an approximately D-shaped structure.

Clause 4. The valve prosthesis of any one of the preceding clauses, wherein in an expanded state, the posterior portion of the upper support extends within a first plane.

Clause 5. The valve prosthesis of any one of the preceding clauses, wherein the posterior portion of the upper support comprises a semicircular shape.

Clause 6. The valve prosthesis of any one of the preceding clauses, wherein the anterior portion of the upper support bends along an axis extending transverse relative to the central axis.

Clause 7. The valve prosthesis of Clause 6, wherein in an expanded state, the anterior portion of the upper support extends within a second plane.

Clause 8. The valve prosthesis of Clause 6, wherein the anterior portion of the upper support comprises a semicircular shape.

Clause 9. The valve prosthesis of any one of the preceding clauses, wherein the posterior portion of the upper support extends within a first plane and the anterior portion of the upper support extends within a second plane, and wherein the first plane extends transversely relative to the second plane.

Clause 10. The valve prosthesis of Clause 9, wherein the posterior portion comprises a semicircular shape and the anterior portion comprises a semicircular shape.

Clause 11. The valve prosthesis of any one of the preceding clauses, wherein the flexible connector comprises a tubular shape.

Clause 12. The valve prosthesis of any one of the preceding clauses, wherein the flexible connector comprises a longitudinal length of between about 5 mm and about 25 mm.

Clause 13. The valve prosthesis of Clause 12, wherein the upper support is moveable within a fixed distance relative to the lower support, wherein the fixed distance being about equal to the longitudinal length of the flexible connector.

Clause 14. The valve prosthesis of any one of the preceding clauses, wherein the flexible connector comprises a fabric material.

Clause 15. The valve prosthesis of any one of the preceding clauses, wherein in an expanded state, the flexible connector comprises a tapering tubular shape.

Clause 16. The valve prosthesis of any one of the preceding clauses, wherein the valve component comprises a valve frame and a plurality of flexible prosthetic leaflets coupled to the valve frame within the central orifice.

Clause 17. The valve prosthesis of Clause 16, wherein the valve frame comprises a self-expanding tubular frame.

Clause 18. The valve prosthesis of Clause 16, wherein the valve frame comprises a balloon-expandable tubular frame.

Clause 19. The valve prosthesis of any one of the preceding clauses, wherein the valve component comprises a cover component extending about the outer surface thereof.

Clause 20. The valve prosthesis of Clause 19, wherein the cover component comprises a flexible fabric material.

Clause 21. The valve prosthesis of any one of the preceding clauses, wherein the valve component is coupled to the lower support by at least one suture member.

Clause 22. The valve prosthesis of Clause 21, wherein the suture member comprises a length of between about 5 mm and about 25 mm.

Clause 23. The valve prosthesis of any one of the preceding clauses, wherein the lower support comprises a plurality of arcuate sections, each arcuate section extending intermediate respective engagement members to form the lower support.

Clause 24. The valve prosthesis of Clause 23, wherein each arcuate section bends along an axis extending transverse relative to the central axis.

Clause 25. The valve prosthesis of any one of the preceding clauses, wherein the lower support comprises a second ring-shaped component, the at least two engagement members being coupled to the second ring-shaped component.

Clause 26. The valve prosthesis of any one of the preceding clauses, wherein the at least two engagement members comprise hooks.

Clause 27. The valve prosthesis of any one of the preceding clauses, wherein the at least two engagement members comprise first and second hooks, and wherein a distance between the first and second hooks is between about 30 mm to about 90 mm.

Clause 28. The valve prosthesis of any one of the preceding clauses, wherein the at least two engagement members comprise three hooks.

Clause 29. The valve prosthesis of any one of the preceding clauses, wherein the at least two engagement members comprise a fabric or suture material extending at least partially along surfaces of the engagement members.

Clause 30. The valve prosthesis of any one of the preceding clauses, further comprising a filler component coupled to a perimeter of the upper support.

Clause 31. The valve prosthesis of Clause 30, wherein the filler component comprises a tubular shape and an upper end portion coupled to the perimeter of the upper support.

Clause 32. The valve prosthesis of Clause 30, wherein the filler component comprises a fabric material.

Clause 33. The valve prosthesis of Clause 1, further comprising a coupler component having a first end portion coupled to the anchoring element and a second end portion coupled to the valve component, the coupler component restricting a longitudinal displacement between the anchoring element and the valve component.

Clause 34. The valve prosthesis of Clause 33, wherein the coupler component comprises a plurality of thread structures.

Clause 35. The valve prosthesis of Clause 33, wherein the coupler component comprises a fabric sheet, a suture, or a tubular cloth.

Clause 36. The valve prosthesis of any one of Clauses 33 to 35, wherein the first end portion of the coupler component is coupled to the upper support of the anchoring element and the second end portion of the coupler component is coupled to a lower portion of the valve component, the coupler component restricting a longitudinal overlap of the anchoring element and the valve component.

Clause 37. A mitral valve prosthesis comprising: an anchoring element comprising an upper support, a lower support, and a flexible connector, the upper support being configured to be positioned adjacent a native mitral annulus of a patient, the lower support being configured to engage a native mitral valve from a ventricular side, the flexible connector comprising an upper end portion coupled to the upper support and a lower end portion coupled to the lower support; and a valve component being coupled to the lower support, the valve component being radially expandable within the lower support to abut the native mitral valve.

Clause 38. The valve prosthesis of Clause 37, further comprising any features of the valve prosthesis of Clauses 1-31.

Clause 39. An valve prosthesis delivery system comprising: a mitral valve prosthesis comprising an upper support, a lower support, a flexible connector coupling the upper support to the lower support, and a valve component coupled to the lower support, the upper support being configured to be positioned adjacent a native mitral annulus of a patient, the lower support being configured to engage a native mitral valve from a ventricular side, the valve component being radially expandable within the lower support to abut the native mitral valve; and a delivery device comprising a core member, a first sheath coupled to the core member, and a second sheath extending over the core member, proximal to the first sheath, wherein the delivery device can maintain the valve prosthesis in a collapsed configuration with the first sheath enclosing at least a portion of the valve component and the second sheath encloses at least a portion of the upper and lower supports, and wherein the first and second sheath are movable to expose the upper and lower supports to anchor the valve prosthesis within the patient and thereafter release the valve component within the lower support.

Clause 40. The delivery system of Clause 39, wherein a distal portion of the valve component is enclosed by a proximal portion of the first sheath and a proximal portion of the valve component is enclosed by a distal portion of the second sheath.

Clause 41. The delivery system of any one of Clauses 39 or 40, wherein the lower support comprises a plurality of engagement members, and wherein the delivery device further comprises a plurality of anchor control components being releasably coupled to the engagement members when the valve prosthesis is in the collapsed configuration.

Clause 42. The delivery system of Clause 41, wherein the plurality of anchor control components extends longitudinally within the second sheath.

Clause 43. The delivery system of Clause 41, wherein the plurality of anchor control components are movable relative to the second sheath.

Clause 44. The delivery system of any one of Clauses 39-43, wherein a lower end portion of the flexible connector is attached to the lower support and an upper end portion of the flexible connector is attached to the upper support.

Clause 45. The delivery system of any one of Clauses 39-44, wherein a lower end portion of the flexible connector is attached to the lower support and an upper end portion of the flexible connector is attached to the upper support.

Clause 46. The delivery system of any one of Clauses 39-45, wherein the valve prosthesis comprises the valve prosthesis of any one of Clauses 1 to 33.

Clause 47. A method for implanting a mitral valve prosthesis in a heart of a patient in need thereof, comprising: providing a valve prosthesis delivery system and a mitral valve prosthesis, the delivery system comprising a core member, a first sheath coupled to the core member, and a second sheath extending along the core member, the first sheath being positioned distal to the second sheath, the mitral valve prosthesis comprising an upper support, a lower support, a flexible connector coupling the upper support to the lower support, and a valve component coupled to the lower support, the first sheath enclosing at least a portion of the valve component, the second sheath enclosing upper and lower supports; the second sheath enclosing at least a portion of the upper and lower supports, the upper support being configured to be positioned adjacent a native mitral annulus of a patient, the lower support being configured to engage a native mitral valve from a ventricular side, the valve component being radially expandable within the lower support to abut the native mitral valve; inserting at least a distal end portion of the delivery system into the heart of the patient; releasing the valve prosthesis against a native mitral valve annulus of the patient; and removing the delivery system from the patient.

Clause 48. The method of Clause 47, wherein the inserting comprises inserting the distal end portion of the delivery system into a left ventricle of the heart through an opening made in an apex of the heart.

Clause 49. The method of Clause 48, further comprising advancing the distal end portion of the delivery system into a left atrium of the heart prior to the releasing.

Clause 50. The method of any one of Clause 48 or 49, further comprising advancing the first sheath of the delivery system into a left atrium of the heart prior to the releasing.

Clause 51. The method of any one of Clauses 47-50, wherein the releasing comprises proximally retracting the second sheath to permit expansion of the upper support and positioning the upper support adjacent a native mitral annulus of the patient.

Clause 52. The method of Clause 51, wherein the releasing further comprises proximally retracting the second sheath to permit expansion of the lower support and positioning the lower support against the mitral valve from a ventricular side.

Clause 53. The method of any one of Clauses 47-52, wherein the releasing comprises permitting expansion of the upper and lower supports within a left atrium of the heart and proximally withdrawing the lower support into a left ventricle of the heart.

Clause 54. The method of Clause 52, wherein delivery system comprises a plurality of anchor control components coupled to respective engagement members of the lower support, and wherein the releasing further comprises disengaging the plurality of anchor control components from the engagement members to permit the lower support to expand against the mitral valve from the ventricular side.

Clause 55. The method of Clause 54, further comprising moving the plurality of anchor control components to reposition the lower support relative to the native mitral valve.

Clause 56. The method of Clause 54, further comprising permitting the engagement members to engage with an anterior commissure, a posterior commissure, and a posterior leaflet of the native mitral valve.

Clause 57. The method of any one of Clauses 47-56, wherein the releasing comprises aligning an anterior portion of the upper support with an aortic-mitral curtain of the native mitral valve annulus.

Clause 58. The method of Clause 57, wherein the anterior portion of the upper support extends within a vertical plane and the aligning comprises aligning the vertical plane within between 0 degrees and 20 degrees of a line representative of an aortic-mitral curtain of the native mitral valve annulus.

Clause 59. The method of Clause 58, wherein the aligning comprises aligning the vertical plane within about 10 degrees of the line representative of the aortic-mitral curtain of the native mitral valve annulus.

Clause 60. The method of any one of Clauses 47-59, wherein the releasing comprises aligning a posterior, semi-circular portion of the upper support with a posterior annulus of the native mitral valve annulus.

Clause 61. The method of any one of Clauses 47-59, further comprising gathering native tissue against the prosthesis.

Clause 62. The method of Clause 61, wherein the gathering native tissue against the prosthesis comprises positioning a gathering wire around the native tissue and the prosthesis after release of the prosthesis.

Clause 63. The method of any one of Clauses 61 to 62, wherein the gathering native tissue against the prosthesis comprises engaging a gathering arm of the prosthesis with the native tissue.

Further Considerations

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a claim may include some or all of the words (e.g., steps, operations, means or components) recited in a clause, a sentence, a phrase or a paragraph. In some embodiments, a claim may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "distal" can denote a location or direction that is away from a point of interest, such as a control unit or region of the delivery device which will be used to deliver a valve prosthesis to a native valve annulus. Additionally, the term "proximal" can denote a location or direction that is closer to a point of interest, such as a control unit or region of the delivery device which will be used to deliver a valve prosthesis.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for implanting a heart valve prosthesis in a heart of a patient in need thereof, comprising:
    positioning an upper support of an anchoring element into a left atrium of a patient;
    permitting the upper support to expand adjacent to a native valve structure of the patient;
    pulling the upper support against the native valve structure in a direction toward a left ventricle of the patient;
    positioning a lower support of the anchoring element into the left ventricle, spaced apart from the upper support, the lower support being separate from the upper support and coupled to the upper support by a tubular flexible connector, wherein the upper support has a larger diameter than the lower support, the lower support comprising a single-wire loop of material forming (i) a ring shape, (ii) a plurality of lobes, and (iii) at least two engagement members that extend in a direction opposite the plurality of lobes along a central axis of the lower support;
    permitting the lower support to expand within the left ventricle after permitting the upper support to expand; and
    engaging the at least two engagement members of the lower support with tissue of the native valve structure.

2. The method of claim 1, wherein the native valve structure comprises a mitral valve, the method further comprising rotating the upper support to align a straight side of the upper support with an aortic-mitral curtain of the mitral valve.

3. The method of claim 1, further comprising rotating the upper support to align a saddle-shape of the upper support with a shape of the native valve structure.

4. The method of claim 1, further comprising positioning a valve component radially within the flexible connector of the anchoring element and permitting the valve component to expand radially within the anchoring element.

5. The method of claim 1, further comprising interposing a filler component radially between the flexible connector and the native valve structure.

6. The method of claim 1, wherein the at least two engagement members comprise hooks, and wherein the engaging comprises engaging the hooks with chordae tendineae, an anterior commissure, a posterior commissure, or a posterior leaflet of the native valve structure.

7. The method of claim 1, further comprising inserting the anchoring element into a left ventricle through an opening made in an apex of the heart.

8. A method for implanting a heart valve prosthesis in a heart of a patient in need thereof, comprising:

providing a heart valve prosthesis delivery system and a heart valve prosthesis, the delivery system comprising a core member, a first sheath coupled to the core member, and a second sheath extending along the core member, the first sheath being positioned distal to the second sheath, the valve prosthesis comprising an upper support, a lower support separate from the upper support, wherein the upper support has a larger diameter than the lower support, the lower support comprising a single-wire loop of material forming (i) a ring shape, (ii) a plurality of lobes, and (iii) at least two engagement members that extend in a direction opposite the plurality of lobes along a central axis of the lower support, a flexible connector coupling the upper support to the lower support, and a valve component coupled to the lower support, the first sheath enclosing at least a portion of the valve component, the second sheath enclosing at least a portion of the upper and lower supports, the upper support being configured to be positioned adjacent to a native valve structure of a patient, the lower support being configured to engage the native valve structure, the valve component being radially expandable within the lower support to abut the native valve structure;

inserting at least a distal end portion of the delivery system into the heart of the patient;

permitting the upper support to expand within the native valve structure;

permitting the lower support to expand within the native valve structure after permitting the upper support to expand;

releasing the valve prosthesis within the native valve structure of the patient after permitting the lower support to expand; and removing the delivery system from the patient.

9. The method of claim 8, wherein the native valve structure comprises a mitral valve, and the inserting comprises inserting the distal end portion of the delivery system into a left ventricle of the heart through an opening made in an apex of the heart.

10. The method of claim 8, wherein the native valve structure comprises a mitral valve, the method further comprising advancing the distal end portion of the delivery system into a left atrium of the heart prior to the releasing.

11. The method of claim 8, wherein the native valve structure comprises a mitral valve, and wherein the permitting the upper support to expand comprises proximally retracting the second sheath to permit expansion of the upper support and positioning the upper support adjacent to a mitral annulus of the patient.

12. The method of claim 11, wherein the permitting the lower support to expand comprises proximally retracting the second sheath to permit expansion of the lower support and positioning the lower support against the mitral valve from a ventricular side.

13. The method of claim 8, wherein the native valve structure comprises a mitral valve, and the releasing comprises releasing the valve prosthesis against a mitral valve annulus of the patient.

14. The method of claim 8, wherein the native valve structure comprises a mitral valve, and wherein the releasing comprises permitting expansion of the upper and lower supports within a left atrium of the heart and proximally withdrawing the lower support into a left ventricle of the heart.

15. The method of claim 14, wherein the delivery system comprises a plurality of anchor control components coupled to the at least two engagement members of the lower support, and wherein the releasing further comprises disengaging the plurality of anchor control components from the at least two engagement members to permit the lower support to expand against the mitral valve from a ventricular side.

16. The method of claim 15, further comprising moving the plurality of anchor control components to reposition the lower support relative to the mitral valve.

17. The method of claim 14, wherein the releasing comprises rotating the upper support to align a straight side of the upper support with an aortic-mitral curtain of the mitral valve.

18. The method of claim 8, further comprising gathering native tissue against the prosthesis.

19. The method of claim 18, wherein the gathering native tissue against the prosthesis comprises positioning a gathering wire around the native tissue and the prosthesis after release of the prosthesis.

20. The method of claim 18, wherein the gathering native tissue against the prosthesis comprises engaging a gathering arm of the prosthesis with the native tissue.

21. A method for implanting a heart valve prosthesis in a heart of a patient in need thereof, comprising:

providing a heart valve prosthesis delivery system and a heart valve prosthesis, the delivery system comprising a core member, a first sheath coupled to the core member, and a second sheath extending along the core member, the first sheath being positioned distal to the second sheath, the valve prosthesis comprising an upper support, a lower support separate from the upper support, and a valve component coupled to the lower support, the first sheath enclosing at least a portion of the valve component, the second sheath enclosing at least a portion of the upper and lower supports, the upper support being configured to be positioned adjacent to a native valve structure of a patient, the native valve structure comprising a mitral valve, the lower support being configured to engage the native valve structure, the valve component being radially expandable within the lower support to abut the native valve structure;

inserting at least a distal end portion of the delivery system into the heart of the patient;

releasing the valve prosthesis within the native valve structure of the patient by proximally retracting the second sheath to permit expansion of the upper and lower support and positioning the upper support adjacent to a mitral annulus of the patient and the lower support against the mitral valve from a ventricular side; and removing the delivery system from the patient.

22. A method for implanting a heart valve prosthesis in a heart of a patient in need thereof, comprising:

providing a heart valve prosthesis delivery system and a heart valve prosthesis, the delivery system comprising a core member, a first sheath coupled to the core member, and a second sheath extending along the core member, the first sheath being positioned distal to the second sheath, the valve prosthesis comprising an upper support, a lower support separate from the upper support, and a valve component coupled to the lower support, the first sheath enclosing at least a portion of the valve component, the second sheath enclosing at least a portion of the upper and lower supports, the upper support being configured to be positioned adjacent to a native valve structure of a patient, the native valve structure comprising a mitral valve, the lower support being configured to engage the native valve structure, the valve component being radially expandable within the lower support to abut the native valve structure;

inserting at least a distal end portion of the delivery system into the heart of the patient;

releasing the valve prosthesis within the native valve structure of the patient by permitting expansion of the upper and lower supports within a left atrium of the heart and proximally withdrawing the lower support into a left ventricle of the heart; and removing the delivery system from the patient.

23. The method of claim 22, wherein delivery system comprises a plurality of anchor control components coupled to respective engagement members of the lower support, and wherein the releasing further comprises disengaging the plurality of anchor control components from the engagement members to permit the lower support to expand against the mitral valve from a ventricular side.

24. The method of claim 23, further comprising moving the plurality of anchor control components to reposition the lower support relative to the mitral valve.

25. The method of claim 22, wherein the releasing comprises rotating the upper support to align a straight side of the upper support with an aortic-mitral curtain of the mitral valve.

26. A method for implanting a heart valve prosthesis in a heart of a patient in need thereof, comprising:

expanding an upper support of a prosthetic valve anchor at an atrium-side location, adjacent to a mitral valve annulus of a patient, the upper support being coupled to an upper section of a tubular flexible connector;

advancing a lower support of the prosthetic valve anchor through the mitral valve annulus toward the left ventricle, the lower support being formed as a single-wire loop that comprises a ring shape, a plurality of lobes, and a plurality of engagement members, the lower support being coupled to a bottom section of the tubular flexible connector, wherein the advancing permits the plurality of lobes and tubular flexible connector to collectively expand within and into apposition against leaflets of the mitral valve for forming a lumen therethrough;

engaging the plurality of engagement members with native tissue; and expanding a prosthetic valve within the lumen against the tubular flexible connector for minimizing paravalvular leakage.

* * * * *